United States Patent
Pratt et al.

(10) Patent No.: US 9,776,990 B2
(45) Date of Patent: Oct. 3, 2017

(54) ISOINDOLONE DERIVATIVES

(71) Applicant: AbbVie Inc., North Chicago, IL (US)

(72) Inventors: John K Pratt, Kenosha, WI (US); Dachun Liu, Vernon Hills, IL (US); Chang H Park, Wadsworth, IL (US); George S Sheppard, Wilmette, IL (US); Lisa A Hasvold, Grayslake, IL (US); Le Wang, Vernon Hills, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 13/796,731

(22) Filed: Mar. 12, 2013

(65) Prior Publication Data

US 2013/0281450 A1    Oct. 24, 2013

Related U.S. Application Data

(63) Continuation of application No. PCT/CN2012/074411, filed on Apr. 20, 2012.

(51) Int. Cl.

| | |
|---|---|
| A61K 31/4035 | (2006.01) |
| A61K 31/404 | (2006.01) |
| C07D 209/44 | (2006.01) |
| C07D 209/48 | (2006.01) |
| C07D 409/12 | (2006.01) |
| C07D 403/10 | (2006.01) |
| C07D 405/12 | (2006.01) |
| A61K 31/5377 | (2006.01) |
| A61K 45/06 | (2006.01) |
| C07D 405/04 | (2006.01) |
| C07D 403/04 | (2006.01) |
| A61K 31/4184 | (2006.01) |
| C07D 405/10 | (2006.01) |
| C07D 401/12 | (2006.01) |
| A61K 31/4439 | (2006.01) |
| A61K 31/4709 | (2006.01) |
| C07D 403/12 | (2006.01) |
| A61K 31/416 | (2006.01) |
| C07D 417/12 | (2006.01) |
| A61K 31/427 | (2006.01) |
| C07D 401/10 | (2006.01) |
| C07D 409/10 | (2006.01) |

(52) U.S. Cl.
CPC .......... *C07D 409/12* (2013.01); *A61K 31/404* (2013.01); *A61K 31/4035* (2013.01); *A61K 31/416* (2013.01); *A61K 31/4184* (2013.01); *A61K 31/427* (2013.01); *A61K 31/4439* (2013.01); *A61K 31/4709* (2013.01); *A61K 31/5377* (2013.01); *A61K 45/06* (2013.01); *C07D 209/44* (2013.01); *C07D 209/48* (2013.01); *C07D 401/10* (2013.01); *C07D 401/12* (2013.01); *C07D 403/04* (2013.01); *C07D 403/10* (2013.01); *C07D 403/12* (2013.01); *C07D 405/04* (2013.01); *C07D 405/10* (2013.01); *C07D 405/12* (2013.01); *C07D 409/10* (2013.01); *C07D 417/12* (2013.01)

(58) Field of Classification Search
CPC . A61K 31/4035; A61K 31/404; C07D 209/48
See application file for complete search history.

(56) References Cited

U.S. PATENT DOCUMENTS

| | | |
|---|---|---|
| 7,511,013 B2 | 3/2009 | Molino et al. |
| 7,514,068 B2 | 4/2009 | Tung |
| 7,521,421 B2 | 4/2009 | Naicker et al. |
| 7,528,131 B2 | 5/2009 | Persichetti et al. |
| 7,531,685 B2 | 5/2009 | Czarnik |
| 7,534,814 B2 | 5/2009 | Ascher et al. |
| 7,538,189 B2 | 5/2009 | Naicker et al. |
| 2005/0222034 A1 | 10/2005 | Hsu et al. |

(Continued)

FOREIGN PATENT DOCUMENTS

| | | |
|---|---|---|
| EP | 0989131 A1 | 3/2000 |
| EP | 1887008 A1 | 2/2008 |

(Continued)

OTHER PUBLICATIONS

Banerjee C., et al., "BET Bromodomain Inhibition as a Novel Strategy for Reactivation of HIV-1," Journal of Leukocyte Biology, 2012, vol. 92 (6), pp. 1147-1154.
Barraja P., et al., "Synthesis of the New Ring System 6,8-dihydro-5H-pyrrolo[3,4-h]Quinazoline," Tetrahedron Letters, 2009, vol. 50 (38), pp. 5389-5391.
Blagojevic, N. et al., "Role of heavy water in Boron Neutron Capture Therapy," Topics in Dosimetry & Treatment Planning for Neutron Capture Therapy, 1994, pp. 125-134.
Blake, M. I. et al., "Studies With Deuterated Drugs," Journal of Pharmaceutical Sciences, 1975, vol. 64 (3), pp. 367-391.

(Continued)

Primary Examiner — Kendra D Carter
(74) Attorney, Agent, or Firm — Glen Gesicki

(57) ABSTRACT

The present invention provides for compounds of formula (I)

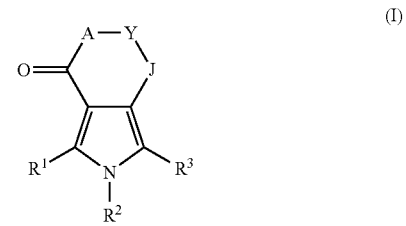

wherein A, Y, J, $R^1$, $R^2$, and $R^3$ have any of the values defined therefor in the specification, and pharmaceutically acceptable salts thereof, that are useful as agents in the treatment of diseases and conditions, including inflammatory diseases, diabetes, obesity, cancer, and AIDS. Also provided are pharmaceutical compositions comprising one or more compounds of formula I.

10 Claims, No Drawings

(56) References Cited

U.S. PATENT DOCUMENTS

| | | | |
|---|---|---|---|
| 2008/0119457 A1 | 5/2008 | Huang et al. | |
| 2009/0082471 A1 | 3/2009 | Czarnik | |
| 2009/0088416 A1 | 4/2009 | Czarnik | |
| 2009/0093422 A1 | 4/2009 | Tung et al. | |
| 2009/0105147 A1 | 4/2009 | Masse | |
| 2009/0105307 A1 | 4/2009 | Galley et al. | |
| 2009/0105338 A1 | 4/2009 | Czarnik | |
| 2009/0111840 A1 | 4/2009 | Herold et al. | |
| 2009/0118238 A1 | 5/2009 | Czarnik | |
| 2009/0131363 A1 | 5/2009 | Harbeson | |
| 2009/0131485 A1 | 5/2009 | Liu et al. | |
| 2009/0137457 A1 | 5/2009 | Harbeson | |
| 2010/0286127 A1 | 11/2010 | Miyoshi et al. | |

FOREIGN PATENT DOCUMENTS

| | | | |
|---|---|---|---|
| EP | 2239264 | A1 | 10/2010 |
| JP | 2008156311 | A | 7/2008 |
| WO | 9507271 | A1 | 3/1995 |
| WO | 9710223 | A1 | 3/1997 |
| WO | 9802430 | A1 | 1/1998 |
| WO | 0138377 | A1 | 5/2001 |
| WO | 0172812 | A1 | 10/2001 |
| WO | 2005099353 | A2 | 10/2005 |
| WO | 2006008754 | A1 | 1/2006 |
| WO | 2006032470 | A1 | 3/2006 |
| WO | 2008024978 | A2 | 2/2008 |
| WO | 2009084693 | A1 | 7/2009 |
| WO | 2011054553 | A1 | 5/2011 |
| WO | 2011054843 | A1 | 5/2011 |
| WO | 2011054844 | A1 | 5/2011 |
| WO | 2011054845 | A1 | 5/2011 |
| WO | 2011054846 | A1 | 5/2011 |
| WO | 2011054848 | A1 | 5/2011 |
| WO | 2011054851 | A1 | 5/2011 |
| WO | 2012075456 | A1 | 6/2012 |

OTHER PUBLICATIONS

Brickner, S.J. et al., "Synthesis and Antibacterial Activity of U-100592 and U-100766, Two Oxazolidinone Antibacterial Agents for the Potential Treatment of Multidrug-Resistant Gram-Positive Bacterial Infections," Journal of Medicinal Chemistry, 1996, vol. 39 (3), pp. 673-679.
Chung C.W., et al., "Discovery and Characterization of Small Molecule Inhibitors of the BET Family Bromodomains," Journal of Medicinal Chemistry, 2011, vol. 54 (11), pp. 3827-3838.
Chung C.W., "Small Molecule Bromodomain Inhibitors: Extending the Druggable Genome," Progress in Medicinal Chemistry, 2012, vol. 51, pp. 1-55.
Czajka, D. M. et al., "Effect of Deuterium Oxide on the Reproductive Potential of Mice," Annals of the New York Academy of Sciences, 1960, vol. 84, pp. 770-779.
Czajka, D. M. et al., "Physiological Effects of Deuterium on Dogs," American Journal of Physiology, 1961, vol. 201 (2), pp. 357-362.
Dawson M.A., et al., "Inhibition of BET Recruitment to Chromatin as an Effective Treatment for MLL-fusion Leukaemia," Nature, 2011, vol. 478 (7370), pp. 529-533.
Delmore J.E., et al., "BET Bromodomain Inhibition as a Therapeutic Strategy to Target c-Myc," Cell, 2011, vol. 146 (6), pp. 904-917.
Denis G.V., "Bromodomain Coactivators in Cancer, Obesity, type 2 Diabetes, and Inflammation," Discovery Medicine, 2010, vol. 10 (55), pp. 489-499.
Eastwood B.J., et al., "The Minimum Significant Ratio: A Statistical Parameter to Characterize the Reproducibility of Potency Estimates from Concentration-Response Assays and Estimation by Replicate-Experiment Studies," Journal of Biomolecular Screening, 2006, vol. 11 (3), pp. 253-261.
Filippakopoulos P., et al., "Selective Inhibition of BET Bromodomains," Nature, 2010, vol. 468 (7327), pp. 1067-1073.
Foster, A. B. et al., "Deuterium Isotope Effects in the Metabolism of Drugs and Xenobiotics: Implications for Drug Design," Advances in Drug Research, 1985, vol. 14, pp. 2-36.
Gabbutt C.D., et al., et al., "A Facile Route to Pyrroles, Isoindoles and Hetero Fused Analogues," Journal of the Chemical Society, Perkin Transactions, 2002, vol. 1 (24), pp. 2799-2808.
Greene T.W., et al., in: Protective Groups in Organic Synthesis, 3rd Edition, John Wiley and Sons, Inc., 1999, Preface, Table of Contents, Abbreviations.
Hewings D.S., et al., "Progress in the Development and Application of Small Molecule Inhibitors of Bromodomain-acetyl-lysine Interactions," Journal of Medicinal Chemistry, 2012, vol. 55 (22), pp. 9393-9413.
Huang B., et al., "Brd4 Coactivates Transcriptional Activation of NF-kappaB Via Specific Binding to Acetylated RelA," Molecular and Cellular Biology, 2009, vol. 29 (5), pp. 1375-1387.
International Search Report and Written Opinion for Application No. PCT/CN2012/074411, mailed on Jan. 24, 2013, 11 pages.
International Search Report and Written Opinion for Application No. PCT/CN2012/076748, mailed on Mar. 21, 2013, 14 pages.
International Search Report and Written Opinion for Application No. PCT/US2013/037297, mailed on Jul. 11, 2013, 11 pages.
International Search Report for Application No. PCT/EP2010/066695, mailed on Feb. 7, 2011, 2 pages.
Jang M.K., et al., "The Bromodomain Protein Brd4 is a Positive Regulatory Component of P-TEFb and Stimulates RNA Polymerase II-dependent Transcription," Molecular Cell, 2005, vol. 19 (4), pp. 523-534.
Kato, S. et al., "Synthesis of Deuterated Mosapride Citrate," Journal of Labelled Compounds and Radiopharmaceuticals, 1995, vol. 36 (10), pp. 927-932.
Kushner, et al., "Pharmacological uses and perspectives of heavy water and deuterated compounds," Canadian Journal of Physiology and Pharmacology, 1999, vol. 77 (2), pp. 79-88.
Leroy G., et al., "The Double Bromodomain Proteins Brd2 and Brd3 Couple Histone Acetylation to Transcription," Molecular Cell, 2008, vol. 30 (1), pp. 51-60.
Lizondo, J. et al., "Linezolid: Oxazolidinone antibacterial," Drugs of the Future, 1996, vol. 21 (11), pp. 1116-1123.
Mallesham, B. et al., "Highly Efficient CuI-Catalyzed Coupling of Aryl Bromides With Oxazolidinones Using Buchwald's Protocol: A Short Route to Linezolid and Toloxatone," Organic Letters, 2003, vol. 5 (7), pp. 963-965.
Matzuk M.M., et al., "Small-molecule Inhibition of BRDT for Male Contraception," Cell, 2012, vol. 150 (4), pp. 673-684.
Mertz J.A., et al., "Targeting MYC Dependence in Cancer by Inhibiting BET Bromodomains," Proceedings of the National Academy of Sciences, 2011, vol. 108 (40), pp. 16669-16674.
Nicodeme E., et al., "Suppression of Inflammation by a Synthetic Histone Mimic," Nature, 2010, vol. 468 (7327), pp. 1119-1123.
Prescott D.M., "Methods in Cell Biology", Academic Press, 1976, Table of Contents.
Prinjha R.K., et al., "Place your BETs: the Therapeutic Potential of Bromodomains," Trends in Pharmacological Sciences, 2012, vol. 33 (3), pp. 146-153.
Sutton, V.R. et al., "Bcl-2 Prevents Apoptosis Induced by Perforin and Granzyme B, but Not That Mediated by Whole Cytotoxic Lymphocytes," Journal of Immunology, 1997, vol. 158 (12), pp. 5783-5790.
Thomson, J.F., "Physiological Effects of D20 in Mammals," Annals of the New York Academy of Sciences, 1960, vol. 84, pp. 736-744.
Wang F., et al., "Brd2 Disruption in Mice Causes Severe Obesity without Type 2 Diabetes," Biochemical Journal, 2010, vol. 425, pp. 71-83.
Yang Z., et al., "Brd4 Recruits P-TEFb to Chromosomes at Late Mitosis to Promote G1 Gene Expression and Cell Cycle Progression," Molecular and Cellular Biology, 2008, vol. 28 (3), pp. 967-976.
Zhang G., et al., "Down-regulation of NF-κB Transcriptional Activity in HIV-associated Kidney Disease by BRD4 Inhibition," Journal of Biological Chemistry, 2012, vol. 287 (34), pp. 28840-28851.
Zuber J., et al., "RNAi Screen Identifies Brd4 as a Therapeutic Target in Acute Myeloid Leukaemia," Nature, 2011, vol. 478 (7370), pp. 524-528.
Supplementary European Search Report for Application No. EP12874480, mailed on Sep. 30, 2015, 6 pages.

ISOINDOLONE DERIVATIVES

CROSS-REFERENCES TO RELATED APPLICATIONS

This application claims the benefit of PCT Application No. PCT/CN2012/074411, filed on Apr. 20, 2012, the teachings of which are herein incorporated by reference.

BACKGROUND

Bromodomains refer to conserved protein structural folds which bind to N-acetylated lysine residues that are found in some proteins. The BET family of bromodomain containing proteins is comprised of four members (BRD2, BRD3, BRD4 and BRDt). Each member of the BET family employs two bromodomains to recognize N-acetylated lysine residues found primarily, but not exclusively, on the amino-terminal tails of histone proteins. These interactions modulate gene expression by recruiting transcription factors to specific genome locations within chromatin. For example, histone-bound BRD4 recruits the transcription factor P-TEFb to promoters, resulting in the expression of a subset of genes involved in cell cycle progression (Yang et al., Mol. Cell. Biol. 28: 967-976 (2008)). BRD2 and BRD3 also function as transcriptional regulators of growth promoting genes (LeRoy et al., Mol. Cell. 30: 51-60 (2008)). BET family members were recently established as being important for the maintenance of several cancer types (Zuber et al., Nature 478: 524-528 (2011); Mertz et al; Proc. Nat'l. Acad. Sci. 108: 16669-16674 (2011); Delmore et al., Cell 146: 1-14, (2011); Dawson et al., Nature 478: 529-533 (2011)). BET family members have also been implicated in mediating acute inflammatory responses through the canonical NF-KB pathway (Huang et al., Mol. Cell. Biol. 29: 1375-1387 (2009)) resulting in the upregulation of genes associated with the production of cytokines (Nicodeme et al., Nature 468: 1119-1123, (2010)). Suppression of cytokine induction by BET bromodomain inhibitors has been shown to be an effective approach to treat inflammation-mediated kidney disease in an animal model (Zhang, et al., J. Biol. Chem. 287: 28840-28851 (2012)). BRD2 function has been linked to predisposition for dyslipidemia or improper regulation of adipogenesis, elevated inflammatory profiles and increased susceptibility to autoimmune diseases (Denis, Discovery Medicine 10: 489-499 (2010)). The human immunodeficiency virus utilizes BRD4 to initiate transcription of viral RNA from stably integrated viral DNA (Jang et al., Mol. Cell, 19: 523-534 (2005)). BET bromodomain inhibitors have also been shown to reactivate HIV transcription in models of latent T cell infection and latent monocyte infection (Banerjee, et al, J. Leukocyte Biol. doi:10.1189/jlb.0312165). BRDt has an important role in spermatogenesis that is blocked by BET bromodomain inhibitors (Matzuk, et al., Cell 150: 673-684 (2012)). Thus, compounds that inhibit the binding of BET family bromodomains to their cognate acetylated lysine proteins are being pursued for the treatment of cancer, inflammatory diseases, kidney diseases, diseases involving metabolism or fat accumulation, and some viral infections, as well as for providing a method for male contraception. Accordingly, there is an ongoing medical need to develop new drugs to treat these indications.

SUMMARY

In one aspect, the present invention relates to compounds of Formula (I), or a pharmaceutically acceptable salt thereof,

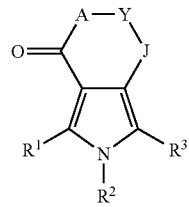

(I)

wherein A is $C(R^8R^9)$; Y is $C(R^6R^7)$; J is $C(R^4R^5)$; $R^1$ is hydrogen or $C_1$-$C_3$ alkyl; $R^2$ is hydrogen or $C_1$-$C_3$ alkyl; $R^3$ is heteroaryl, 9 to 12 membered bicyclic aryl, napthalen-1yl, unsubstituted phenyl, or X, wherein X is

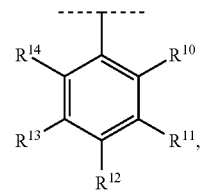

wherein said heteroaryl, 9 to 12 membered bicyclic aryl, or napthalen-1-yl may be substituted with one to three substituents independently selected from the group consisting of $NR^{16}R^{18}$, halo, hydroxyl, $C_1$-$C_3$ alkyl, —O-aryl, $C_1$-$C_3$ alkylene-aryl, $C_1$-$C_3$ alkylene-O-aryl, —S-aryl, —O—$C_1$-$C_3$ alkylene-aryl, —$NR^{16}$—$SO_2$—$NR^{18}$—$C_1$-$C_3$ alkyl, —$NR^{16}$—$SO_2$—$NR^{18}$—$C_1$-$C_3$ haloalkyl, —$NR^{16}$—$SO_2$—$C_1$-$C_3$ alkyl, —$NR^{16}$—$SO_2$—$C_1$-$C_3$ haloalkyl, $SO_2$—$NR^{16}R^{18}$, $SO_2$—$C_1$-$C_3$ alkyl, —O—$C_1$-$C_3$ alkyl, —C(O)—O—$C_1$-$C_3$ alkyl, —C(O)—OH, —C(O)—$NR^{16}R^{18}$, —C(O)—$NH(C_1$-$C_3$ haloalkyl), —C(O)—$NH(C_1$-$C_3$ alkylene-heterocycloalkyl), —C(O)—NH(heteroaryl), —NH—C(O)—$C_1$-$C_3$ alkyl, —NH—C(O)-heteroaryl, heterocycloalkyl, —O—$C_1$-$C_3$ alkylene-heterocycloalkyl, —O—$C_3$-$C_{14}$ cycloalkyl, —O—$C_1$-$C_3$ alkylene-$C_3$-$C_{14}$ cycloalkyl, —O—$C_1$-$C_3$ alkylene-heteroaryl, or heteroaryl;

wherein X is substituted as set out in (i) or (ii):
four of $R^{10}$, $R^{11}$, $R^{12}$, $R^{13}$, and $R^{14}$ are hydrogen, and one of $R^{10}$, $R^{11}$, $R^{12}$, $R^{13}$, or $R^{14}$ is selected from the following groups:
  $R^{10}$ is $NR^{16}R^{18}$, halo, hydroxyl, $C_1$-$C_3$ alkyl, $C_1$-$C_3$ alkylene-aryl, $C_1$-$C_3$ alkylene-O-aryl, —S-aryl, —O—$C_1$-$C_3$ alkylene-aryl, —$NR^{16}$—$SO_2$—$NR^{18}$—$C_1$-$C_3$ alkyl, —$NR^{16}$—$SO_2$—$NR^{18}$—$C_1$-$C_3$ haloalkyl, —$NR^{16}$—$SO_2$—$C_1$-$C_3$ alkyl, —$NR^{16}$—$SO_2$—$C_1$-$C_3$ haloalkyl, $SO_2$—$NR^{16}R^{18}$, $SO_2$—$C_1$-$C_3$ alkyl, —O—$C_1$-$C_3$ alkyl, —C(O)—O—$C_1$-$C_3$ alkyl, —C(O)—OH, —C(O)—$NR^{16}R^{18}$, —C(O)—$NH(C_1$-$C_3$ haloalkyl), —C(O)—$NH(C_1$-$C_3$ alkylene-heterocycloalkyl), —C(O)—NH(heteroaryl), NH—C(O)—$C_1$-$C_3$ alkyl, NH—C(O)-heteroaryl, heterocycloalkyl, —O—$C_1$-$C_3$ alkylene-heterocycloalkyl, —O—$C_3$-$C_{14}$ cycloalkyl, —O—$C_1$-$C_3$ alkylene-$C_3$-$C_5$ cycloalkyl, $C_1$-$C_3$ alkylene-$C_7$-$C_{14}$ cycloalkyl, —O—$C_1$-$C_3$ alkylene-heteroaryl, or heteroaryl;
  $R^{11}$ is $NR^{16}R^{18}$, fluoro, iodo, bromo, hydroxyl, $C_1$-$C_3$ alkyl, —O-aryl, $C_1$-$C_3$ alkylene-aryl, $C_1$-$C_3$ alkylene-O-aryl, —S-aryl, —O—$C_1$-$C_3$ alkylene-aryl, —NR$^{16}$—SO$_2$—NR$^{18}$—C$_1$-C$_3$ alkyl, —NR$^{16}$—SO$_2$—NR$^{18}$—C$_1$-C$_3$ haloalkyl, —NR$^{16}$—SO$_2$—C$_1$-C$_3$ alkyl, —NR$^{16}$—SO$_2$—C$_1$-C$_3$ haloalkyl, SO$_2$—NR$^{16}$R$^{18}$, SO$_2$—C$_1$-C$_3$alkyl, —O—C$_1$-C$_3$ alkyl, —C(O)—O—C$_1$-C$_3$ alkyl, —C(O)—OH, —C(O)—NR$^{16}$R$^{18}$, —C(O)—NH(C$_1$-C$_3$ haloalkyl), —C(O)—NH(C$_1$-C$_3$ alkylene-heterocycloalkyl), —C(O)—NH(heteroaryl), NH—C(O)—C$_1$-C$_3$ alkyl, NH—C(O)-heteroaryl, heterocycloalkyl, —O—C$_1$-C$_3$ alkylene-heterocycloalkyl, —O—C$_1$-C$_3$ alkylene-C$_3$-C$_{14}$ cycloalkyl, —O—C$_1$-C$_3$ alkylene-heteroaryl, or heteroaryl;

R$^{12}$ is NR$^{16}$R$^{18}$, halo, hydroxyl, C$_1$-C$_3$ alkyl, C$_1$-C$_3$ alkylene-aryl, C$_1$-C$_3$ alkylene-O-aryl, —S-aryl, —O—C$_2$-C$_3$ alkylene-aryl, —NR$^{16}$—SO$_2$—NR$^{18}$—C$_1$-C$_3$ alkyl, —NR$^{16}$—SO$_2$—NR$^{18}$—C$_1$-C$_3$ haloalkyl, —NR$^{16}$—SO$_2$—C$_1$-C$_3$ alkyl, —NR$^{16}$—SO$_2$—C$_1$-C$_3$ haloalkyl, SO$_2$—NR$^{16}$R$^{18}$, SO$_2$—C$_1$-C$_3$alkyl, —O—C$_1$-C$_3$ alkyl, —C(O)—O—C$_1$-C$_3$ alkyl, —C(O)—OH, —C(O)—NR$^{16}$R$^{18}$, —C(O)—NH(C$_1$-C$_3$ haloalkyl), —C(O)—NH(C$_1$-C$_3$ alkylene-heterocycloalkyl), —C(O)—NH(heteroaryl), NH—C(O)—C$_1$-C$_3$ alkyl, NH—C(O)-heteroaryl, heterocycloalkyl, —O—C$_1$-C$_3$ alkylene-heterocycloalkyl, —O—C$_3$-C$_{14}$ cycloalkyl, —O—C$_1$-C$_3$ alkylene-C$_3$-C$_{14}$ cycloalkyl, —O—C$_1$-C$_3$ alkylene-heteroaryl, or heteroaryl;

R$^{13}$ and R$^{14}$ are NR$^{16}$R$^{18}$, halo, hydroxyl, C$_1$-C$_3$ alkyl, —O-aryl, C$_1$-C$_3$ alkylene-aryl, C$_1$-C$_3$ alkylene-O-aryl, —S-aryl, —O—C$_1$-C$_3$ alkylene-aryl, —NR$^{16}$—SO$_2$—NR$^{18}$—C$_1$-C$_3$ alkyl, —NR$^{16}$—SO$_2$—NR$^{18}$—C$_1$-C$_3$ haloalkyl, —NR$^{16}$—SO$_2$—C$_1$-C$_3$ alkyl, —NR$^{16}$—SO$_2$—C$_1$-C$_3$ haloalkyl, SO$_2$—NR$^{16}$R$^{18}$, SO$_2$—C$_1$-C$_3$alkyl, —O—C$_1$-C$_3$ alkyl, —C(O)—O—C$_1$-C$_3$ alkyl, —C(O)—OH, —C(O)—NR$^{16}$R$^{18}$, —C(O)—NH(C$_1$-C$_3$ haloalkyl), —C(O)—NH(C$_1$-C$_3$ alkylene-heterocycloalkyl), —C(O)—NH(heteroaryl), NH—C(O)—C$_1$-C$_3$ alkyl, NH—C(O)-heteroaryl, heterocycloalkyl, —O—C$_1$-C$_3$ alkylene-heterocycloalkyl, —O—C$_3$-C$_{14}$ cycloalkyl, —O—C$_1$-C$_3$ alkylene-C$_3$-C$_{14}$ cycloalkyl, —O—C$_1$-C$_3$ alkylene-heteroaryl, or heteroaryl;

wherein 5-n of R$^{10}$, R$^{11}$, R$^{12}$, R$^{13}$, and R$^{14}$ are hydrogen, and n of R$^{10}$, R$^{11}$, R$^{12}$, R$^{13}$, and R$^{14}$ are selected from the following groups:

NR$^{16}$R$^{18}$, halo, hydroxyl, C$_1$-C$_3$ alkyl, —O-aryl, C$_1$-C$_3$ alkylene-aryl, C$_1$-C$_3$ alkylene-O-aryl, —S-aryl, —O—C$_1$-C$_3$ alkylene-aryl, —NR$^{16}$—SO$_2$—NR$^{18}$—C$_1$-C$_3$ alkyl, —NR$^{16}$—SO$_2$—NR$^{18}$—C$_1$-C$_3$ haloalkyl, —NR$^{16}$—SO$_2$—C$_1$-C$_3$ alkyl, —NR$^{16}$—SO$_2$—C$_1$-C$_3$ haloalkyl, SO$_2$—NR$^{16}$R$^{18}$, SO$_2$—C$_1$-C$_3$ alkyl, —O—C$_1$-C$_3$ alkyl, —C(O)—O—C$_1$-C$_3$ alkyl, —C(O)—OH, —C(O)—NR$^{16}$R$^{18}$, —C(O)—NH(C$_1$-C$_3$ haloalkyl), —C(O)—NH(C$_1$-C$_3$ alkylene-heterocycloalkyl), —C(O)—NH(heteroaryl), NH—C(O)—C$_1$-C$_3$ alkyl, NH—C(O)-heteroaryl, heterocycloalkyl, —O—C$_1$-C$_3$ alkylene-heterocycloalkyl, —O—C$_3$-C$_{14}$ cycloalkyl, —O—C$_1$-C$_3$ alkylene-C$_3$-C$_{14}$ cycloalkyl, —O—C$_1$-C$_3$ alkylene-heteroaryl, or heteroaryl;

wherein n is 2, 3, 4 or 5;

wherein any of said aryl groups of —O-aryl, —S-aryl, C$_1$-C$_3$ alkylene-aryl, C$_1$-C$_3$ alkylene-O-aryl; said heterocycloalkyl; said heterocycloalkyl groups of —C(O)—NH(C$_1$-C$_3$ alkylene-heterocycloalkyl) and —O—C$_1$-C$_3$ alkylene-heterocycloalkyl; said heteroaryl and said heteroaryl groups of —C(O)—NH (heteroaryl), NH—C(O)-heteroaryl, and —O—C$_1$-C$_3$ alkylene-heteroaryl; and said cycloalkyl groups of —O—C$_3$-C$_{14}$ cycloalkyl, —O—C$_1$-C$_3$ alkylene-C$_3$-C$_5$ cycloalkyl, and —O—C$_1$-C$_3$ alkylene-C$_3$-C$_{14}$ cycloalkyl may be substituted with 1 to 3 substituents selected from the group consisting of: halo, C$_1$-C$_3$ alkyl, C$_1$-C$_3$ haloalkyl, CN, and NR$^{16}$R$^{18}$; R$^4$ and R$^5$ are each independently selected from hydrogen and C$_1$-C$_4$ alkyl; R$^6$ and R$^7$ are each independently selected from hydrogen and C$_1$-C$_4$ alkyl; R$^8$ and R$^9$ are each independently selected from hydrogen and C$_1$-C$_4$ alkyl; and R$^{16}$ and R$^{18}$ are each independently selected from hydrogen and C$_1$-C$_3$ alkyl. In certain embodiments, R$^4$ and R$^5$ are hydrogen; and R$^8$ and R$^9$ are each hydrogen. In certain embodiments, R$^6$ and R$^7$ are hydrogen; R$^4$ and R$^5$ are hydrogen; and R$^8$ and R$^9$ are each hydrogen. In certain embodiments, R$^6$ and R$^7$ are hydrogen. In certain embodiments, R$^2$ is hydrogen. In certain embodiments, R$^1$ is C$_1$-C$_3$ alkyl. In certain embodiments, R$^1$ is methyl. In certain embodiments, R$^{13}$ is NR$^{16}$R$^{18}$, NR$^{16}$SO$_2$—NR$^{18}$—C$_1$-C$_3$ alkyl, —NR$^{16}$—SO$_2$—NR$^{18}$—C$_1$-C$_3$ haloalkyl, —NR$^{16}$—SO$_2$—C$_1$-C$_3$ alkyl, —NR$^{16}$—SO$_2$—C$_1$-C$_3$ haloalkyl, SO$_2$—NR$^{16}$R$^{18}$, SO$_2$—C$_1$-C$_3$alkyl, —C(O)—NR$^{16}$R$^{18}$, —C(O)—NH(C$_1$-C$_3$ haloalkyl), —C(O)—NH(C$_1$-C$_3$ alkylene-heterocycloalkyl), —C(O)—NH(heteroaryl), NH—C(O)—C$_1$-C$_3$ alkyl, or NH—C(O)-heteroaryl. In certain embodiments, R$^{13}$ is NR$^{16}$R$^{18}$, —NR$^{16}$—SO$_2$—C$_1$-C$_3$ alkyl, or —NH—SO$_2$—C$_1$-C$_3$ haloalkyl. In certain embodiments, R$^3$ is heteroaryl, 9 to 12 membered bicyclic aryl, or napthalen-1-yl. In certain embodiments, R$^3$ is indolyl, 1,3-benzodioxolyl, or benzimidazolyl. In certain embodiments, R$^3$ is X. In certain embodiments, four of R$^{10}$, R$^{11}$, R$^{12}$, R$^{13}$, and R$^{14}$ are hydrogen, and one of R$^{10}$, R$^{11}$, R$^{12}$, R$^{13}$, or R$^{14}$ are selected from the following groups: R$^{10}$ is NR$^{16}$R$^{18}$, halo, hydroxyl, C$_1$-C$_3$ alkyl, C$_1$-C$_3$ alkylene-aryl, C$_1$-C$_3$ alkylene-O-aryl, —S-aryl, —O—C$_1$-C$_3$ alkylene-aryl, —NR$^{16}$—SO$_2$—NR$^{18}$—C$_1$-C$_3$ alkyl, —NR$^{16}$—SO$_2$—NR$^{18}$—C$_1$-C$_3$ haloalkyl, —NR$^{16}$—SO$_2$—C$_1$-C$_3$ alkyl, —NR$^{16}$—SO$_2$—C$_1$-C$_3$ haloalkyl, SO$_2$—NR$^{16}$R$^{18}$, SO$_2$—C$_1$-C$_3$ alkyl, —O—C$_1$-C$_3$ alkyl, —C(O)—O—C$_1$-C$_3$ alkyl, —C(O)—OH, —C(O)—NR$^{16}$R$^{18}$, —C(O)—NH(C$_1$-C$_3$ haloalkyl), —C(O)—NH(C$_1$-C$_3$ alkylene-heterocycloalkyl), —C(O)—NH(heteroaryl), NH—C(O)—C$_1$-C$_3$ alkyl, NH—C(O)-heteroaryl, heterocycloalkyl, —O—C$_1$-C$_3$ alkylene-heterocycloalkyl, —O—C$_3$-C$_5$ cycloalkyl, —O—C$_3$-C$_5$ cycloalkyl, —O—C$_3$-C$_5$ cycloalkyl, —O—C$_3$-C$_5$ cycloalkyl, —O—C$_3$-C$_5$ cycloalkyl, —O—C$_1$-C$_3$ alkylene-C$_3$-C$_5$ cycloalkyl, C$_1$-C$_3$ alkylene-C$_2$-C$_{14}$ cycloalkyl, —O—C$_1$-C$_3$ alkylene-heteroaryl, or heteroaryl; R$^{11}$ is NR$^{16}$R$^{18}$, fluoro, iodo, bromo, hydroxyl, C$_1$-C$_3$ alkyl, —O-aryl, C$_1$-C$_3$ alkylene-aryl, C$_1$-C$_3$ alkylene-O-aryl, —S-aryl, —O—C$_1$-C$_3$ alkylene-aryl, —NR$^{16}$—SO$_2$—NR$^{18}$—C$_1$-C$_3$ alkyl, —NR$^{16}$—SO$_2$—NR$^{18}$—C$_1$-C$_3$ haloalkyl, —NR$^{16}$—SO$_2$—C$_1$-C$_3$ alkyl, —NR$^{16}$—SO$_2$—C$_1$-C$_3$ haloalkyl, SO$_2$—NR$^{16}$R$^{18}$, SO$_2$—C$_1$-C$_3$ alkyl, —O—C$_1$-C$_3$ alkyl, —C(O)—O—C$_1$-C$_3$ alkyl, —C(O)—OH, —C(O)—NR$^{16}$R$^{18}$, —C(O)—NH(C$_1$-C$_3$ haloalkyl), —C(O)—NH(C$_1$-C$_3$ alkylene-heterocycloalkyl), —C(O)—NH(heteroaryl), NH—C(O)—C$_1$-C$_3$ alkyl, NH—C(O)-heteroaryl, heterocycloalkyl, —O—C$_1$-C$_3$ alkylene-heterocycloalkyl, —O—C$_1$-C$_3$ alkylene-C$_3$-C$_{14}$ cycloalkyl, —O—C$_1$-C$_3$ alkylene-heteroaryl, or heteroaryl; $R^{12}$ is $NR^{16}R^{18}$, halo, hydroxyl, $C_1$-$C_3$ alkyl, $C_1$-$C_3$ alkylene-aryl, $C_1$-$C_3$ alkylene-O-aryl, —S-aryl, —O—$C_2$-$C_3$ alkylene-aryl, —$NR^{16}$—$SO_2$—$NR^{18}$—$C_1$-$C_3$ alkyl, —$NR^{16}$—$SO_2$—$NR^{18}$—$C_1$-$C_3$ haloalkyl, —$NR^{16}$—$SO_2$—$C_1$-$C_3$ alkyl, —$NR^{16}$—$SO_2$—$C_1$-$C_3$ haloalkyl, $SO_2$—$NR^{16}R^{18}$, $SO_2$—$C_1$-$C_3$alkyl, —O—$C_1$-$C_3$ alkyl, —C(O)—O—$C_1$-$C_3$ alkyl, —C(O)—OH, —C(O)—$NR^{16}R^{18}$, —C(O)—NH($C_1$-$C_3$ haloalkyl), —C(O)—NH($C_1$-$C_3$ alkylene-heterocycloalkyl), —C(O)—NH(heteroaryl), NH—C(O)—$C_1$-$C_3$ alkyl, NH—C(O)-heteroaryl, heterocycloalkyl, —O—$C_1$-$C_3$ alkylene-heterocycloalkyl, —O—$C_3$-$C_{14}$ cycloalkyl, —O—$C_1$-$C_3$ alkylene-$C_3$-$C_{14}$ cycloalkyl, —O—$C_1$-$C_3$ alkylene-heteroaryl, or heteroaryl; $R^{13}$ and $R^{14}$ are $NR^{16}R^{18}$, halo, hydroxyl, $C_1$-$C_3$ alkyl, —O-aryl, $C_1$-$C_3$ alkylene-aryl, $C_1$-$C_3$ alkylene-O-aryl, —S-aryl, —O—$C_1$-$C_3$ alkylene-aryl, —$NR^{16}$—$SO_2$—$NR^{18}$—$C_1$-$C_3$ alkyl, —$NR^{16}$—$SO_2$—$NR^{18}$—$C_1$-$C_3$ haloalkyl, —$NR^{16}$—$SO_2$—$C_1$-$C_3$ alkyl, —$NR^{16}$—$SO_2$—$C_1$-$C_3$ haloalkyl, $SO_2$—$NR^{16}R^{18}$, $SO_2$—$C_1$-$C_3$alkyl, —O—$C_1$-$C_3$ alkyl, —C(O)—O—$C_1$-$C_3$ alkyl, —C(O)—OH, —C(O)—$NR^{16}R^{18}$, —C(O)—NH($C_1$-$C_3$ haloalkyl), —C(O)—NH($C_1$-$C_3$ alkylene-heterocycloalkyl), —C(O)—NH(heteroaryl), —C(O)—$C_1$-$C_3$ alkyl, NH—C(O)-heteroaryl, heterocycloalkyl, —O—$C_1$-$C_3$ alkylene-heterocycloalkyl, —O—$C_3$-$C_{14}$ cycloalkyl, —O—$C_1$-$C_3$ alkylene-$C_3$-$C_{14}$ cycloalkyl, —O—$C_1$-$C_3$ alkylene-heteroaryl, or heteroaryl; and wherein any of said aryl groups of —O-aryl, —S-aryl, $C_1$-$C_3$ alkylene-aryl, $C_1$-$C_3$ alkylene-O-aryl; said heterocycloalkyl; said heterocycloalkyl groups of —C(O)—NH($C_1$-$C_3$ alkylene-heterocycloalkyl) and —O—$C_1$-$C_3$ alkylene-heterocycloalkyl; said heteroaryl and said heteroaryl groups of —C(O)—NH(heteroaryl), NH—C(O)-heteroaryl, and —O—$C_1$-$C_3$ alkylene-heteroaryl; and said cycloalkyl groups of —O—$C_3$-$C_{14}$ cycloalkyl, —O—$C_1$-$C_3$ alkylene-$C_3$-$C_5$ cycloalkyl, and —O—$C_1$-$C_3$ alkylene-$C_3$-$C_{14}$ cycloalkyl may be substituted with 1 to 3 substituents selected from the group consisting of: halo, $C_1$-$C_3$ alkyl, $C_1$-$C_3$ haloalkyl, CN, and $NR^{16}R^{18}$. In certain embodiments, 5-n of $R^{10}$, $R^{11}$, $R^{12}$, $R^{13}$, and $R^{14}$ are hydrogen, and n of $R^{10}$, $R^{11}$, $R^{12}$, $R^{13}$, and $R^{14}$ are selected from the following groups: $NR^{16}R^{18}$, halo, hydroxyl, $C_1$-$C_3$ alkyl, —O-aryl, $C_1$-$C_3$ alkylene-aryl, $C_1$-$C_3$ alkylene-O-aryl, —S-aryl, —O—$C_1$-$C_3$ alkylene-aryl, —$NR^{16}$—$SO_2$—$NR^{18}$—$C_1$-$C_3$ alkyl, —$NR^{16}$—$SO_2$—$NR^{18}$—$C_1$-$C_3$ haloalkyl, —$NR^{16}$—$SO_2$—$C_1$-$C_3$ alkyl, —$NR^{16}$—$SO_2$—$C_1$-$C_3$ haloalkyl, $SO_2$—$NR^{16}R^{18}$, $SO_2$—$C_1$-$C_3$alkyl, —O—$C_1$-$C_3$ alkyl, —C(O)—O—$C_1$-$C_3$ alkyl, —C(O)—OH, —C(O)—$NR^{16}R^{18}$, —C(O)—NH($C_1$-$C_3$ haloalkyl), —C(O)—NH($C_1$-$C_3$ alkylene-heterocycloalkyl), —C(O)—NH(heteroaryl), NH—C(O)—$C_1$-$C_3$ alkyl, NH—C(O)-heteroaryl, heterocycloalkyl, —O—$C_1$-$C_3$ alkylene-heterocycloalkyl, —O—$C_3$-$C_{14}$ cycloalkyl, —O—$C_1$-$C_3$ alkylene-$C_3$-$C_{14}$ cycloalkyl, —O—$C_1$-$C_3$ alkylene-heteroaryl, or heteroaryl; wherein n is 2, 3, 4 or 5; wherein any of said aryl groups of —O-aryl, —S-aryl, $C_1$-$C_3$ alkylene-aryl, $C_1$-$C_3$ alkylene-O-aryl; said heterocycloalkyl; said heterocycloalkyl groups of —C(O)—NH($C_1$-$C_3$ alkylene-heterocycloalkyl) and —O—$C_1$-$C_3$ alkylene-heterocycloalkyl; said heteroaryl and said heteroaryl groups of —C(O)—NH(heteroaryl), NH—C(O)-heteroaryl, and —O—$C_1$-$C_3$ alkylene-heteroaryl; and said cycloalkyl groups of —O—$C_3$-$C_{14}$ cycloalkyl, —O—$C_1$-$C_3$ alkylene-$C_3$-$C_5$ cycloalkyl, and —O—$C_1$-$C_3$ alkylene-$C_3$-$C_{14}$ cycloalkyl may be substituted with 1 to 3 substituents selected from the group consisting of: halo, $C_1$-$C_3$ alkyl, $C_1$-$C_3$ haloalkyl, CN, and $NR^{16}R^{18}$. In certain embodiments, n is 3. In certain embodiments, n is 2. In certain embodiments, $R^{13}$ is $NR^{16}R^{18}$, —$NR^{16}$—$SO_2$—$NR^{18}$—$C_1$-$C_3$ alkyl, —$NR^{16}$—$SO_2$—$NR^{18}$—$C_1$-$C_3$ haloalkyl, —$NR^{16}$—$SO_2$—$C_1$-$C_3$ alkyl, —$NR^{16}$—$SO_2$—$C_1$-$C_3$ haloalkyl, $SO_2$—$NR^{16}R^{18}$, $SO_2$—$C_1$-$C_3$alkyl, —C(O)—$NR^{16}R^{18}$, —C(O)—NH($C_1$-$C_3$ haloalkyl), —C(O)—NH($C_1$-$C_3$ alkylene-heterocycloalkyl), —C(O)—NH(heteroaryl), NH—C(O)—$C_1$-$C_3$ alkyl, or NH—C(O)-heteroaryl. In certain embodiments, $R^{16}$ is H and $R^{18}$ is $C_1$-$C_3$ alkyl. In certain embodiments, $R^{18}$ is H and $R^{16}$ is $C_1$-$C_3$ alkyl. In certain embodiments, $R^{16}$ is H and $R^{18}$ is H. In certain embodiments, $R^{16}$ is $C_1$-$C_3$ alkyl and $R^{18}$ is $C_1$-$C_3$ alkyl. In certain embodiments, $R^{13}$ is $NR^{16}R^{18}$, and $R^{16}$ is hydrogen and $R^{18}$ is hydrogen. In certain embodiments, $R^{13}$ is —$NR^{16}$—$SO_2$—$C_1$-$C_3$ alkyl and $R^{16}$ is hydrogen. In certain embodiments, $R^{13}$ is —$NR^{16}$—$SO_2$—$C_1$-$C_3$ haloalkyl, and $R^{16}$ is hydrogen. In certain embodiments, $R^{13}$ is $NR^{16}R^{18}$, —$NR^{16}$—$SO_2$—$C_1$-$C_3$ alkyl, or —NH—$SO_2$—$C_1$-$C_3$ haloalkyl. In certain embodiments, $R^{10}$ is O-aryl. In certain embodiments, $R^{10}$ is O-phenyl or is O-phenyl which is substituted with 1 to 3 independently groups independently selected from the group consisting of halo. In certain embodiments, $R^{10}$ is —O-2,4-difluoro-phenyl. In certain embodiments, $R^{10}$ is —O—$C_1$-$C_3$ alkylene-$C_3$-$C_{14}$ cycloalkyl, which may be substituted with 1 to 3 groups independently selected from the group consisting of halo and $C_1$-$C_3$ alkyl. In certain embodiments, $R^{10}$ is —O—$C_1$-$C_3$ alkylene-$C_3$-$C_{14}$ cycloalkyl, which is substituted with 1 to 3 groups independently selected from the group consisting of halo and $C_1$-$C_3$ alkyl. In certain embodiments, $R^{10}$ is —O—$C_1$-$C_3$ alkylene-$C_3$-$C_{14}$ cycloalkyl, which is substituted with 1 to 3 groups independently selected from the group consisting of halo. In certain embodiments, n is 2 and $R^{11}$, $R^{12}$, and $R^{14}$ are hydrogen. In certain embodiments, a compound of formula I is selected from the group consisting of:

3-methyl-1-phenyl-2,5,6,7-tetrahydro-4H-isoindol-4-one;
3-methyl-1-(2-phenoxyphenyl)-2,5,6,7-tetrahydro-4H-isoindol-4-one;
1-(2-aminophenyl)-3-methyl-2,5,6,7-tetrahydro-4H-isoindol-4-one;
3-methyl-1-(4-methylphenyl)-2,5,6,7-tetrahydro-4H-isoindol-4-one;
4-(3-methyl-4-oxo-4,5,6,7-tetrahydro-2H-isoindol-1-yl)benzenesulfonamide;
1-(2-methoxyphenyl)-3-methyl-2,5,6,7-tetrahydro-4H-isoindol-4-one;
3-methyl-1-(3,4,5-trimethoxyphenyl)-2,5,6,7-tetrahydro-4H-isoindol-4-one;
3-methyl-1-[4-(methylsulfonyl)phenyl]-2,5,6,7-tetrahydro-4H-isoindol-4-one;
3-(3-methyl-4-oxo-4,5,6,7-tetrahydro-2H-isoindol-1-yl)benzamide;
1-(1H-indol-4-yl)-3-methyl-2,5,6,7-tetrahydro-4H-isoindol-4-one;
1-(4-methoxyphenyl)-3-methyl-2,5,6,7-tetrahydro-4H-isoindol-4-one;
1-(3,4-dimethylphenyl)-3-methyl-2,5,6,7-tetrahydro-4H-isoindol-4-one;

1-(4-chlorophenyl)-3-methyl-2,5,6,7-tetrahydro-4H-isoindol-4-one;
1-[3-(benzyloxy)phenyl]-3-methyl-2,5,6,7-tetrahydro-4H-isoindol-4-one;
1-(2-chlorophenyl)-3-methyl-2,5,6,7-tetrahydro-4H-isoindol-4-one;
1-(3,5-dimethylphenyl)-3-methyl-2,5,6,7-tetrahydro-4H-isoindol-4-one;
1-(3-methoxyphenyl)-3-methyl-2,5,6,7-tetrahydro-4H-isoindol-4-one;
3-methyl-1-(2-{[3-(trifluoromethyl)phenoxy]methyl}phenyl)-2,5,6,7-tetrahydro-4H-isoindol-4-one;
3-methyl-1-[2-(phenoxymethyl)phenyl]-2,5,6,7-tetrahydro-4H-isoindol-4-one;
3-methyl-1-{2-[(2-methylphenoxy)methyl]phenyl}-2,5,6,7-tetrahydro-4H-isoindol-4-one;
1-[2-(furan-2-yl)phenyl]-3-methyl-2,5,6,7-tetrahydro-4H-isoindol-4-one;
1-(2-hydroxyphenyl)-3-methyl-2,5,6,7-tetrahydro-4H-isoindol-4-one;
3-methyl-1-[2-(tetrahydrofuran-3-ylmethoxy)phenyl]-2,5,6,7-tetrahydro-4H-isoindol-4-one;
1-[2-(cyclopentylmethoxy)phenyl]-3-methyl-2,5,6,7-tetrahydro-4H-isoindol-4-one;
3-methyl-1-[2-(tetrahydrofuran-2-ylmethoxy)phenyl]-2,5,6,7-tetrahydro-4H-isoindol-4-one;
3-methyl-1-[2-(tetrahydro-2H-pyran-4-ylmethoxy)phenyl]-2,5,6,7-tetrahydro-4H-isoindol-4-one;
3-methyl-1-{2-[2-(morpholin-4-yl)ethoxy]phenyl}-2,5,6,7-tetrahydro-4H-isoindol-4-one;
3-methyl-1-[2-(pyridin-2-ylmethoxy)phenyl]-2,5,6,7-tetrahydro-4H-isoindol-4-one;
3-methyl-1-[2-(quinolin-8-ylmethoxy)phenyl]-2,5,6,7-tetrahydro-4H-isoindol-4-one;
1-[2-(1-benzothiophen-7-ylmethoxy)phenyl]-3-methyl-2,5,6,7-tetrahydro-4H-isoindol-4-one;
3-methyl-1-[2-(pyridin-3-ylmethoxy)phenyl]-2,5,6,7-tetrahydro-4H-isoindol-4-one;
1-[2-(1H-indazol-5-ylmethoxy)phenyl]-3-methyl-2,5,6,7-tetrahydro-4H-isoindol-4-one;
1-(5-amino-2-phenoxyphenyl)-3-methyl-2,5,6,7-tetrahydro-4H-isoindol-4-one;
N-[3-(3-methyl-4-oxo-4,5,6,7-tetrahydro-2H-isoindol-1-yl)-4-phenoxyphenyl]methanesulfonamide;
N-[3-(2,3-dimethyl-4-oxo-4,5,6,7-tetrahydro-2H-isoindol-1-yl)-4-phenoxyphenyl]methanesulfonamide;
N-[3-(2,3-dimethyl-4-oxo-4,5,6,7-tetrahydro-2H-isoindol-1-yl)-4-phenoxyphenyl]acetamide;
1-[5-amino-2-(phenylsulfanyl)phenyl]-3-methyl-2,5,6,7-tetrahydro-4H-isoindol-4-one;
N-[3-(3-methyl-4-oxo-4,5,6,7-tetrahydro-2H-isoindol-1-yl)-4-(phenylsulfanyl)phenyl]methanesulfonamide;
1-[5-amino-2-(2,4-difluorophenoxy)phenyl]-3-methyl-2,5,6,7-tetrahydro-4H-isoindol-4-one;
N-[4-(2,4-difluorophenoxy)-3-(3-methyl-4-oxo-4,5,6,7-tetrahydro-2H-isoindol-1-yl)phenyl]methanesulfonamide;
N-[4-(2,4-difluorophenoxy)-3-(3-methyl-4-oxo-4,5,6,7-tetrahydro-2H-isoindol-1-yl)phenyl]ethanesulfonamide;
N-[4-(2,4-difluorophenoxy)-3-(3-methyl-4-oxo-4,5,6,7-tetrahydro-2H-isoindol-1-yl)phenyl]-2,2,2-trifluoroethanesulfonamide;
N'-[4-(2,4-difluorophenoxy)-3-(3-methyl-4-oxo-4,5,6,7-tetrahydro-2H-isoindol-1-yl)phenyl]-N,N-dimethylsulfuric diamide;
N-[4-(2,4-difluorophenoxy)-3-(3-methyl-4-oxo-4,5,6,7-tetrahydro-2H-isoindol-1-yl)phenyl]acetamide;
N-[4-(2,4-difluorophenoxy)-3-(3-methyl-4-oxo-4,5,6,7-tetrahydro-2H-isoindol-1-yl)phenyl]-1H-pyrrole-2-carboxamide;
N-{4-[(4,4-difluorocyclohexyl)oxy]-3-(3-methyl-4-oxo-4,5,6,7-tetrahydro-2H-isoindol-1-yl)phenyl}ethanesulfonamide;
methyl 3-(3-methyl-4-oxo-4,5,6,7-tetrahydro-2H-isoindol-1-yl)-4-phenoxybenzoate;
3-(3-methyl-4-oxo-4,5,6,7-tetrahydro-2H-isoindol-1-yl)-4-phenoxybenzoic acid;
N-ethyl-3-(3-methyl-4-oxo-4,5,6,7-tetrahydro-2H-isoindol-1-yl)-4-phenoxybenzamide;
3-(3-methyl-4-oxo-4,5,6,7-tetrahydro-2H-isoindol-1-yl)-4-phenoxy-N-(tetrahydrofuran-2-ylmethyl)benzamide;
3-(3-methyl-4-oxo-4,5,6,7-tetrahydro-2H-isoindol-1-yl)-4-phenoxy-N-(1,3-thiazol-2-yl)benzamide;
3,6,6-trimethyl-1-phenyl-2,5,6,7-tetrahydro-4H-isoindol-4-one;
1-(2,5-dimethylphenyl)-3,6,6-trimethyl-2,5,6,7-tetrahydro-4H-isoindol-4-one;
3,6,6-trimethyl-1-[2-(morpholin-4-yl)phenyl]-2,5,6,7-tetrahydro-4H-isoindol-4-one;
1-[2-(benzyloxy)phenyl]-3,6,6-trimethyl-2,5,6,7-tetrahydro-4H-isoindol-4-one;
3,6,6-trimethyl-1-(2-phenoxyphenyl)-2,5,6,7-tetrahydro-4H-isoindol-4-one;
N-[3-(3,6,6-trimethyl-4-oxo-4,5,6,7-tetrahydro-2H-isoindol-1-yl)phenyl]methanesulfonamide;
3,6-dimethyl-1-(2-phenoxyphenyl)-2,5,6,7-tetrahydro-4H-isoindol-4-one;
1-(5-amino-2-phenoxyphenyl)-3,6-dimethyl-2,5,6,7-tetrahydro-4H-isoindol-4-one;
N-[3-(3,6-dimethyl-4-oxo-4,5,6,7-tetrahydro-2H-isoindol-1-yl)-4-phenoxyphenyl]methanesulfonamide;
3-methyl-6-(2-methylpropyl)-1-(2-phenoxyphenyl)-2,5,6,7-tetrahydro-4H-isoindol-4-one;
N-{3-[3-methyl-6-(2-methylpropyl)-4-oxo-4,5,6,7-tetrahydro-2H-isoindol-1-yl]-4-phenoxyphenyl}methanesulfonamide;
3-methyl-1-(2-phenoxyphenyl)-6-(propan-2-yl)-2,5,6,7-tetrahydro-4H-isoindol-4-one;
N-{3-[3-methyl-4-oxo-6-(propan-2-yl)-4,5,6,7-tetrahydro-2H-isoindol-1-yl]-4-phenoxyphenyl}methanesulfonamide;
N-[3-(3-methyl-4-oxo-6-phenyl-4,5,6,7-tetrahydro-2H-isoindol-1-yl)-4-phenoxyphenyl]methanesulfonamide; and
1-[2-(cyclopropylmethoxy)-5-(methylsulfonyl)phenyl]-3-methyl-2,5,6,7-tetrahydro-4H-isoindol-4-one.

In certain embodiments, a compound of formula I is selected from the group consisting of:
1-(1,3-benzodioxol-5-yl)-3-methyl-2,5,6,7-tetrahydro-4H-isoindol-4-one;
1-[2-(benzyloxy)phenyl]-3-methyl-2,5,6,7-tetrahydro-4H-isoindol-4-one;
3-methyl-1-(naphthalen-1-yl)-2,5,6,7-tetrahydro-4H-isoindol-4-one;
1-(1H-benzimidazol-4-yl)-3-methyl-2,5,6,7-tetrahydro-4H-isoindol-4-one;
1-(1H-indol-7-yl)-3-methyl-2,5,6,7-tetrahydro-4H-isoindol-4-one;
2-[2-(3-methyl-4-oxo-4,5,6,7-tetrahydro-2H-isoindol-1-yl)benzyl]-1H-isoindole-1,3(2H)-dione; and
1-(1,3-benzodioxol-5-yl)-3,6,6-trimethyl-2,5,6,7-tetrahydro-4H-isoindol-4-one.

In another aspect, the present invention relates to pharmaceutical compositions comprising a pharmaceutically acceptable excipient and a therapeutically effective amount of a compound of formula I, or a pharmaceutically acceptable salt thereof.

In another aspect, the present invention relates to methods of treating cancer in a subject comprising administering a therapeutically effective amount of a compound of formula (I), or a pharmaceutically acceptable salt thereof, to a subject in need thereof. In certain embodiments, the cancer is selected from the group consisting of: acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenström's macroglobulinemia, testicular tumors, uterine cancer and Wilms' tumor. In certain embodiments, the methods further comprise administering a therapeutically effective amount of at least one additional therapeutic agent.

In another aspect, the present invention relates to methods of treating a disease or condition in a subject comprising administering a therapeutically effective amount of a compound of formula (I), or a pharmaceutically acceptable salt thereof, to a subject in need thereof, wherein said disease or condition is selected from the group consisting of: Addison's disease, acute gout, ankylosing spondylitis, asthma, atherosclerosis, Behcet's disease, bullous skin diseases, chronic obstructive pulmonary disease (COPD), Crohn's disease, dermatitis, eczema, giant cell arteritis, glomerulonephritis, hepatitis, hypophysitis, inflammatory bowel disease, Kawasaki disease, lupus nephritis, multiple sclerosis, myocarditis, myositis, nephritis, organ transplant rejection, osteoarthritis, pancreatitis, pericarditis, Polyarteritis nodosa, pneumonitis, primary biliary cirrhosis, psoriasis, psoriatic arthritis, rheumatoid arthritis, scleritis, sclerosing cholangitis, sepsis, systemic lupus erythematosus, Takayasu's Arteritis, toxic shock, thyroiditis, type I diabetes, ulcerative colitis, uveitis, vitiligo, vasculitis, and Wegener's granulomatosis. In certain embodiments, the methods further comprise administering a therapeutically effective amount of at least one additional therapeutic agent. In certain embodiments, the methods further comprise administering a therapeutically effective amount of at least one additional therapeutic agent.

In another aspect, the present invention relates to methods of treating AIDS in a subject comprising administering a therapeutically effective amount of a compound of formula (I), or a pharmaceutically acceptable salt thereof, to a subject in need thereof. In certain embodiments, the methods further comprise administering a therapeutically effective amount of at least one additional therapeutic agent.

In another aspect, the present invention relates to methods of treating obesity in a subject comprising administering a therapeutically effective amount of a compound of formula (I), or a pharmaceutically acceptable salt thereof, to a subject in need thereof. In certain embodiments, the methods further comprise administering a therapeutically effective amount of at least one additional therapeutic agent.

In another aspect, the present invention relates to methods of treating type II diabetes in a subject comprising administering a therapeutically effective amount of a compound of formula (I), or a pharmaceutically acceptable salt thereof, to a subject in need thereof. In certain embodiments, the methods further comprise administering a therapeutically effective amount of at least one additional therapeutic agent.

DETAILED DESCRIPTION

Definitions

It is noted that, as used in this specification and the intended claims, the singular form "a," "an," and "the" include plural referents unless the context clearly dictates otherwise. Thus, for example, reference to "a compound" includes a single compound as well as one or more of the same or different compounds, reference to "optionally a pharmaceutically acceptable carrier" refers to a single optional pharmaceutically acceptable carrier as well as one or more pharmaceutically acceptable carriers, and the like.

As used in the specification and the appended claims, unless specified to the contrary, the following terms have the meaning indicated:

The term "alkyl" as used herein, means a saturated, straight or branched hydrocarbon chain radical. In some instances, the number of carbon atoms in an alkyl moiety is indicated by the prefix "$C_x$-$C_y$", wherein x is the minimum and y is the maximum number of carbon atoms in the substituent. Thus, for example, "$C_1$-$C_6$ alkyl" refers to an alkyl substituent containing from 1 to 6 carbon atoms and "$C_1$-$C_3$ alkyl" refers to an alkyl substituent containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 1-methylbutyl, 2-methylbutyl, 3-methylbutyl, 1,1-dimethylpropyl, 1,2-dimethylpropyl, 2,2-dimethylpropyl, 1-methylpropyl, 1-ethylpropyl, 1,2,2-trimethylpropyl, 3-methylhexyl, 2,2-dimethylpentyl, 2,3-dimethylpentyl, n-heptyl, n-octyl, n-nonyl, and n-decyl.

The term "alkylene" or "alkylenyl" means a divalent radical derived from a straight or branched, saturated hydrocarbon chain, for example, of 1 to 10 carbon atoms or of 1 to 6 carbon atoms ($C_1$-$C_6$ alkylene) or of 1 to 4 carbon atoms or of 1 to 3 carbon atoms ($C_1$-$C_3$ alkylene). Examples of alkylene and alkylenyl include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "C$_3$-C$_{14}$ cycloalkyl" (alone or in combination with another term(s)) means a saturated cyclic hydrocarbyl substituent containing from 3 to 14 carbon ring atoms. The term cycloalkyl includes monocyclic cycloalkyl, bicyclic cycloalkyl, bridged cycloalkyl, and spiro cycloalkyl groups. Examples of monocyclic cycloalkyl groups include, but are not limited to, cyclopropyl (cyclopropanyl), cyclobutyl (cyclobutanyl), cyclopentyl (cyclopentanyl), cyclopentenyl, cyclopentadienyl, cyclohexyl (cyclohexanyl), cyclohexenyl, cycloheptyl, cyclooctyl, etc. Unless otherwise indicated, the term "C$_3$-C$_8$ monocyclic cycloalkyl" refers to monocylic cycloalkyl groups containing from 3 to 8 carbons.

In a spirocyclic cycloalkyl group, one atom is common to two different rings. Examples of spirocyclic cycloalkyls include spiro[2.2]pentanyl, spiro[2.4]heptanyl, and spiro[2.5]octanyl. Unless otherwise indicated, the term "C$_5$-C$_8$ spirocyclic cycloalkyl" refers to spirocyclic cycloalkyl groups containing from 5 to 8 carbons.

In a bridged cycloalkyl, the rings share at least two common non-adjacent atoms. Examples of bridged cycloalkyls include bicyclo[2.2.1]heptanyl, and adamantanyl. Unless otherwise indicated, the term "C$_7$-C$_{10}$ bridged cycloalkyl" refers to a bridged cycloalkyl groups containing from 5 to 10 carbons.

A bicyclic ring cycloalkyl is a C$_5$-C$_7$ monocyclic cycloalkyl fused to a monocyclic C$_5$-C$_7$ cycloalkyl ring. Non-limiting examples of bicyclic cycloalkyls include decahydronaphthalenyl, octahydro-1H-indenyl, octahydropentalenyl, and decahydroazulenyl. The bicyclic cycloalkyl groups may contain one or two alkylene bridges, each consisting of one, two, three, or four carbon atoms in length, and each bridge links two non-adjacent carbon atoms of the ring system. Non-limiting examples of bicyclic bridged groups include bicyclo[3.1.1]heptanyl, bicyclo[2.2.1]heptanyl, bicyclo[2.2.2]octanyl, bicyclo[3.2.2]nonanyl, bicyclo[3.3.1]nonanyl, and bicyclo[4.2.1]nonanyl, tricyclo[3.3.1.0$^{3,7}$]nonanyl (octahydro-2,5-methanopentalenyl or noradamantanyl), and tricyclo[3.3.1.1$^{3,7}$]decanyl (adamantanyl).

The term "cycloalkenyl" (alone or in combination with another term(s)) means a partially saturated cycloalkyl substituent containing from 3 to 14 carbon ring atoms. A cycloalkenyl may be a monocyclic carbon ring, which typically contains from 3 to 8 carbon ring atoms (i.e., a C$_3$-C$_8$ cycloalkenyl) and more typically from 4 to 6 carbon ring atoms (i.e., a C$_4$-C$_6$ cycloalkenyl). Examples of single-ring cycloalkenyls include cyclopentenyl, and cyclohexenyl. A cycloalkenyl may alternatively be bicyclic. Examples of bicyclic cycloalkenyls include bridged and spirocyclic cycloalkyls.

The term "heterocycloalkyl" as used herein, means a 3 to 15 membered non-aromatic monocylic or bicyclic ring radical containing carbon atoms and one to three heteroatoms independently selected from O, N, or S. The nitrogen and sulfur heteroatoms in the heterocycloalkyl rings may optionally be oxidized (e.g. 1,1-dioxidotetrahydrothienyl, 1,2-dioxido-1,2-thiazolidinyl, 1,1-dioxidothiomorpholinyl)) and the nitrogen atoms may optionally be quarternized. Unless otherwise indicated, the foregoing heterocycloalkyls can be C-attached or N-attached where such is possible and which results in the creation of a stable structure. For example, piperidinyl can be piperidin-1-yl (N-attached) or piperidin-4-yl (C-attached). Examples of heterocycloalkyls include 3- to 8-membered monocyclic heterocycloalkyls, 8-12 membered bicyclic heterocycloalkyls, and 7-15 membered bridged bicyclic heterocycloalkyls.

The phrase "3- to 8-membered monocyclic heterocycloalkyl" means a non-aromatic cyclic group having carbon atoms and 1 to 3 heteroatoms independently selected from S, N or O, wherein when two O atoms or one O atom and one S atom are present, the two O atoms or one O atom and one S atom are not bonded to each other, respectively. Illustrative examples of 3- to 8-membered monocyclic heterocycloalkyl include aziridin-1-yl, 1-oxa-cyclobutan-2-yl, tetrahydrofuran-3-yl, morpholin-4-yl, 2-thiacyclohex-1-yl, 2-oxo-2-thiacyclohex-1-yl, 2,2-dioxo-2-thiacyclohex-1-yl, and 4-methyl-piperazin-2-yl.

A "3-membered monocyclic heterocycloalkyl" is a 3-membered, monocyclic cycloalkyl ring having 2 carbon atoms and 1 heteroatom selected from the group consisting of: 1 O; 1 S; and 1 N. Illustrative examples of 3-membered monocyclic heterocycloalkyls include oxiranyl, aziridinyl, and thiiranyl.

A "4-membered monocyclic heterocycloalkyl" is a 4-membered, monocyclic cycloalkyl ring having 3 carbon atoms and 1 heteroatom selected from the group consisting of: 1 O; 1 S; and 1 N. Illustrative examples of 4-membered monocyclic heterocycloalkyls include oxetanyl, azetidinyl, and thietanyl.

A "5-membered monocyclic heterocycloalkyl" is a 5-membered, monocyclic cycloalkyl ring having from 1 to 4 carbon atoms and from 1 to 3 heteroatoms selected from the group consisting of: 1 O; 1 S; 1 N; 2 N; 3 N; 1 S and 1 N; 1 S, and 2 N; 1 O and 1 N; and 1 O and 2 N. Illustrative examples of 5-membered monocyclic heterocycloalkyls include tetrahydrofuranyl, dihydrofuranyl, tetrahydrothienyl, dihydrothienyl, imidazolidinyl, oxazolidinyl, imidazolinyl, isoxazolidinyl, pyrrolidinyl, 2-pyrrolinyl, and 3-pyrrolinyl.

A "6-membered monocyclic heterocycloalkyl" is a 6-membered, monocyclic cycloalkyl ring having from 3 to 5 carbon atoms and from 1 to 3 heteroatoms selected from the group consisting of: 1 O; 2 O; 3 O; 1 S; 2 S; 3 S; 1 N; 2 N; 3 N; 1 S, 1 O, and 1 N; 1 S and 1 N; 1 S and 2 N; 1 S and 1 O; 1 S and 2 O; 1 O and 1 N; and 1 O and 2 N. Illustrative examples of 6-membered monocyclic heterocycloalkyls include tetrahydropyranyl, dihydropyranyl, dioxanyl, 1,3-dioxolanyl, 1,4-dithianyl, hexahydropyrimidine, morpholinyl, piperazinyl, piperidinyl, 2H-pyranyl, 4H-pyranyl, pyrazolidinyl, pyrazolinyl, 1,2,3,6-tetrahydropyridinyl, tetrahydrothiopyranyl, thiomorpholinyl, thioxanyl, and trithianyl.

A "7-membered monocyclic heterocycloalkyl" is a 7-membered, monocyclic cycloalkyl ring having from 5 or 6 carbon atoms and from 1 to 3 heteroatoms selected from the group consisting of: 1 O; 2 O; 1 S; 2 S; 1 N; 2 N; 1 S, 1 O, and 1 N; 1 S and 1 N; 1 S and 2 N; 1 S and 1 O; 1 S and 2 O; 1 O and 1 N; and 1 O and 2 N. Illustrative examples of 7-membered monocyclic heterocycloalkyls include azepanyl, 2,3,4,5-tetrahydro-1H-azepinyl, oxepanyl, 2,3,4,5-tetrahydro-1H-oxepinyl, thiepanyl, and 2,3,4,5-tetrahydro-1H-thiepinyl.

An "8-membered monocyclic heterocycloalkyl" is a 8-membered, monocyclic cycloalkyl ring having from 5 to 7 carbon atoms and from 1 to 3 heteroatoms selected from the group consisting of: 1 O; 2 O; 3 O; 1 S; 2 S; 3 S; 1 N; 2 N; 3 N; 1 S, 1 O, and 1 N; 1 S and 1 N; 1 S and 2 N; 1 S and 1 O; 1 S and 2 O; 1 O and 1 N; and 1 O and 2 N. Illustrative examples of 8-membered monocyclic heterocycloalkyls include azocanyl, thiocanyl, oxocanyl, 3,4,5,6-tetrahydro-2H-oxocinyl, etc.

A bicyclic 8-12 membered heterocycloalkyl is a monocyclic 5 to 7 membered heterocycloalkyl fused to a phenyl group, or a monocyclic 5 to 7 membered heterocycloalkyl fused to a monocyclic $C_5$-$C_7$ cycloalkyl, or a monocyclic 5 to 7 membered heterocycloalkyl fused to a monocyclic 5 to 7 membered heterocycloalkyl. Representative examples of bicyclic heterocycloalkyls include, but are not limited to, benzopyranyl, benzothiopyranyl, 2,3-dihydrobenzofuranyl, 2,3-dihydrobenzothienyl, 2,3-dihydro-1H-indolyl, 3,4-dihydroisoquinolin-2(1H)-yl, 2,3,4,6-tetrahydro-1H-pyrido[1,2-a]pyrazin-2-yl, hexahydropyrano[3,4-b][1,4]oxazin-1(5H)-yl.

The monocyclic heterocycloalkyl and the bicyclic heterocycloalkyl may contain one or two alkylene bridges or an alkenylene bridge, or mixture thereof, each consisting of no more than four carbon atoms and each linking two non adjacent atoms of the ring system. Examples of such bridged heterocycloalkyls include, but are not limited to, azabicyclo [2.2.1]heptyl (including 2-azabicyclo[2.2.1]hept-2-yl), 8-azabicyclo[3.2.1]oct-8-yl, octahydro-2,5-epoxypentalene, hexahydro-2H-2,5-methanocyclopenta[b]furan, hexahydro-1H-1,4-methanocyclopenta[c]furan, aza-admantane (1-azatricyclo[3.3.1.1$^{3,7}$]decane), and oxa-adamantane (2-oxatricyclo[3.3.1.1$^{3,7}$]decane). The term "6- to 9-membered bridged bicyclic heterocycloalkyl" refers to a ring radical which is either saturated or unsaturated, and which is the result of the fusion of 5-, 6-, or 7-membered monocyclic heterocycloalkyl to a 3-, 4-, or 5-membered monocyclic heterocycloalkyl; or a 5-, 6-, or 7-membered monocyclic heterocycloalkyl to a $C_5$-$C_7$-cycloalkyl, wherein the fusion junctions have 1 to 3 intervening ring atoms. The term "6- to 9-membered bridged bicyclic heterocycloalkyl" includes saturated and unsaturated "6- to 9-membered bridged bicyclic heterocycloalkyls." "6- to 9-membered bridged bicyclic heterocycloalkyls" may be substituted as set out above for alkyl. Examples of "6- to 9-membered bridged bicyclic heterocycloalkyls" include 3-azabicyclo[4.2.1]nonanyl and 7-azabicyclo[2.2.1]heptanyl.

A spiro heterocycloalkyl is a 7 to 15 membered heterocycloalkyl wherein two substituents on the same carbon atom of a monocyclic 5 to 7 membered heterocycloalkyl ring together with said carbon atom form a second ring system selected from a monocyclic cycloalkyl, a bicyclic cycloalkyl, a monocyclic heterocycloalkyl, or a bicyclic heterocycloalkyl. Examples of spiro heterocycloalkyls include, but not limited to, 6-azaspiro[2.5]oct-6-yl, 1'H, 4H-spiro[1,3-benzodioxine-2,4'-piperidin]-1'-yl, 1'H, 3H-spiro[2-benzofuran-1,4'-piperidin]-1'-yl, and 1,4-dioxa-8-azaspiro[4.5]dec-8-yl. The monocyclic, the bicyclic, and the spiro heterocycloalkyls can be unsubstituted or substituted. The monocyclic, the bicyclic and the spiro heterocycloalkyls are connected to the parent molecular moiety through any carbon atom or any nitrogen atom contained within the ring systems. The nitrogen and sulfur heteroatoms in the heterocycloalkyl rings may optionally be oxidized (e.g. 1,1-dioxidotetrahydrothienyl, 1,2-dioxido-1,2-thiazolidinyl, 1,1-dioxidothiomorpholinyl)) and the nitrogen atoms may optionally be quarternized.

An aryl group is an aromatic hydrocarbon radical. Typical aryl groups include phenyl, and naphthyl. In addition, the term "aryl" includes 9 to 12 membered bicyclic aryl groups. The term "9 to 12-membered bicyclic aryl" is a radical of a bicyclic group formed by the fusion of a benzene ring to: (1) a $C_5$-$C_8$ monocyclic cycloalkyl (e.g., indanyl; 1,2,3,4-tetrahydro-naphthalenyl; 6,7,8,9-tetrahydro-5H-benzocycloheptenyl, etc.); or (2) a 5- to 7-membered heterocycloalkyl, which may be substituted with one or two oxo groups (e.g., indolinyl, 1,3-benzodioxolyl, 1,3-dioxoisoindolinyl, isoindolinyl, etc.); wherein the fusion junctions are at adjacent carbons on the benzene ring.

The term "heteroaryl" as used herein, encompasses monocyclic 5 or 6 membered heteroaryls and bicyclic 8 to 12 membered heteroaryls.

A "5-membered heteroaryl" is a 5-membered, monocyclic, aromatic ring radical having from 1 to 4 carbon atoms and from 1 to 4 heteroatoms selected from the group consisting of: 1 O; 1 S; 1 N; 2 N; 3 N; 4 N; 1 S and 1 N; 1 S and 2 N; 1 O and 1 N; and 1 O and 2 N. Illustrative examples of 5-membered heteroaryls include, but are not limited to, furanyl, 2-furanyl, 3-furanyl, imidazolyl, isoxazolyl, isothiazolyl, oxadiazolyl, oxazolyl, pyrazolyl, pyrrolyl, 2- or 3-pyrrolyl, thienyl, 2-thienyl, 3-thienyl, tetrazolyl, thiazolyl, thiadiazolyl, and triazolyl.

A "6-membered heteroaryl" is a 6-membered, monocyclic, aromatic ring radical having from 3 to 5 carbon atoms and from 1 to 3 heteroatoms selected from the group consisting of: 1 N; 2 N; and 3 N. Illustrative examples of 6-membered heteroaryls include, but are not limited to, pyridinyl, 2-, 3-, or 4-pyridinyl, pyrimidinyl, 2-, 4-, or 5-pyrimidinyl, pyrazinyl, pyridazinyl, 3- or 4-pyridazinyl, 2-pyrazinyl, and triazinyl.

An "8- to 12-membered bicyclic heteroaryl" is a ring structure formed by the fusion of 5- or 6-membered heteroaryl to: (1) an independently selected 5-membered heteroaryl; (2) an independently selected 6-membered heteroaryl (e.g., naphthyridinyl, pteridinyl, phthalazinyl, purinyl, etc.); (3) a $C_5$-$C_8$ monocyclic cycloalkyl; (4) a 5- to 7-membered heterocycloalkyl; or (5) a benzene ring (e.g., benzimidazolyl, benzofuranyl, benzofurazanyl, benzothiazolyl, benzothiophenyl, benzoxazolyl, cinnolinyl, indolyl, or 2-, 3-, 4-, 5-, 6-, or 7-indolyl, quinazolinyl, quinoxalinyl, isoindolyl, and isoquinolinyl), wherein the fusion junctions are at adjacent ring atoms. The fusion junctions may be at nitrogen (e.g., indolizine) or carbon atoms in the 5- or 6-membered heteroaryl.

The term "hydrogen" (alone or in combination with another term(s)) means a hydrogen radical, and may be depicted as —H.

The term "hydroxy" (alone or in combination with another term(s)) means —OH.

The term "carboxy" (alone or in combination with another term(s)) means —C(O)—OH.

The term "amino" (alone or in combination with another term(s)) means —NH$_2$.

The term "halogen" or "halo" (alone or in combination with another term(s)) means a fluorine radical (which may be depicted as —F), chlorine radical (which may be depicted as —Cl), bromine radical (which may be depicted as —Br), or iodine radical (which may be depicted as —I). The prefix "halo" indicates that the substituent to which the prefix is attached is substituted with one or more independently selected halogen radicals. For example, haloalkyl means an alkyl substituent in which at least one hydrogen radical is replaced with a halogen radical. Examples of haloalkyls include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated). Examples of haloalkyl include $C_1$-$C_3$ haloalkyls, which is a halogenated alkyl containing from 1 to 3 carbons.

If a moiety is described as "substituted", a non-hydrogen radical is in the place of hydrogen radical of any substitutable atom of the moiety. Thus, for example, a substituted heteroaryl moiety is a heteroaryl moiety in which at least one non-hydrogen radical is in the place of a hydrogen radical on the heterocyclic ring. It should be recognized that if there are more than one substitution on a moiety, each non-hydrogen radical may be identical or different (unless otherwise stated).

If a moiety is described as being "optionally substituted," the moiety may be either (1) not substituted or (2) substituted. If a moiety is described as being optionally substituted with up to a particular number of non-hydrogen radicals, that moiety may be either (1) not substituted; or (2) substituted by up to that particular number of non-hydrogen radicals or by up to the maximum number of substitutable positions on the moiety, whichever is less. Thus, for example, if a moiety is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

The terms "treat", "treating", and "treatment" refer to a method of alleviating or abrogating a disease and/or its attendant symptoms.

The terms "prevent", "preventing", and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The phrase "therapeutically effective amount" means an amount of a compound, or a pharmaceutically acceptable salt thereof, sufficient to prevent the development of or to alleviate to some extent one or more of the symptoms of the condition or disorder being treated when administered alone or in conjunction with another pharmaceutical agent or treatment in a particular subject or subject population. For example in a human or other mammal, a therapeutically effective amount can be determined experimentally in a laboratory or clinical setting, or may be the amount required by the guidelines of the United States Food and Drug Administration, or equivalent foreign agency, for the particular disease and subject being treated.

The term "subject" is defined herein to refer to animals such as mammals, including, but not limited to, primates (e.g., humans), cows, sheep, goats, horses, dogs, cats, rabbits, rats, mice and the like. In preferred embodiments, the subject is a human.

Compounds

Geometric isomers may exist in the present compounds. Compounds of this invention may contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this invention may also exist as a mixture of "E" and "Z" isomers. Substituents around a cycloalkyl or heterocycloalkyl may also be designated as being of cis or trans configuration.

Compounds of this invention may contain asymmetrically substituted carbon atoms in the R or S configuration, in which the terms "R" and "S" are as defined by the IUPAC 1974 Recommendations for Section E, Fundamental Stereochemistry, Pure Appl. Chem. (1976) 45, 13-10. Compounds having asymmetrically substituted carbon atoms with equal amounts of R and S configurations are racemic at those carbon atoms. Atoms with an excess of one configuration over the other are assigned the configuration present in the higher amount, preferably an excess of about 85%-90%, more preferably an excess of about 95%-99%, and still more preferably an excess greater than about 99%. Accordingly, this invention includes racemic mixtures, relative and absolute stereoisomers, and mixtures of relative and absolute stereoisomers.

Compounds of formula (I) may contain one or more asymmetrically substituted atoms. Compounds of formula I may also exist as individual stereoisomers (including enantiomers and diastereomers) and mixtures thereof. Individual stereoisomers of compounds of formula I may be prepared synthetically from commercially available starting materials that contain asymmetric or chiral centers or by preparation of racemic mixtures followed by resolution of the individual stereoisomer using methods that are known to those of ordinary skill in the art. Examples of resolution are, for example, (i) attachment of a mixture of enantiomers to a chiral auxiliary, separation of the resulting mixture of diastereomers by recrystallization or chromatography, followed by liberation of the optically pure product; or (ii) separation of the mixture of enantiomers or diastereomers on chiral chromatographic columns.

Compounds of formula I may also include the various geometric isomers and mixtures thereof resulting from the disposition of substituents around a carbon-carbon double bond, a carbon-nitrogen double bond, a cycloalkyl group, or a heterocycloalkyl group. Substituents around a carbon-carbon double bond or a carbon-nitrogen double bond are designated as being of Z or E configuration and substituents around a cycloalkyl or heterocycloalkyl are designated as being of cis or trans configuration.

Within the present invention it is to be understood that compounds disclosed herein may exhibit the phenomenon of tautomerism and all tautomeric isomers are included in the scope of the invention.

Thus, the formula drawings within this specification can represent only one of the possible tautomeric, geometric, or stereoisomeric forms. It is to be understood that the invention encompasses any tautomeric, geometric, or stereoisomeric form, and mixtures thereof, and is not to be limited merely to any one tautomeric, geometric, or stereoisomeric form utilized within the formula drawings.

Isotope Enriched or Labeled Compounds

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to, $^{2}$H, $^{3}$H, $^{13}$C, $^{14}$C, $^{15}$N, $^{18}$O, $^{32}$P, $^{35}$S, $^{18}$F, $^{36}$Cl, and $^{125}$I. Compounds that contain other isotopes of these and/or other atoms are within the scope of this invention.

In another embodiment, the isotope-labeled compounds contain deuterium ($^{2}$H), tritium ($^{3}$H) or $^{14}$C isotopes. Isotope-labeled compounds of this invention can be prepared by the general methods well known to persons having ordinary skill in the art. Such isotope-labeled compounds can be conveniently prepared by carrying out the procedures disclosed in the Examples disclosed herein and Schemes by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuteric acid such as $D_2SO_4/D_2O$. In addition to the above, relevant procedures and intermediates are disclosed, for instance, in Lizondo, J et al., *Drugs Fut*, 21(11), 1116 (1996); Brickner, S J et al., *J Med Chem*, 39(3), 673 (1996); Mallesham, B et al., *Org Lett*, 5(7), 963 (2003); PCT publications WO1997010223, WO2005099353, WO1995007271, WO2006008754; U.S. Pat. Nos. 7,538,189; 7,534,814; 7531685; 7528131; 7521421; 7514068; 7511013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention may be used as standards to determine the effectiveness of BET bromodomain inhibitors in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., *J. Labelled Comp. Radiopharmaceut.*, 36(10):927-932 (1995); Kushner et al., *Can. J. Physiol. Pharmacol.*, 77, 79-88 (1999).

In addition, non-radio active isotope containing drugs, such as deuterated drugs called "heavy drugs," can be used for the treatment of diseases and conditions related to BET bromodomain activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci. 1960 84: 736; Czakja D M et al., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Stable isotope labeling of a drug can alter its physico-chemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions potentially altering the pharmacokinetic profile or efficacy relative to the non-isotopic compound.

Schemes

Compounds of the present invention (e.g., compounds of Formula I) can be prepared by applying synthetic methodology known in the art and synthetic methodology outlined in the schemes set forth below. The compounds described herein, including compounds of general formula (I) and specific examples, can be prepared, for example, through the reaction schemes depicted in schemes 1-5. The variables A, Y, J, $R^1$, $R^2$, $R^3$, $R^{10}$, $R^{11}$, $R^{12}$, $R^{13}$, and $R^{14}$ used in the following schemes have the meanings as set forth in the summary and detailed description sections, unless otherwise noted.

Abbreviations used in the descriptions of the schemes and the specific examples have the following meanings: DME for 1,2-dimethoxyethane, DMF for dimethylformamide, DMSO for dimethyl sulfoxide, EDAC for 1-ethyl-3-[3-(dimethylamino)propyl]-carbodiimide hydrochloride; EtOH for ethanol; EtOAc for ethyl acetate; HATU for O-(7-azabenzotriazol-1-yl)-N,N,N',N'-tetramethyluronium hexafluorophosphate, $PdCl_2(PPh_3)_2$ for bis(triphenylphosphine)palladium(II) dichloride; $Pd_2(dba)_3$ for tris(dibenzylideneacetone)dipalladium(0); THF for tetrahydrofuran, TFA for trifluoroacetic acid, and HPLC for high performance liquid chromatography.

Compounds of general formula (I) may be prepared using general procedure as outlined in Scheme 1. Halides of formula (2) wherein X is Cl, Br, or I may be prepared from halogenation of compounds of formula (I) using general methodologies for those reactions, for example, by treating (1) with N-bromosuccinimide in a solvent such as, but not limited to, tetrahydrofuran, acetonitrile, or acetone, at a temperature of about −78° C. to 25° C., to provide compounds of formula (2) wherein X is Br. Conversion of (2) to compounds of general formula (I) may be achieved by reaction of (2) with a boronic acid of formula $R^3B(OH)_2$ or derivative thereof (e.g. pinacol ester) under Suzuki coupling conditions (N. Miyama and A. Suzuki, Chem. Rev. 1995, 95:2457-2483, J. Organomet. Chem. 1999, 576:147-148). Generally, the coupling reaction may be conducted in the presence of a palladium catalyst and a base, and optionally in the presence of a ligand, and in a suitable solvent at elevated temperature (about 80° C. to about 150° C.). The reaction may be facilitated by microwave irradiation. Examples of the palladium catalyst include, but are not limited to, tetrakis(triphenylphosphine)palladium(0), tris(dibenzylideneacetone)dipalladium(0), bis(triphenylphosphine)palladium(II) dichloride, or palladium(II)acetate. Examples of suitable bases that may be employed include, but not limited to, carbonates or phosphates of sodium, potassium, and cesium, and cesium fluoride. Examples of suitable ligands include, but are not limited to, 1,3,5,7-tetramethyl-6-phenyl-2,4,8-trioxa-6-phosphaadamante, 2-dicyclohexylphosphino-2',4',6'-triisopropylbiphenyl (X-phos), or 1,1'-bis(diphenylphosphanyl) ferrocene. Non-limiting examples of suitable solvent include methanol, ethanol, dimethoxyethane, N,N-dimethylformamide, dimethylsulfoxide, dioxane, tetrahydropyran, and water, or a mixture thereof.

Alternatively, compounds of formula (I) may be synthesized from the reaction of isoindolinone (1) with halides of formula $R^3X$ wherein X is Br or I in the presence of a palladium(II) catalyst such as allylpalladium(II) chloride dimer, and in a solvent such as but not limited to dimethylacetamide or N,N-dimethylformamide at temperatures ranging from about 80° C. to about 150° C.

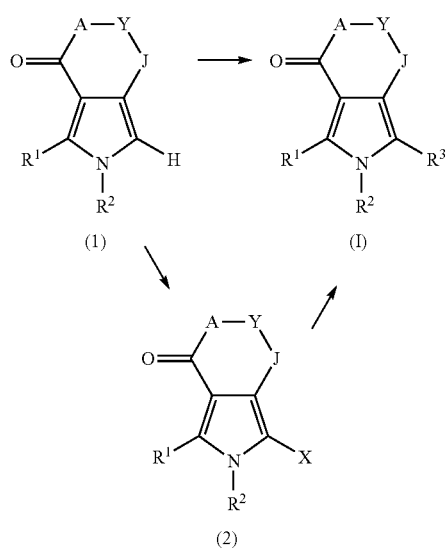

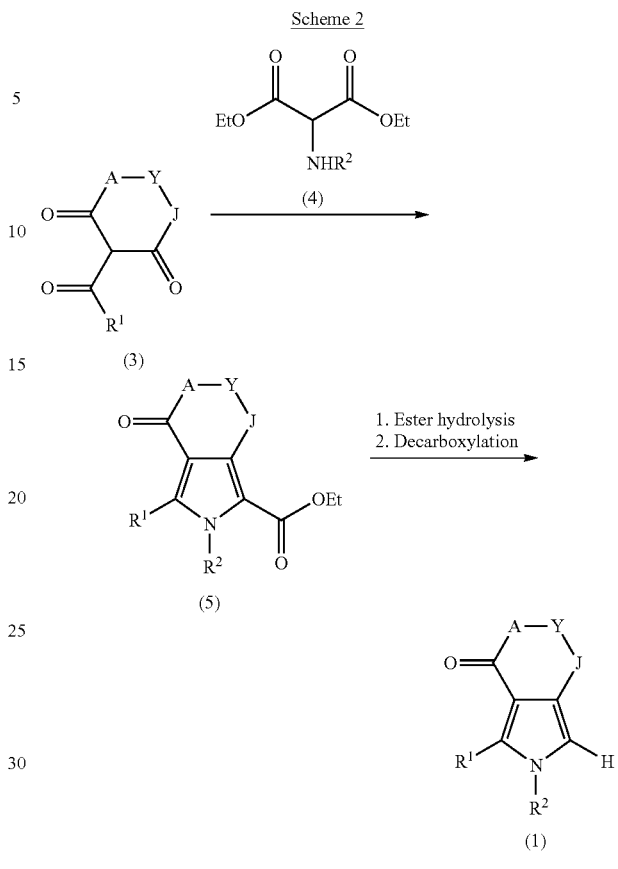

Compounds of formula (I) wherein $R^2$ is hydrogen and $R^1$ is $C_1$-$C_3$ alkyl may be prepared using synthetic routes such as, but not limited to, those illustrated in Scheme 2.

Reaction of compounds of formula (3) wherein $R^1$ is $C_1$-$C_3$ alkyl with 2-aminomalonate derivatives (4) wherein $R^2$ is hydrogen, in the presence of sodium acetate and in a solvent such as, but not limited to, acetic acid, provides intermediates of formula (3). The reaction may be conducted at elevated temperature such as, but not limited to, about 80° C. to about 120° C. Ester hydrolysis of (5) followed by decarboxylation of the resulting carboxylic acid affords compounds of formula (I). For example, ester hydrolysis may be achieved in the presence of a base such as, but not limited to, hydroxides of lithium, potassium, or sodium. The reaction is generally conducted in a solvent such as, but not limited to, tetrahydrofuran or water, and at temperatures ranging from about room temperature to about 80° C. Heating of the resulting carboxylic acid in an alcoholic solvent (e.g., ethanol), and in the presences of an acid such as, but not limited to, hydrochloric acid or sulfuric acid, at a temperature from about 50° C. to about 100° C. provide compounds of formula (I) wherein $R^1$ is $C_1$-$C_3$ alkyl and $R^2$ is hydrogen.

Compounds of formula (I) wherein $R^3$ is a phenyl having an ortho substituent, $OR^{101}$, wherein $R^{101}$ is $C_1$-$C_3$ alkyl, aryl, $C_1$-$C_3$ alkylenyl-aryl, $C_1$-$C_3$ alkylenyl-heterocycloalkyl, $C_1$-$C_3$ alkylenyl-cycloalkyl, or $C_1$-$C_3$ alkylenyl-heteroaryl, may be prepared as shown in Scheme 3.

Compounds of formula (7) wherein may be prepared from reaction of (2a) with a boronic acid of formula (6) or derivatives thereof (e.g., pinacol ester) using Suzuki coupling conditions as described in Scheme 1. Treatment of the resulting phenols of formula (7) with an appropriate halide of formula $R^{101}X$ in the presence of a base such as carbonate of cesium, potassium and sodium, in a solvent such as dimethylformamide or dimethylsulfoxide, and at temperatures ranging from about room temperature to about 100° C. provides compounds of formula (10). Alternatively, reaction of phenol (7) with an alcohol of formula $R^{101}OH$ in the presence of triphenylphosphine and in the presence of diisopropylazodicarboxylate or diethylazodicarboxylate, in a solvent such as tetrahydrofuran or dioxane, and at temperatures ranging from about room temperature to about 100° C. provides compounds of formula (10).

Alternatively, compounds of formula (10) may be obtained by (a) coupling of (2a) with (8) using reaction conditions described in Scheme 1; and (b) displacement of the fluorine atom of formula (9) with an alcohol of formula $R^{101}OH$. Displacement of the fluorine atom may be accomplished in a solvent such as, but not limited to, dimethylsulfoxide, dimethylformamide, dioxane, or tetrahydrofuran and in the presence of a base such as, but not limited to, carbonate of cesium, potassium, and sodium, or sodium hydride, and at a temperature from about 40° C. to about 120° C.

Scheme 3

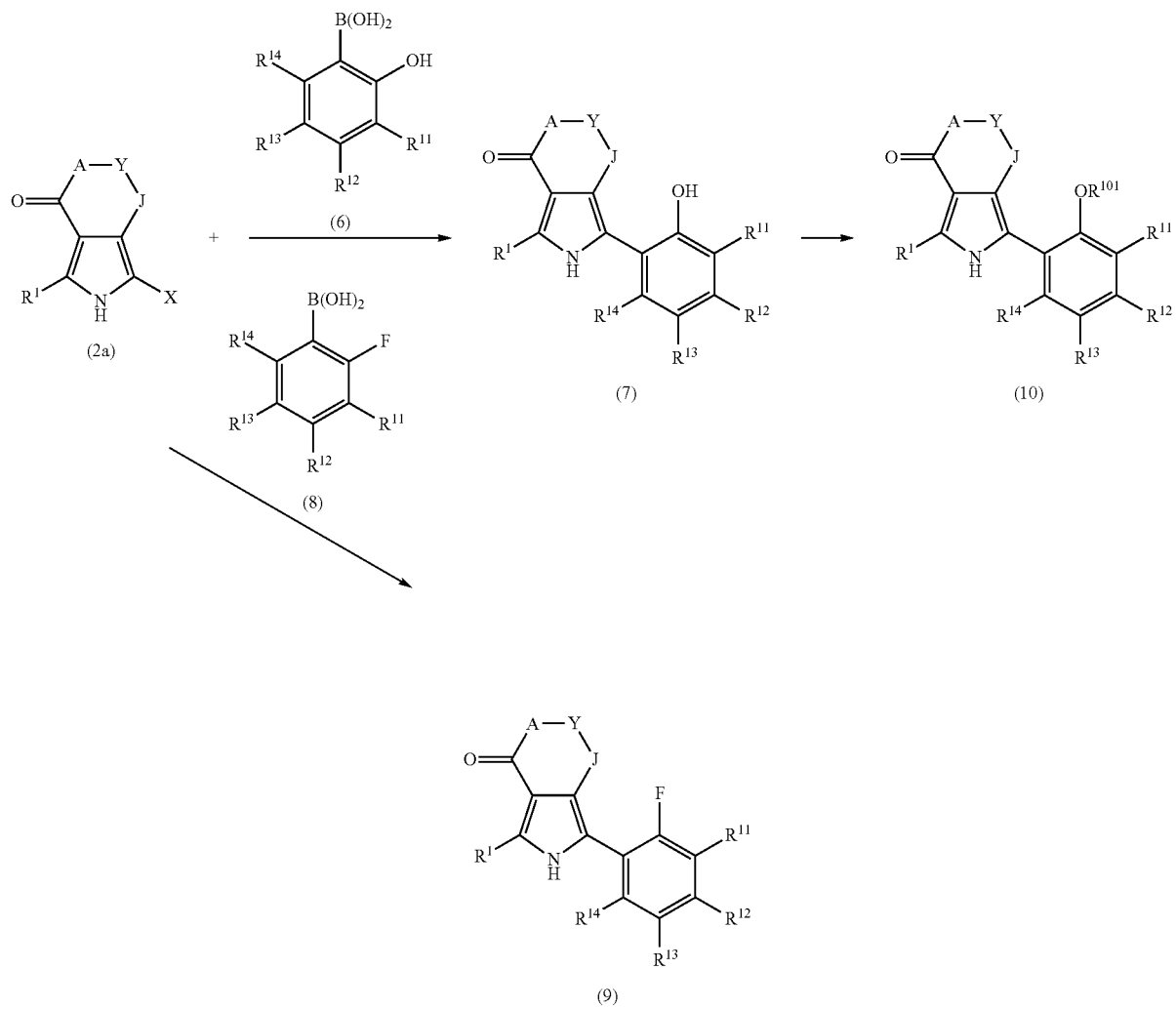

Compounds of formula (I) where $R^{10}$ is $OR^{101}$ wherein $R^{101}$ is as defined above, and $R^{13}$ is $NO_2$ may be further derivatized as illustrated in Scheme 4.

Reduction of the nitro compounds of formula (11) to the anilines of formula (12). may be achieved using iron powder in the presence of ammonium chloride in a solvent such as, but not limited to, tetrahydrofuran, ethanol, or water, or a mixture thereof, and at a temperature from about 80° C. to about 120° C. Alternatively this reduction may be carried out with tin chloride in hydrochloric acid at a temperature from about 80° C. to about 120° C. Transformation of (11) to (12) may also be conducted in the presence of a catalyst such as platinum oxide or palladium on charcoal, in a solvent such as ethanol or methanol and under hydrogen pressure. Treatment of aniline (12) with sulfonyl chlorides of formula $R^{102}SO_2Cl$ wherein $R^{102}$ is alkyl or haloalkyl, in the presence of a base such as triethylamine or diisopropylethylamine in a solvent such as dichloromethane or tetrahydrofuran and at a temperature from about 0° C. to about 40° C. provides sulfonamides (13).

Treatment of aniline (12) with carboxylic acids of formula $R^{103}COOH$ wherein $R^{103}$ is $C_1$-$C_3$ alkyl, in the presence of a coupling agent such as HATU or EDAC and a base such as diisopropylethylaminde or triethylamine, and in a solvent such as tetrahydrofuran, dioxane, or dimethylformamide, at a temperature from about 0° C. to about 40° C. provides amides of formula (14).

Scheme 4

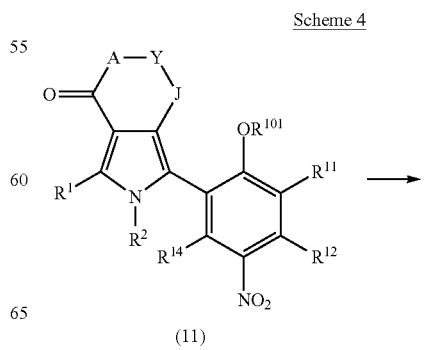

-continued

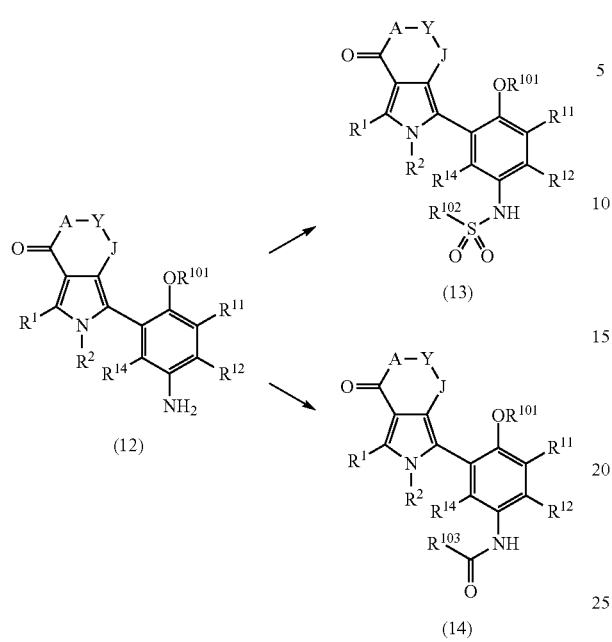

Compounds of formula (I) wherein $R^{10}$ is $OR^{101}$ and $R^{13}$ is $C(O)N(R^{104})(R^{105})$ wherein $R^{101}$ is as defined above, $R^{104}$ is hydrogen and $R^{105}$ is hydrogen, $C_1$-$C_3$ alkyl, —$C_1$-$C_3$ alkylene-heterocycloalkyl, or heteroaryl, may be prepared as shown in Scheme 5.

Hydrolysis of the ester moiety of (15) provides acids of formula (16). The hydrolysis step may be carried out in the presence of a base such as hydroxide of lithium, sodium, or potassium, in a solvent such as, but not limited to, tetrahydrofuran, water, methanol, or dioxane, or combinations thereof, and at a temperature from about 25° C. to 60° C. Utilizing the amide coupling reaction conditions discussed in Scheme 4, acids of formula (16) may be treated with amines of formula $NHR^{104}R^{105}$ to provide amides of formula (17).

Scheme 5

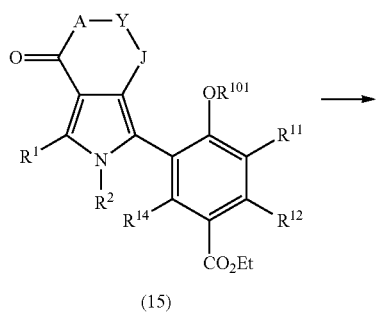

It can be appreciated that the synthetic schemes and specific examples as illustrated in the synthetic examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step can vary depending on the particular reactants employed and substituents present in the reactants used. Specific procedures are provided in the Synthetic Examples section. Reactions can be worked up in the conventional manner, e.g. by eliminating the solvent from the residue and further purified using methodologies for purifying compounds from reaction mixtures such as, but not limited to, precipitation, crystallization, distillation, extraction, trituration and chromatography.

Routine experimentations, including appropriate manipulation of the reaction conditions, reagents and sequence of the synthetic route, protection of any chemical functionality that can not be compatible with the reaction conditions, and deprotection at a suitable point in the reaction sequence of the method are included in the scope of the invention. Suitable protecting groups and the methods for protecting and deprotecting different substituents using such suitable protecting groups may be used; examples of which can be found in T. Greene and P. Wuts, Protecting Groups in Organic Synthesis ($3^{rd}$ ed.), John Wiley & Sons, NY (1999), which is incorporated herein by reference in its entirety. Synthesis of the compounds of the invention can be accomplished by methods analogous to those described in the synthetic schemes described hereinabove and in specific examples.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound is required, typically it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, crystallization, or enzymatic resolution).

Similarly, when a pure geometric isomer of a compound is required, it can be prepared by carrying out one of the above procedures using a pure geometric isomer as a starting material, or by resolution of a mixture of the geometric isomers of the compound or intermediates using a standard procedure such as chromatographic separation.

Compounds of formula I can be used in the form of pharmaceutically acceptable salts. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio.

Pharmaceutically acceptable salts have been described in S. M. Berge et al. J. Pharmaceutical Sciences, 1977, 66: 1-19.

Compounds of formula (I) may contain either a basic or an acidic functionality, or both, and can be converted to a pharmaceutically acceptable salt, when desired, by using a suitable acid or base. The salts may be prepared in situ during the final isolation and purification of the compounds of the invention.

Examples of acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts may be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other examples of organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use.

The present invention contemplates compounds of formula (I) formed by synthetic means or formed by in vivo biotransformation of a prodrug.

Compounds described herein can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

Pharmaceutical Compositions

This invention also provides for pharmaceutical compositions comprising a therapeutically effective amount of a compound of Formula I, or a pharmaceutically acceptable salt thereof together with a pharmaceutically acceptable carrier, diluent, or excipient therefor. The phrase "pharmaceutical composition" refers to a composition suitable for administration in medical or veterinary use.

The pharmaceutical compositions that comprise a compound of formula (I), alone or or in combination with a second active pharmaceutical agent, may be administered to the subjects orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents, which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally-administered drug form may be accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In certain embodiments, solid dosage forms may contain from 1% to 95% (w/w) of a compound of formula I. In certain embodiments, the compound of formula I may be present in the solid dosage form in a range of from 5% to 70% (w/w). In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

The pharmaceutical composition may be a unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampules. Also, the unit dosage form can be a capsule, tablet, cachet, or lozenge itself, or it can be the appropriate number of any of these in packaged form. The quantity of active component in a unit dose preparation may be varied or adjusted from 0.1 mg to 1000 mg, from 1 mg to 100 mg, or from 1% to 95% (w/w) of a unit dose, according to the particular application and the potency of the active component. The composition can, if desired, also contain other compatible therapeutic agents.

The dose to be administered to a subject may be determined by the efficacy of the particular compound employed and the condition of the subject, as well as the body weight or surface area of the subject to be treated. The size of the dose also will be determined by the existence, nature, and extent of any adverse side-effects that accompany the administration of a particular compound in a particular subject. In determining the effective amount of the compound to be administered in the treatment or prophylaxis of the disorder being treated, the physician can evaluate factors such as the circulating plasma levels of the compound, compound toxicities, and/or the progression of the disease, etc. In general, the dose equivalent of a compound is from about 1 µg/kg to 100 mg/kg for a typical subject.

For administration, compounds of the formula I can be administered at a rate determined by factors that can include, but are not limited to, the $LD_{50}$ of the compound, the pharmacokinetic profile of the compound, contraindicated drugs, and the side-effects of the compound at various concentrations, as applied to the mass and overall health of the subject. Administration can be accomplished via single or divided doses.

The compounds utilized in the pharmaceutical method of the invention can be administered at the initial dosage of about 0.001 mg/kg to about 100 mg/kg daily. In certain embodiments, the daily dose range is from about 0.1 mg/kg to about 10 mg/kg. The dosages, however, may be varied depending upon the requirements of the subject, the severity of the condition being treated, and the compound being employed. Determination of the proper dosage for a particular situation is within the skill of the practitioner. Treatment may be initiated with smaller dosages, which are less than the optimum dose of the compound. Thereafter, the dosage is increased by small increments until the optimum effect under circumstances is reached. For convenience, the total daily dosage may be divided and administered in portions during the day, if desired.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of formula I may also be administered in the form of liposomes. Liposomes generally may be derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form may contain, in addition to a compound of formula (I), stabilizers, preservatives, excipients and the like. Examples of lipids include, but are not limited to, natural and synthetic phospholipids and phosphatidyl cholines (lecithins), used separately or together.

Methods to form liposomes have been described, see example, Prescott, Ed., Methods in Cell Biology, Volume XIV, Academic Press, New York, N.Y. (1976), p. 33 et seq.

Dosage forms for topical administration of a compound described herein include powders, sprays, ointments and inhalants. The active compound may be mixed under sterile conditions with a pharmaceutically acceptable carrier and any needed preservatives, buffers or propellants which may be required. Ophthalmic formulations, eye ointments, powders and solutions are also contemplated as being within the scope of this invention.

Methods of Use

The compounds of formula I, or pharmaceutically acceptable salts thereof, and pharmaceutical compositions comprising a compound of formula I, or a pharmaceutically acceptable salt thereof, can be administered to a subject suffering from a bromodomain-mediated disorder or condition. The term "administering" refers to the method of contacting a compound with a subject. Thus, the compounds of formula I can be administered by injection, that is, intravenously, intramuscularly, intracutaneously, subcutaneously, intraduodenally, parentally, or intraperitoneally. Also, the compounds described herein can be administered by inhalation, for example, intranasally. Additionally, the compounds of formula I can be administered transdermally, topically, via implantation, transdermally, topically, and via implantation. In certain embodiments, the compounds of the formula I may be delivered orally. The compounds can also be delivered rectally, bucally, intravaginally, ocularly, andially, or by insufflation. Bromodomain-mediated disorders and conditions can be treated prophylactically, acutely, and chronically using compounds of formula I, depending on the nature of the disorder or condition. Typically, the host or subject in each of these methods is human, although other mammals can also benefit from the administration of a compound of formula I.

A "bromodomain-mediated disorder or condition" is characterized by the participation of one or more bromodomains (e.g., BRD4) in the inception, manifestation of one or more symptoms or disease markers, severity, or progression of a disorder or condition. Accordingly, compounds of formula I may be used to treat cancer, including, but not limited to acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenström's macroglobulinemia, testicular tumors, uterine cancer and Wilms' tumor.

Further, compounds of formula I may be used to treat inflammatory diseases, inflammatory conditions, and autoimmune diseases, including, but not limited to: Addison's disease, acute gout, ankylosing spondylitis, asthma, atherosclerosis, Behcet's disease, bullous skin diseases, chronic obstructive pulmonary disease (COPD), Crohn's disease, dermatitis, eczema, giant cell arteritis, glomerulonephritis, hepatitis, hypophysitis, inflammatory bowel disease, Kawasaki disease, lupus nephritis, multiple sclerosis, myocarditis, myositis, nephritis, organ transplant rejection, osteoarthritis, pancreatitis, pericarditis, Polyarteritis nodosa, pneumonitis, primary biliary cirrhosis, psoriasis, psoriatic arthritis, rheumatoid arthritis, scleritis, sclerosing cholangitis, sepsis, systemic lupus erythematosus, Takayasu's Arteritis, toxic shock, thyroiditis, type I diabetes, ulcerative colitis, uveitis, vitiligo, vasculitis, and Wegener's granulomatosis.

Compounds of formula I, or pharmaceutically acceptable salts thereof, may be used to treat AIDS. In addition, compounds of formula I, or pharmaceutically acceptable salts thereof, may be used to treat obesity. Compounds of formula I, or pharmaceutically acceptable salts thereof, may be used to treat type II diabetes.

Compounds of formula I, or pharmaceutically acceptable salts thereof, may be used to treat a disease or condition selected from the group consisting of: obesity, dyslipidemia, hypercholesterolemia, Alzheimer's disease, metabolic syndrome, hepatic steatosis, type II diabetes, insulin resistance, diabetic retinopathy and diabetic neuropathy.

Compounds of formula I, or pharmaceutically acceptable salts thereof, may be used to provide for contraception in a male subject by administering a therapeutically effective amount of a compound of formula (I), or a pharmaceutically acceptable salt thereof.

Compounds of formula I, or pharmaceutically acceptable salts thereof, may be used to treat a chronic kidney disease or condition in a subject by administering a therapeutically effective amount of a compound of formula (I), wherein said disease or condition is selected from the group consisting of: diabetic nephropathy, hypertensive nephropathy, HIV-associated nephropathy, glomerulonephritis, lupus nephritis, IgA nephropathy, focal segmental glomerulosclerosis, membranous glomerulonephritis, minimal change disease, polycystic kidney disease and tubular interstitial nephritis.

Compounds of formula I, or pharmaceutically acceptable salts thereof, may be used to treat an acute kidney disease or condition in a subject that is selected from the group consisting of: ischemia-reperfusion induced kidney disease, cardiac and major surgery induced kidney disease, percutaneous coronary intervention induced kidney disease, radio-contrast agent induced kidney disease, sepsis induced kidney disease, pneumonia induced kidney disease, and drug toxicity induced kidney disease.

The compounds of formula I can be co-administered to a subject. The term "co-administered" means the administration of two or more different pharmaceutical agents or treatments (e.g., radiation treatment) that are administered to a subject by combination in the same pharmaceutical composition or separate pharmaceutical compositions. Thus co-administration involves administration at the same time of a single pharmaceutical composition comprising two or more pharmaceutical agents or administration of two or more different compositions to the same subject at the same or different times.

The compounds of the invention can be co-administered with a therapeutically effective amount of one or more agents to treat a cancer, where examples of the agents include, such as radiation, alkylating agents, angiogenesis inhibitors, antibodies, antimetabolites, antimitotics, antiproliferatives, antivirals, aurora kinase inhibitors, apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs (dual variable domain antibodies), leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (bromodomain) inhibitors, proteosome inhibitors, purine analogs, pyrimidine analogs, receptor tyrosine kinase inhibitors, etinoids/deltoids plant alkaloids, small inhibitory ribonucleic acids (siRNAs), topoisomerase inhibitors, ubiquitin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (V. R. Sutton, D. L. Vaux and J. A. Trapani, *J. of Immunology* 1997, 158 (12), 5783).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand.

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site. Multispecific DVDs include DVD binding proteins that bind DLL4 and VEGF, or C-met and EFGR or ErbB3 and EGFR.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like.

Aurora kinase inhibitors include ABT-348, AZD-1152, MLN-8054, VX-680, Aurora A-specific kinase inhibitors, Aurora B-specific kinase inhibitors and pan-Aurora kinase inhibitors and the like.

Bcl-2 protein inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax), ABT-199, and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include EGFR antibodies, ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecific antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FC1, PU-3, radicicol, SNX-2112, STA-9090 VER49009 and the like.

Inhibitors of inhibitors of apoptosis proteins include HGS1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-011-vcMMAE, PSMA-ADC, MEDI-547, SGN-19 Am SGN-35, SGN-75 and the like Activators of death receptor pathway include TRAIL, antibodies or other agents that target TRAIL or death receptors (e.g., DR4 and DR5) such as Apomab, conatumumab, ETR2-ST01, GDC0145, (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474), GA101, ofatumumab, ABT-806 (mAb-806), ErbB3 specific antibodies, BSG2 specific antibodies, DLL4 specific antibodies and C-met specific antibodies, and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirubicin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARD10×ANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab, CD20 antibodies types I and II and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA®(letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-nl, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofiran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

Additionally, compounds having Formula (I) may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine) (ONCOVIN®; P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EPO906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTATAAE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECINT™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (Streptomyces staurospores), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

The compounds of the invention can also be co-administered with a therapeutically effective amount of one or more agents to treat an inflammatory disease or condition, or autoimmune disease, where examples of the agents include, such as methotrexate, 6-mercaptopurine, azathioprine sulphasalazine, mesalazine, olsalazine chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g., NIK, IKK, p38 or MAP kinase inhibitors), IL-1β converting enzyme inhibitors, T-cell signalling inhibitors such as kinase inhibitors, metalloproteinase inhibitors, sulfasalazine, 6-mercaptopurines, angiotensin converting enzyme inhibitors, soluble cytokine receptors and derivatives thereof (e.g. soluble p55 or p75 TNF receptors and the derivatives p75TNFRIgG (etanercept) and p55TNFRIgG (Lenercept), sIL-1RI, sIL-1RII, sIL-6R), antiinflammatory cytokines (e.g. IL-4, IL-10, IL-11, IL-13 and TGFβ, celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline HCl, sulfadiazine, oxycodone HCl/acetaminophen, olopatadine HCl misoprostol, naproxen sodium, omeprazole, cyclophosphamide, rituximab, IL-1 TRAP, MRA, CTLA4-IG, IL-18 BP, anti-IL-12, Anti-IL15, BIRB-796, SC10-469, VX-702, AMG-548, VX-740, Roflumilast, IC-485, CDC-801, S1P1 agonists (such as FTY720), PKC family inhibitors (such as Ruboxistaurin or AEB-071) and Mesopram. In certain embodiments, combinations include methotrexate or leflunomide and in moderate or severe rheumatoid arthritis cases, cyclosporine and anti-TNF antibodies as noted above.

Non-limiting examples of therapeutic agents for inflammatory bowel disease with which a compound of Formula (I) of the invention may be co-administered include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinylimidazole compounds; antibodies to or antagonists of other human cytokines or growth factors, for example, TNF, LT, IL-1, IL-2, IL-6, IL-7, IL-8, IL-12, IL-15, IL-16, IL-23, EMAP-II, GM-CSF, FGF, and PDGF; cell surface molecules such as CD2, CD3, CD4, CD8, CD25, CD28, CD30, CD40, CD45, CD69, CD90 or their ligands; methotrexate; cyclosporine; FK506; rapamycin; mycophenolate mofetil; leflunomide; NSAIDs, for example, ibuprofen; corticosteroids such as prednisolone; phosphodiesterase inhibitors; adenosine agonists; antithrombotic agents; complement inhibitors; adrenergic agents; agents which interfere with signalling by proinflammatory cytokines such as TNFα or IL-1 (e.g. NIK, IKK, or MAP kinase inhibitors); IL-1β converting enzyme inhibitors; TNFα converting enzyme inhibitors; T-cell signalling inhibitors such as kinase inhibitors; metalloproteinase inhibitors; sulfasalazine; azathioprine; 6-mercaptopurines; angiotensin converting enzyme inhibitors; soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-11, IL-13 and TGFβ. Preferred examples of therapeutic agents for Crohn's disease with which a compound of Formula (I) can be combined include the following: TNF antagonists, for example, anti-TNF antibodies, D2E7 (adalimumab), CA2 (infliximab), CDP 571, TNFR-Ig constructs, (p75TNFRIgG (etanercept) and p55TNFRIgG (LENER- CEPT™) inhibitors and PDE4 inhibitors. A compound of Formula (I) can be combined with corticosteroids, for example, budenoside and dexamethasone; sulfasalazine, 5-aminosalicylic acid; olsalazine; and agents which interfere with synthesis or action of proinflammatory cytokines such as IL-1, for example, IL-1β converting enzyme inhibitors and IL-1ra; T cell signaling inhibitors, for example, tyrosine kinase inhibitors; 6-mercaptopurine; IL-11; mesalamine; prednisone; azathioprine; mercaptopurine; infliximab; methylprednisolone sodium succinate; diphenoxylate/atrop sulfate; loperamide hydrochloride; methotrexate; omeprazole; folate; ciprofloxacin/dextrose-water; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab and interferon-gamma.

Non-limiting examples of therapeutic agents for multiple sclerosis with which a compound of Formula (I) may be co-administered include the following: corticosteroids; prednisolone; methylprednisolone; azathioprine; cyclophosphamide; cyclosporine; methotrexate; 4-aminopyridine; tizanidine; interferon-β1a (AVONEX®; Biogen); interferon-β1b (BETASERON®; Chiron/Berlex); interferon α-n3) (Interferon Sciences/Fujimoto), interferon-α (Alfa Wassermann/J&J), interferon β1A-IF (Serono/Inhale Therapeutics), Peginterferon α 2b (Enzon/Schering-Plough), Copolymer 1 (Cop-1; COPAXONE®; Teva Pharmaceutical Industries, Inc.); hyperbaric oxygen; intravenous immunoglobulin; cladribine; antibodies to or antagonists of other human cytokines or growth factors and their receptors, for example, TNF, LT, IL-1, IL-2, IL-6, IL-7, IL-8, IL-12, IL-23, IL-15, IL-16, EMAP-II, GM-CSF, FGF, and PDGF. A compound of Formula (I) can be combined with antibodies to cell surface molecules such as CD2, CD3, CD4, CD8, CD19, CD20, CD25, CD28, CD30, CD40, CD45, CD69, CD80, CD86, CD90 or their ligands. A compound of Formula (I) may also be combined with agents such as methotrexate, cyclosporine, FK506, rapamycin, mycophenolate mofetil, leflunomide, an S1P1 agonist, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g., NIK, IKK, p38 or MAP kinase inhibitors), IL-1β converting enzyme inhibitors, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-13 and TGFβ).

A compound of Formula (I) may also be co-administered with agents, such as alemtuzumab, dronabinol, daclizumab, mitoxantrone, xaliproden hydrochloride, fampridine, glatiramer acetate, natalizumab, sinnabidol, α-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists and IL-4 agonists.

Non-limiting examples of therapeutic agents for ankylosing spondylitis with which a compound of Formula (I) can be co-administered include the following: ibuprofen, diclofenac, misoprostol, naproxen, meloxicam, indomethacin, diclofenac, celecoxib, rofecoxib, sulfasalazine, methotrexate, azathioprine, minocyclin, prednisone, and anti-TNF antibodies, D2E7 (HUMIRA®), CA2 (infliximab), CDP 571, TNFR-Ig constructs, (p75TNFRIgG (ENBREL®) and p55TNFRIgG (LENERCEPT®).

Non-limiting examples of therapeutic agents for asthma with which a compound of Formula (I) may be co-administered include the following: albuterol, salmeterol/fluticasone, montelukast sodium, fluticasone propionate, budesonide, prednisone, salmeterol xinafoate, levalbuterol HCl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, amoxicillin trihydrate, flunisolide, allergy injection, cromolyn sodium, fexofenadine hydrochloride, flunisolide/menthol, amoxicillin/clavulanate, levofloxacin, inhaler assist device, guaifenesin, dexamethasone sodium phosphate, moxifloxacin HCl, doxycycline hyclate, guaifenesin/d-methorphan, p-ephedrine/cod/chlorphenir, gatifloxacin, cetirizine hydrochloride, mometasone furoate, salmeterol xinafoate, benzonatate, cephalexin, pe/hydrocodone/chlorphenir, cetirizine HCl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone, anti-IL-13 antibody, and metaproterenol sulfate.

Non-limiting examples of therapeutic agents for COPD with which a compound of Formula (I) may be co-administered include the following: albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol HCl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/chlorphenir, pirbuterol acetate, p-ephedrine/loratadine, terbutaline sulfate, tiotropium bromide, (R,R)-formoterol, TgAAT, cilomilast and roflumilast.

Non-limiting examples of therapeutic agents for psoriasis with which a compound of Formula (I) may be co-administered include the following: calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/ resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine, ABT-874 and ustekinamab.

Non-limiting examples of therapeutic agents for psoriatic arthritis with which a compound of Formula (I) may be co-administered include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, D2E7 (adalimumab), and efalizumab.

Preferred examples of therapeutic agents for SLE (Lupus) with which a compound of Formula (I) may be co-administered include the following: NSAIDS, for example, diclofenac, naproxen, ibuprofen, piroxicam, indomethacin; COX2 inhibitors, for example, celecoxib, rofecoxib, valdecoxib; anti-malarials, for example, hydroxychloroquine; steroids, for example, prednisone, prednisolone, budenoside, dexamethasone; cytotoxics, for example, azathioprine, cyclophosphamide, mycophenolate mofetil, methotrexate; inhibitors of PDE4 or purine synthesis inhibitor, for example Cellcept®. A compound of Formula (I) may also be combined with agents such as sulfasalazine, 5-aminosalicylic acid, olsalazine, Imuran® and agents which interfere with synthesis, production or action of proinflammatory cytokines such as IL-1, for example, caspase inhibitors like IL-1β converting enzyme inhibitors and IL-1ra. A compound of Formula (I) may also be used with T cell signaling inhibitors, for example, tyrosine kinase inhibitors; or molecules that target T cell activation molecules, for example, CTLA-4-IgG or anti-B7 family antibodies, anti-PD-1 family antibodies. A compound of Formula (I) can be combined with IL-11 or anti-cytokine antibodies, for example, fonotolizumab (anti-IFNg antibody), or anti-receptor receptor antibodies, for example, anti-IL-6 receptor antibody and antibodies to B-cell surface molecules. A compound of Formula (I) may also be used with UP 394 (abetimus), agents that deplete or inactivate B-cells, for example, Rituximab (anti-CD20 antibody), lymphostat-B (anti-BlyS antibody), TNF antagonists, for example, anti-TNF antibodies, D2E7 (adalimumab), CA2 (infliximab), CDP 571, TNFR-Ig constructs, (p75TNFRIgG (etanercept) and p55TNFRIgG (LENERCEPT™).

The compounds of the invention can also be co-administered with a therapeutically effective amount of one or more agents used in the prevention or treatment of AIDS, where examples of the agents include, HIV reverse transcriptase inhibitors, HIV protease inhibitors, immunomodulators, and other retroviral drugs. Examples of reverse transcriptase inhibitors include, but are not limited to, abacavir, adefovir, didanosine, dipivoxil delavirdine, efavirenz, lamivudine, nevirapine, stavudine zalcitabine, and zidovudine. Examples of protease inhibitors include, but are not limited to, amprenavir, indinavir, lopinavir, nelfinavir, ritonavir, and saquinavir.

A compound of Formula (I) may also be co-administered with insulin for the treatment of type I diabetes.

The compounds of the invention can also be co-administered with a therapeutically effective amount of one or more agents used in the prevention or treatment of AIDS, where examples of the agents include, HIV reverse transcriptase inhibitors, HIV protease inhibitors, immunomodulators, and other retroviral drugs. Examples of reverse transcriptase inhibitors include, but are not limited to, abacavir, adefovir, didanosine, dipivoxil delavirdine, efavirenz, emtricitabine, lamivudine, nevirapine, rilpivirine, stavudine, tenofovir, zalcitabine, and zidovudine. Examples of protease inhibitors include, but are not limited to, amprenavir, atazanavir, darunavir, indinavir, fosamprenavir, lopinavir, nelfinavir, ritonavir, saquinavir, and tipranavir. Examples of other retroviral drugs include, but are not limited to, elvitegravir, enfuvirtide, maraviroc and raltegravir.

The compounds of the invention can also be co-administered with a therapeutically effective amount of one or more agents used in the treatment of obesity, where examples of the agents include orlistat.

The compounds of the invention can also be co-administered with a therapeutically effective amount of one or more agents used in the treatment of type II diabetes, where examples of the agents include, alpha glucosidase inhibitors, insulin, metformin, sulfonylureas (e.g., carbutamide, acetohexamide, chlorpropamide, glibenclamide, glibornuride, gliclazide, glimepiride, glipizide, gliquidone, glisoxepide, glyclopyramide, tolbutamide, and tolazamide), nonsulfonylureas (e.g., nateglinide, and repaglinide), and thiazolidinediones (e.g., pioglitazone).

The compounds of the invention can be co-administered with a therapeutically effective amount of one or more agents to prevent or treat type II diabetes, hepatic steatosis, insulin resistance, metabolic syndrome and related disorders, where examples of the agents include, but are not limited to, insulin and insulins that have been modified to improve the duration of action in the body; agents that stimulate insulin secretion such as acetohexamide, chlorpropamide, glyburide, glimepiride, glipizide, glicazide, glycopyramide, gliquidone, rapaglinide, nataglinide, tolazamide and tolbutamide; agents that are glucagon-like peptide agonists such as exanatide, liraglutide and taspoglutide; agents that inhibit dipeptidyl-peptidase IV such as vildagliptin, sitagliptin, saxagliptin, linagliptin, allogliptin and septagliptin; agents that bind to the peroxisome proliferator-activated receptor gamma such as rosiglitazone and pioglitazone; agents that decrease insulin resistance such as metformin; agents that reduce glucose absorbance in the small intestine such as acarbose, miglitol and voglibose.

The compounds of the invention can be co-administered with a therapeutically effective amount of one or more agents to prevent or treat acute kidney disorders and chronic kidney diseases, where examples of the agents include, but are not limited to, dopamine, diuretics such as furosemide, bumetanide, thiazide and the like, mannitol, calcium gluconate, sodium bicarbonate, albuterol, paricalcitol, doxercalciferol, and cinacalcet.

The following Examples may be used for illustrative purposes and should not be deemed to narrow the scope of the invention.

EXAMPLES

Example 1. 3-methyl-1-phenyl-2,5,6,7-tetrahydro-4H-isoindol-4-one

Example 1a. 1-bromo-3-methyl-6,7-dihydro-2H-isoindol-4(5H)-one

A 50 mL roundbottom flask with stirbar was charged with 3-methyl-6,7-dihydro-2H-isoindol-4(5H)-one (Clezy, P. S.; Fookes, C. J. R.; Mirza, A. H. *Aust. J. Chem.* 1977, 30, 1337-47.) (0.502 g, 3.36 mmol) in tetrahydrofuran (8 mL) and cooled to −78° C. under nitrogen. Recrystallized N-bromo succinimide (0.608 g, 3.42 mmol) was added and the mixture stirred for 30 minutes. The reaction mixture was poured into a separatory funnel containing aqueous sodium sulfite and extracted into 100 mL ether. The organics were washed with aqueous sodium bicarbonate and dried over anhydrous sodium sulfate. The crude material was adsorbed on silica gel and chromatographed on a 40 g silica cartridge eluting with 10-100% ethyl acetate/hexanes to provide the title compound.

Example 1b. 3-methyl-1-phenyl-2,5,6,7-tetrahydro-4H-isoindol-4-one

A 5 mL microwave reaction vessel equipped with stirbar was charged with Example 1a (0.0556 g, 0.244 mmol), phenylboronic acid (0.030 g, 0.244 mmol), 2 M aqueous sodium carbonate (1.5 mL, 3.00 mmol) and bis(triphenylphosphine)palladium(II) dichloride (0.171 g, 0.244 mmol) in ethanol (1.2 mL)/DME (1.2 mL) and sealed. The mixture was heated to 120° C. for 30 minutes in a Biotage Initiator 2 monomode microwave reactor, then cooled to ambient temperature. The mixture was shaken in a separatory funnel with 50 mL ethyl acetate and 50 mL water. The organics were dried over anhydrous sodium sulfate. After filtration and solvent removal the residue was purified by reverse phase HPLC (C18, 0-100% $CH_3CN$/water (0.1% TFA)) to afford the title compound. $^1$H NMR (300 MHz, DMSO-$d_6$) δ 11.51 (bs, 1H), 7.50-7.38 (m, 4H), 7.21 (t, J=7.12 Hz, 1H), 2.79 (t, J=6.10 Hz, 2H), 2.51 (s, 3H), 2.33 (m, 2H), 1.94 (m, 2H). MS (DCI+) m/z 226.1 (M+H)$^+$, 243.1 (M+NH$_4$)$^+$.

Example 2. 3-methyl-1-(2-phenoxyphenyl)-2,5,6,7-tetrahydro-4H-isoindol-4-one Example 2 was prepared according to the procedure similar to that used for the preparation of Example 1b, substituting 2-phenoxyphenylboronic acid for phenylboronic acid, to provide the title compound. $^1$H NMR (300 MHz, DMSO-$d_6$) δ 11.34 (bs, 1H), 7.42 (dd, J=7.54, 1.59 Hz, 1H), 7.31 (m, 3H), 7.23 (m, 1H), 7.06 (t, J=7.34 Hz, 1H), 6.93 (m, 3H), 2.59 (m, 1H), 2.54 (s, 3H), 2.26 (m, 2H), 1.85 (m, 2H). MS (ESI+) m/z 318.2 (M+H)$^+$.

Example 3. 1-(2-aminophenyl)-3-methyl-2,5,6,7-tetrahydro-4H-isoindol-4-one

Example 3 was prepared according to the procedure similar to that used for the preparation of Example 1b, substituting 2-aminophenylboronic acid for phenylboronic acid, to provide the title compound. $^1$H NMR (300 MHz, DMSO-$d_6$) δ 11.28 (bs, 1H), 7.17-7.10 (m, 2H), 6.92 (d, J=6.4 Hz, 1H), 6.83 (t, J=7.1 Hz, 1H), 2.56 (t, J=6.15 Hz, 2H), 2.44 (s, 3H), 2.29 (m, 2H), 1.89 (m, 2H). MS (DCI+) m/z 241.1 (M+H)$^+$, 258.1 (M+NH$_4$)$^+$.

Example 4. 3-methyl-1-(4-methylphenyl)-2,5,6,7-tetrahydro-4H-isoindol-4-one

A 4 mL vial was charged with a stirbar, a solution of Example 1a (20 mg, 0.088 mmol) in ethanol (1 mL), a solution of p-tolylboronic acid (16 mg, 1.2 eq, 0.105 mmol) in ethanol (1 mL), an aqueous solution of 1M $Cs_2CO_3$ (180 µL, 2.0 eq, 0.18 mmol), and SiliaCat DPP-Pd resin (Silicycle, Inc.) (32 mg, 0.10 equivalent, 0.27 mmol/g loading). The vial was capped and placed in Anton Paar Synthos 3000 parallel microwave synthesizer at 120° C. for 30 minutes. Upon completion the crude material was filtered, dried, and purified by reverse phase HPLC (C18, 0-100% $CH_3CN$/water (0.1% TFA)) to afford the title compound. $^1$H NMR (300 MHz, DMSO-$d_6$) δ 11.45 (bs, 1H), 7.37 (d, J=8.24 Hz, 2H), 7.21 (d, J=8.24 Hz, 2H), 2.76 (t, J=6.10 Hz, 2H), 2.46 (s, 3H), 2.32 (m, 2H), 2.31 (s, 3H), 1.93 (m, 2H). MS (ESI+) m/z 240.1 (M+H)$^+$.

Example 5. 4-(3-methyl-4-oxo-4,5,6,7-tetrahydro-2H-isoindol-1-yl)benzenesulfonamide Example 5 was prepared according to the procedure similar to that used for the preparation of Example 4, substituting 4-(4,4,5,5-tetramethyl-1,3,2-dioxaborolan-2-yl) benzenesulfonamide for p-tolylboronic acid, to provide the title compound. $^1$H NMR (300 MHz, DMSO-$d_6$) δ 7.85 (d, J=8.8 Hz, 2H), 7.63 (d, J=8.8 Hz, 2H), 2.84 (t, J=6.1 Hz, 2H), 2.50 (s, 3H), 2.37 (m, 2H), 1.97 (m, 2H). MS (ESI+) m/z 305.2 (M+H)$^+$.

Example 6. 1-(2-methoxyphenyl)-3-methyl-2,5,6,7-tetrahydro-4H-isoindol-4-one Example 6 was prepared according to the procedure similar to that used for the preparation of Example 4, substituting 2-methoxyphenylboronic acid for p-tolylboronic acid, to provide the title compound. $^1$H NMR (300 MHz, DMSO-$d_6$) δ 11.19 (bs, 1H), 7.27 (m, 2H), 7.08 (d, J=7.93 Hz, 1H), 7.00 (t, J=7.48 Hz, 1H), 3.80 (s, 3H), 2.58 (t, J=6.10 Hz, 2H), 2.46 (s, 3H), 2.33 (m, 2H), 1.89 (m, 2H). MS (ESI+) m/z 256.1 (M+H)$^+$.

Example 7. 3-methyl-1-(3,4,5-trimethoxyphenyl)-2,5,6,7-tetrahydro-4H-isoindol-4-one Example 7 was prepared according to the procedure similar to that used for the preparation of Example 4, substituting 3,4,5-trimethoxyphenylboronic acid for p-tolylboronic acid, to provide the title compound. $^1$H NMR (300 MHz, DMSO-$d_6$) δ 6.73 (s, 2H), 3.83 (s, 6H), 3.68 (s, 3H), 2.82 (t, J=5.95 Hz, 2H), 2.49 (s, 3H), 2.35 (m, 2H), 1.95 (m, 2H). MS (ESI+) m/z 316.2 (M+H)$^+$.

Example 8. 3-methyl-1-[4-(methylsulfonyl)phenyl]-2,5,6,7-tetrahydro-4H-isoindol-4-one Example 8 was prepared according to the procedure similar to that used for the preparation of Example 4, substituting 4-(methylsulfonyl)phenylboronic acid for p-tolylboronic acid, to provide the title compound. $^1$H NMR (300 MHz, DMSO-$d_6$) δ 7.93 (d, J=8.54 Hz, 2H), 7.72 (d, J=8.54 Hz, 2H), 3.21 (s, 3H), 2.86 (t, J=6.10 Hz, 2H), 2.51 (s, 3H), 2.38 (m, 2H), 1.98 (m, 2H). MS (ESI+) m/z 304.1 (M+H)+.

Example 9. 3-(3-methyl-4-oxo-4,5,6,7-tetrahydro-2H-isoindol-1-yl)benzamide

Example 9 prepared according to the procedure similar to that used for the preparation of Example 4, substituting 3-carbamoylphenylboronic acid for p-tolylboronic acid, to provide the title compound. $^1$H NMR (300 MHz, DMSO-$d_6$) δ 7.96 (s, 1H), 7.69 (d, J=7.63 Hz, 1H), 7.63 (d, J=8.24, 1H), 7.51 (t, J=7.78 Hz, 1H), 2.82 (t, J=5.95 Hz, 2H), 2.49 (s, 3H), 2.36 (m, 2H), 1.96 (m, 2H). MS (ESI+) m/z 269.1 (M+H)+.

Example 10. 1-(1H-indol-4-yl)-3-methyl-2,5,6,7-tetrahydro-4H-isoindol-4-one

Example 10 was prepared according to the procedure similar to that used for the preparation of Example 4, substituting 1H-indol-4-ylboronic acid for p-tolylboronic acid, to provide the title compound. $^1$H NMR (300 MHz, DMSO-$d_6$) δ 11.40 (bs, 1H), 7.38 (m, 2H), 7.16 (m, 1H), 6.97 (d, J=6.41 Hz, 1H), 6.45 (d, J=3.05 Hz, 1H), 2.65 (t, J=6.10 Hz, 2H), 2.51 (s, 3H), 2.37 (m, 2H), 1.91 (m, 2H). MS (ESI+) m/z 265.1 (M+H)+.

Example 11. 1-(4-methoxyphenyl)-3-methyl-2,5,6,7-tetrahydro-4H-isoindol-4-one

Example 11 was prepared according to the procedure similar to that used for the preparation of Example 4, substituting 4-methoxyphenylboronic acid for p-tolylboronic acid, to provide the title compound. $^1$H NMR (300 MHz, DMSO-$d_6$) δ 11.45 (bs, 1H), 7.40 (d, J=8.9 Hz, 2H), 7.00 (d, J=8.9 Hz, 2H), 3.78 (s, 3H), 2.74 (t, J=5.95 Hz, 2H), 2.46 (s, 3H), 2.34 (m, 2H), 1.93 (m, 2H). MS (ESI+) m/z 256.1 (M+H)+.

Example 12. 1-(3,4-dimethylphenyl)-3-methyl-2,5,6,7-tetrahydro-4H-isoindol-4-one Example 12 was prepared according to the procedure similar to that used for the preparation of Example 4, substituting 3,4-dimethylphenylboronic acid for p-tolylboronic acid, to provide the title compound. $^1$H NMR (300 MHz, DMSO-$d_6$) δ 11.47 (bs, 1H), 7.26 (s, 1H), 7.18 (m, 2H), 2.77 (t, J=6.10 Hz, 2H), 2.53 (s, 3H), 2.34 (m, 2H), 2.26 (s, 3H), 2.22 (s, 3H), 1.93 (m, 2H). MS (ESI+) m/z 254.1 (M+H)+.

Example 13. 1-(4-chlorophenyl)-3-methyl-2,5,6,7-tetrahydro-4H-isoindol-4-one

Example 13 was prepared according to the procedure similar to that used for the preparation of Example 4, substituting 4-chlorophenylboronic acid for p-tolylboronic acid, to provide the title compound. $^1$H NMR (300 MHz, DMSO-$d_6$) δ 7.48 (m, 4H), 2.78 (t, J=6.10 Hz, 2H), 2.48 (s, 3H), 2.35 (m, 2H), 1.95 (m, 2H). MS (ESI+) m/z 260.1 (M+H)+.

Example 14. 1-[3-(benzyloxy)phenyl]-3-methyl-2,5,6,7-tetrahydro-4H-isoindol-4-one Example 14 was prepared according to the procedure similar to that used for the preparation of Example 4, substituting 2-(3-(benzyloxy)phenyl)-4,4,5,5-tetramethyl-1,3,2-dioxaborolane for p-tolylboronic acid, to provide the title compound. $^1$H NMR (300 MHz, DMSO-$d_6$) δ 11.56 (bs, 1H), 7.47 (m, 2H), 7.41 (t, J=7.32 Hz, 2H), 7.36-7.31 (m, 2H), 7.07 (m, 2H), 6.88 (m, 1H), 5.17 (s, 2H), 2.73 (t, J=5.95 Hz, 2H), 2.46 (s, 3H), 2.34 (m, 2H), 1.93 (m, 2H). MS (ESI+) m/z 332.1 (M+H)+.

Example 15. 1-(2-chlorophenyl)-3-methyl-2,5,6,7-tetrahydro-4H-isoindol-4-one

Example 15 was prepared according to the procedure similar to that used for the preparation of Example 4, substituting 2-chlorophenylboronic acid for p-tolylboronic acid, to provide the title compound. $^1$H NMR (300 MHz, DMSO-$d_6$) δ 11.49 (bs, 1H), 7.55 (m, 1H), 7.41-7.32 (m, 3H), 2.55 (t, J=6.10 Hz, 2H), 2.46 (s, 3H), 2.34 (m, 2H), 1.91 (m, 2H). MS (ESI+) m/z 260.1 (M+H)+.

Example 16. 1-(1,3-benzodioxol-5-yl)-3-methyl-2,5,6,7-tetrahydro-4H-isoindol-4-one Example 16 was prepared according to the procedure similar to that used for the preparation of Example 4, substituting benzo[d][1,3]dioxol-5-ylboronic acid for p-tolylboronic acid, to provide the title compound. $^1$H NMR (300 MHz, DMSO-$d_6$) δ 11.45 (bs, 1H), 7.01 (d, J=1.2 Hz, 1H), 6.98 (d, J=7.9 Hz, 2H), 6.92 (dd, J=1.2, 7.9 Hz, 1H), 6.02 (s, 2H), 2.73 (t, J=6.0 Hz, 2H), 2.46 (s, 3H), 2.33 (m, 2H), 1.93 (m, 2H). MS (ESI+) m/z 270.1 (M+H)+.

Example 17. 1-(3,5-dimethylphenyl)-3-methyl-2,5,6,7-tetrahydro-4H-isoindol-4-one Example 17 was prepared according to the procedure similar to that used for the preparation of Example 4, substituting 3,5-dimethylphenylboronic acid for p-tolylboronic acid, to provide the title compound. $^1$H NMR (300 MHz, DMSO-$d_6$) δ 11.49 (bs, 1H), 7.09 (s, 2H), 6.87 (s, 1H), 2.78 (t, J=6.10 Hz, 2H), 2.47 (s, 3H), 2.34 (m, 2H), 2.30 (s, 6H), 1.94 (m, 2H). MS (ESI+) m/z 254.1 (M+H)+.

Example 18. 1-[2-(benzyloxy)phenyl]-3-methyl-2,5,6,7-tetrahydro-4H-isoindol-4-one Example 18 was prepared according to the procedure similar to that used for the preparation of Example 4, substituting 2-benzyloxyphenylboronic acid for p-tolylboronic acid, to provide the title compound. $^1$H NMR (300 MHz, DMSO-$d_6$) δ 11.21 (bs, 1H), 7.43 (m, 2H), 7.37 (m, 2H), 7.32 (d, J=7.02 Hz, 1H), 7.28 (ddd, J=1.68, 5.80, 7.48 Hz, 2H), 7.16 (d, J=7.63 Hz, 1H), 7.03 (t, J=7.48 Hz, 1H), 5.13 (s, 2H), 2.56 (t, J=5.95 Hz, 2H), 2.44 (s, 3H), 2.29 (m, 2H), 1.85 (m, 2H). MS (ESI+) m/z 332.2 (M+H)+.

Example 19. 3-methyl-1-(naphthalen-1-yl)-2,5,6,7-tetrahydro-4H-isoindol-4-one

Example 19 was prepared according to the procedure similar to that used for the preparation of Example 4, substituting 1-naphthylboronic acid for p-tolylboronic acid, to provide the title compound. $^1$H NMR (300 MHz, DMSO-$d_6$) δ 11.61 (bs, 1H), 7.99 (m, 1H), 7.94 (d, J=8.24 Hz, 1H), 7.83 (m, 1H), 7.60-7.54 (m, 3H), 7.47 (m, 1H), 2.51 (s, 3H), 2.45 (t, J=5.95 Hz, 2H), 2.38 (m, 2H), 1.92 (m, 2H). MS (ESI+) m/z 278.1 (M+H)+.

Example 20. 1-(3-methoxyphenyl)-3-methyl-2,5,6, 7-tetrahydro-4H-isoindol-4-one Example 20 was prepared according to the procedure similar to that used for the preparation of Example 4, substituting 3-methoxyphenylboronic acid for p-tolylboronic acid, to provide the title compound. $^1$H NMR (300 MHz, DMSO-$d_6$) δ 11.57 (bs, 1H), 7.34 (t, J=7.93 Hz, 1H), 7.06 (m, 1H), 7.02 (m, 1H), 6.81 (dd, J=2.29, 7.78 Hz, 1H), 3.79 (s, 3H), 2.79 (t, J=6.10 Hz, 2H), 2.48 (s, 3H), 2.35 (m, 2H), 1.96 (m, 2H). MS (ESI+) m/z 256.1 (M+H)$^+$.

Example 21. 1-(1H-benzimidazol-4-yl)-3-methyl-2, 5,6,7-tetrahydro-4H-isoindol-4-one Example 21 was prepared according to the procedure similar to that used for the preparation of Example 1b, substituting 1H-benzo[d]imidazol-4-ylboronic acid for phenylboronic acid, to provide the title compound. $^1$H NMR (300 MHz, CDCl$_3$) δ 7.47 (m, 1H), 7.38 (m, 2H), 6.91 (s, 1H), 2.98 (m, 2H), 2.66 (s, 3H), 2.53 (m, 2H), 2.10 (m, 2H). MS (DCI+) m/z 266.1 (M+H)$^+$, 283.3 (M+NH$_4$)$^+$.

Example 22. 1-(1H-indol-7-yl)-3-methyl-2,5,6,7-tetrahydro-4H-isoindol-4-one

Example 22 was prepared according to the procedure similar to that used for the preparation of Example 1b, substituting 1H-indol-7-ylboronic acid for phenylboronic acid, to provide the title compound. $^1$H NMR (300 MHz, CDCl$_3$) δ 8.26 (bs, 1H), 7.64 (d, J=7.54 Hz, 1H), 7.28-7.12 (m, 3H), 6.63 (m, 1H), 2.67 (m, 2H), 2.64 (s, 3H), 2.52 (m, 2H), 2.03 (m, 2H). MS (DCI+) m/z 265.1 (M+H)$^+$, 282.1 (M+NH$_4$)$^+$.

Example 23. 3-methyl-1-(2-{[3-(trifluoromethyl) phenoxy]methyl}phenyl)-2,5,6,7-tetrahydro-4H-isoindol-4-one A 10 mL microwave reaction vessel equipped with stir bar was charged with example 1a (80 mg, 0.351 mmol), 4,4,5, 5-tetramethyl-2-({[(3-trifluoromethyl)phenoxy] methyl}phenyl)-1,3,2-dioxaborolane (141 mg, 0.456 mmol), Na$_2$CO$_3$ (2M, 1.754 mL, 3.51 mmol) and Pd(Ph$_3$P)$_2$Cl$_2$ (14.77 mg, 0.021 mmol) in DME (1.5 mL)/EtOH (1.5 mL) and sealed. The mixture was heated in a Biotage microwave at 120° C. for 30 minutes. The reaction mixture was diluted with ethyl acetate, washed with water (3×25 mL), dried over Na$_2$SO$_4$, filtered through sintered glass funnel and concentrated to give a yellow solid. The sample was transferred in solution onto a 18×150 mm plate. The plate was eluted with 50% ethyl acetate/heptane to give the title compound. $^1$H NMR (400 MHz, DMSO-$d_6$) δ 11.33 (s, 1H), 7.60-7.58 (m, 1H), 7.47 (t, J=8.0 Hz, 1H), 7.42-7.39 (m, 2H), 7.34-7.32 (m, 1H), 7.26 (d, J=8.0 Hz, 1H), 7.17-7.11 (m, 2H), 5.10 (s, 2H), 2.47 (t, J=5.6 Hz, 2H), 2.40 (s, 3H), 2.29 (t, J=5.6 Hz, 2H), 1.86 (qui, J=5.6 Hz, 2H). MS (ESI+) m/z 400.2 (M+H)$^+$.

Example 24. 3-methyl-1-[2-(phenoxymethyl)phenyl]-2,5,6,7-tetrahydro-4H-isoindol-4-one Example 24 was prepared according to the procedure similar to that used for the preparation of Example 23, substituting 4,4,5,5-tetramethyl-2-(2-(phenoxymethyl)phenyl)-1,3,2-dioxaborolane for 4,4,5,5-tetramethyl-2-({[(3-trifluoromethyl)phenoxy]methyl}phenyl)-1,3,2-dioxaborolane, to provide the title compound. $^1$H NMR (400 MHz, CDCl$_3$) δ 9.37 (s, 1H), 7.50-7.43 (m, 3H), 7.36-7.25 (m, 3H), 7.05-7.00 (m, 3H), 4.90 (s, 2H), 2.75 (t, J=6.0 Hz, 2H), 2.47 (t, J=6.0 Hz, 2H), 2.32 (s, 3H), 2.02 (qui, J=6.0 Hz, 2H). MS (ESI+) m/z 331.9 (M+H)$^+$.

Example 25. 3-methyl-1-{2-[(2-methylphenoxy) methyl]phenyl}-2,5,6,7-tetrahydro-4H-isoindol-4-one Example 25 was prepared according to the procedure similar to that used for the preparation of Example 23, substituting 4,4,5,5-tetramethyl-2-({[(2-methyl)phenoxy] methyl}phenyl)-1,3,2-dioxaborolane for 4,4,5,5-tetramethyl-2-({[(3-trifluoromethyl)phenoxy]methyl}phenyl)-1,3, 2-dioxaborolane, to provide the title compound. $^1$H NMR (400 MHz, CDCl$_3$) δ 9.57 (s, 1H), 7.49-7.40 (m, 3H), 7.33-7.29 (m, 1H), 7.20-7.15 (m, 2H), 6.96-6.93 (m, 2H), 4.93 (s, 2H), 2.75 (t, J=6.0 Hz, 2H), 2.47 (t, J=6.0 Hz, 2H), 2.38 (s, 3H), 2.27 (s, 3H), 2.02 (qui, J=6.0 Hz, 2H). MS (ESI+) m/z 346.0 (M+H)$^+$.

Example 26. 2-[2-(3-methyl-4-oxo-4,5,6,7-tetrahydro-2H-isoindol-1-yl)benzyl]-1H-isoindole-1,3 (2H)-dione Example 26 was prepared according to the procedure similar to that used for the preparation of Example 23, substituting 2-(2-(4,4,5,5-tetramethyl-1,3,2-dioxaborolan-2-yl)benzyl)isoindoline-1,3-dione for 4,4,5,5-tetramethyl-2-({[(3-trifluoromethyl)phenoxy]methyl}phenyl)-1,3,2-dioxaborolane, to provide the title compound. $^1$H NMR (400 MHz, CD$_3$OD) δ 7.97 (d, J=7.6 Hz, 1H), 7.62-7.54 (m, 4H), 7.40-7.31 (m, 4H), 4.54 (s, 2H), 2.61 (t, J=6.0 Hz, 2H), 2.56 (s, 3H), 2.47 (t, J=6.0 Hz, 2H), 2.02 (m, 2H). MS (ESI+) m/z 403.2 (M+H$_2$O+H)$^+$.

Example 27. 1-[2-(furan-2-yl)phenyl]-3-methyl-2,5, 6,7-tetrahydro-4H-isoindol-4-one Example 27 was prepared according to the procedure similar to that used for the preparation of Example 23, substituting 2-(2-(furan-2-yl)phenyl)-4,4,5,5-tetramethyl-1, 3,2-dioxaborolane for 4,4,5,5-tetramethyl-2-({[(3-trifluoromethyl)phenoxy]methyl}phenyl)-1,3,2-dioxaborolane, to provide the title compound. $^1$H NMR (400 MHz, CDCl$_3$) δ 7.99 (s, 1H), 7.78 (d, J=8.0 Hz, 1H), 7.42-7.37 (m, 2H), 7.35-7.29 (m, 2H), 6.36 (m, 1H), 5.79 (d, J=2.8 Hz, 1H), 2.54 (s, 3H), 2.51 (t, J=6.0 Hz, 2H), 2.45 (t, J=6.0 Hz, 2H), 2.00 (m, 2H). MS (ESI+) m/z 292.0 (M+H)$^+$.

Example 28. 1-(2-hydroxyphenyl)-3-methyl-2,5,6,7-tetrahydro-4H-isoindol-4-one Example 28 was prepared according to the procedure similar to that used for the preparation of Example 1b, substituting 2-hydroxyphenylboronic acid for phenylboronic acid. Purification by flash chromatography (silica gel, 2-4% methanol in dichloromethane) afforded the title compound (39 mg, 32%). $^1$H NMR (300 MHz, DMSO-$d_6$) δ 11.08 (s, 1H) 9.61 (s, 1H) 7.19 (dd, J=7.46, 1.70 Hz, 1H) 7.04-7.13 (m, 1H) 6.92 (dd, J=7.97, 1.19 Hz, 1H) 6.79-6.86 (m, 1H) 2.61 (t, J=5.93 Hz, 2H) 2.45 (s, 3H) 2.30 (t, J=5.91 Hz, 2H) 1.84-1.95 (m, 2H). MS (ESI+) m/z 242 (M+H)$^+$.

Example 29. 3-methyl-1-[2-(tetrahydrofuran-3-yl-methoxy)phenyl]-2,5,6,7-tetrahydro-4H-isoindol-4-one The product from Example 28 (48.3 mg, 0.20 mmol), (tetrahydrofuran-3-yl)methanol (0.020 mL, 0.210 mmol) and triphenylphosphine (55.1 mg, 0.210 mmol) were combined in tetrahydrofuran (0.1 mL) and sonicated until the solids were dissolved. Diisopropyl azodicarboxylate (0.041 mL, 0.210 mmol) was added and sonication was continued for 2 hours. The reaction mixture was partitioned with ethyl acetate and water. The organic layer was washed with brine, dried with anhydrous sodium sulfate, filtered and concentrated. The residue was purified by flash chromatography (silica gel, 1-2% methanol in dichloromethane) to afford the title compound (13 mg, 20%). $^1$H NMR (300 MHz, DMSO-$d_6$) δ 11.03 (s, 1H) 7.22-7.29 (m, 2H) 7.09 (d, J=7.93 Hz, 1H) 6.96-7.03 (m, 1H) 3.83-4.03 (m, 2H) 3.48-3.76 (m, 4H) 2.55-2.65 (m, 2H) 2.45 (s, 3H) 2.25-2.35 (m, 2H) 1.84-1.94 (m, 2H) 1.56-1.70 (m, 1H) 1.14-1.25 (m, 2H). MS (ESI+) m/z 326 (M+H)$^+$.

Example 30. 1-[2-(cyclopentylmethoxy)phenyl]-3-methyl-2,5,6,7-tetrahydro-4H-isoindol-4-one The product from Example 28 (48.3 mg, 0.20 mmol), (bromomethyl)cyclopentane (39.1 mg, 0.240 mmol) and potassium carbonate (33.2 mg, 0.240 mmol) were combined in dimethylformamide (1 mL) and heated at 50° C. for 16 hours. The reaction mixture was partitioned with ethyl acetate and water. The organic layer was concentrated and the residue was purified by reverse phase HPLC (C18, 50-95% acetonitrile in 10 mM ammonium acetate/water) to afford the title compound (31 mg, 48%). $^1$H NMR (300 MHz, DMSO-$d_6$) δ11.01 (s, 1H) 7.20-7.28 (m, 2H) 7.04-7.10 (m, 1H) 6.93-7.01 (m, 1H) 3.85 (d, J=6.74 Hz, 2H) 2.59 (t, J=5.95 Hz, 2H) 2.43 (s, 3H) 2.23-2.36 (m, 3H) 1.83-1.94 (m, 2H) 1.62-1.76 (m, 2H) 1.43-1.60 (m, 4H) 1.24-1.38 (m, 2H). MS (ESI+) m/z 324 (M+H)$^+$.

Example 31. 3-methyl-1-[2-(tetrahydrofuran-2-yl-methoxy)phenyl]-2,5,6,7-tetrahydro-4H-isoindol-4-one Example 31 was prepared according to the procedure similar to that used for the preparation of Example 30, substituting 2-(bromomethyl)tetrahydrofuran for (bromomethyl)cyclopentane, to provide the title compound (24 mg, 37%). $^1$H NMR (300 MHz, DMSO-$d_6$) δ 11.07 (s, 1H) 7.19-7.33 (m, 2H) 7.07-7.15 (m, 1H) 6.93-7.06 (m, 1H) 4.16-4.27 (m, 1H) 4.06-4.15 (m, 1H) 3.87-3.96 (m, 1H) 3.62-3.83 (m, 2H) 2.65 (t, J=6.15 Hz, 2H) 2.45 (s, 3H) 2.28-2.35 (m, 2H) 1.79-2.01 (m, 5H) 1.61-1.73 (m, 1H). MS (ESI+) m/z 326 (M+H)$^+$.

Example 32. 3-methyl-1-[2-(tetrahydro-2H-pyran-4-ylmethoxy)phenyl]-2,5,6,7-tetrahydro-4H-isoindol-4-one Example 32 was prepared according to the procedure similar to that used for the preparation of Example 30, substituting 4-(bromomethyl)tetrahydro-2H-pyran for (bromomethyl)cyclopentane, to provide the title compound (41 mg, 60%). $^1$H NMR (300 MHz, DMSO-$d_6$) δ 11.05 (s, 1H) 7.20-7.29 (m, 2H) 7.03-7.11 (m, 1H) 6.94-7.02 (m, 1H) 3.79-3.89 (m, 4H) 3.21-3.30 (m, 2H) 2.58 (t, J=5.95 Hz, 2H) 2.43 (s, 3H) 2.26-2.33 (m, 2H) 1.96-2.07 (m, 1H) 1.84-1.94 (m, 2H) 1.55-1.64 (m, 2H) 1.17-1.35 (m, 2H). MS (ESI+) m/z 340 (M+H)$^+$.

Example 33. 3-methyl-1-{2-[2-(morpholin-4-yl)ethoxy]phenyl}-2,5,6,7-tetrahydro-4H-isoindol-4-one Example 33 was prepared according to the procedure similar to that used for the preparation of Example 30, substituting 4-(2-bromoethyl)morpholine for (bromomethyl)cyclopentane, to provide the title compound (46 mg, 65%). $^1$H NMR (300 MHz, DMSO-$d_6$) δ 11.06 (s, 1H) 7.17-7.32 (m, 2H) 7.06-7.14 (m, 1H) 6.92-7.04 (m, 1H) 4.13 (t, J=5.59 Hz, 2H) 3.51-3.57 (m, 4H) 2.70 (t, J=5.59 Hz, 2H) 2.64 (t, J=6.10 Hz, 2H) 2.47 (s, 3H) 2.39-2.44 (m, 4H) 2.28-2.34 (m, 2H) 1.84-1.95 (m, 2H). MS (ESI+) m/z 355 (M+H)$^+$.

Example 34. 3-methyl-1-[2-(pyridin-2-ylmethoxy)phenyl]-2,5,6,7-tetrahydro-4H-isoindol-4-one Example 34 was prepared according to the procedure similar to that used for the preparation of Example 30, substituting 2-(bromomethyl)pyridine hydrobromide for (bromomethyl)cyclopentane and the reaction was performed at room temperature instead of 50° C., to provide the title compound (52 mg, 78%). $^1$H NMR (300 MHz, DMSO-$d_6$) δ 11.63 (s, 1H) 8.58-8.64 (m, 1H) 7.79-7.90 (m, 1H) 7.48 (d, J=8.14 Hz, 1H) 7.31-7.40 (m, 2H) 7.16-7.29 (m, 2H) 6.98-7.07 (m, 1H) 5.28 (s, 2H) 2.66 (t, J=5.93 Hz, 2H) 2.49 (s, 3H) 2.28-2.34 (m, 2H) 1.83-1.95 (m, 2H). MS (ESI+) m/z 333 (M+H)$^+$.

Example 35. 3-methyl-1-[2-(quinolin-8-ylmethoxy)phenyl]-2,5,6,7-tetrahydro-4H-isoindol-4-one Example 35 was prepared according to the procedure similar to that used for the preparation of Example 30, substituting 8-(bromomethyl)quinoline for (bromomethyl)cyclopentane and the reaction was performed at room temperature instead of 50° C., to provide the title compound (48 mg, 63%). $^1$H NMR (300 MHz, DMSO-$d_6$) δ 11.16 (s, 1H) 8.99 (dd, J=4.24, 1.86 Hz, 1H) 8.44 (dd, J=8.48, 1.70 Hz, 1H) 7.98 (dd, J=8.14, 1.36 Hz, 1H) 7.85 (dd, J=6.95, 1.19 Hz, 1H) 7.57-7.66 (m, 2H) 7.21-7.34 (m, 3H) 6.98-7.07 (m, 1H) 5.78 (s, 2H) 2.57 (t, J=5.93 Hz, 2H) 2.37 (s, 3H) 2.20-2.28 (m, 2H) 1.72-1.84 (m, 2H). MS (ESI+) m/z 383 (M+H)$^+$.

Example 36. 1-[2-(1-benzothiophen-7-ylmethoxy)phenyl]-3-methyl-2,5,6,7-tetrahydro-4H-isoindol-4-one Example 36 was prepared according to the procedure similar to that used for the preparation of Example 30, substituting 7-(bromomethyl)benzo[b]thiophene for (bromomethyl)cyclopentane and the reaction was performed at room temperature instead of 50° C., to provide the title compound (39 mg, 50%). $^1$H NMR (300 MHz, DMSO-$d_6$) δ 11.12 (s, 1H) 7.86 (dd, J=7.46, 1.36 Hz, 1H) 7.76 (d, J=5.43 Hz, 1H) 7.50 (d, J=5.43 Hz, 1H) 7.35-7.48 (m, 2H) 7.21-7.33 (m, 3H) 6.98-7.08 (m, 1H) 5.39 (s, 2H) 2.54 (t, J=5.76 Hz, 2H) 2.40 (s, 3H) 2.21-2.27 (m, 2H) 1.75-1.83 (m, 2H). MS (ESI+) m/z 388 (M+H)$^+$.

Example 37. 3-methyl-1-[2-(pyridin-3-ylmethoxy)phenyl]-2,5,6,7-tetrahydro-4H-isoindol-4-one Example 37 was prepared according to the procedure similar to that used for the preparation of Example 30, substituting 3-(bromomethyl)pyridine hydrobromide for (bromomethyl)cyclopentane and the reaction was performed at room temperature instead of 50° C., to provide the title compound (8 mg, 12%). $^1$H NMR (300 MHz, DMSO-$d_6$) δ 11.20 (s, 1H) 8.64 (d, J=1.70 Hz, 1H) 8.52 (dd, J=4.75, 1.70 Hz, 1H) 7.74-7.88 (m, 1H) 7.40 (dd, J=7.80, 5.09 Hz, 1H) 7.25-7.33 (m, 2H) 7.15-7.21 (m, 1H) 6.95-7.08 (m, 1H) 5.17 (s, 2H) 2.54 (t, J=5.76, 2H) 2.43 (s, 3H) 2.23-2.30 (m, 2H) 1.76-1.91 (m, 2H). MS (ESI+) m/z 333 (M+H)$^+$.

Example 38. 1-[2-(1H-indazol-5-ylmethoxy)phenyl]-3-methyl-2,5,6,7-tetrahydro-4H-isoindol-4-one Example 38 was prepared according to the procedure similar to that used for the preparation of Example 30, substituting 5-(bromomethyl)-1H-indazole hydrobromide for (bromomethyl)cyclopentane and the reaction was performed at room temperature instead of 50° C., to provide the title compound (8 mg, 11%). $^1$H NMR (300 MHz, DMSO-$d_6$) δ 13.06 (s, 1H) 11.17 (s, 1H) 8.03 (s, 1H) 7.79 (s, 1H) 7.48-7.56 (m, 1H) 7.39-7.46 (m, 1H) 7.17-7.31 (m, 3H) 6.96-7.05 (m, 1H) 5.20 (s, 2H) 2.55 (t, J=6.10 Hz, 2H) 2.43 (s, 3H) 2.20-2.27 (m, 2H) 1.75-1.87 (m, 2H). MS (ESI+) m/z 372 (M+H)$^+$.

Example 39. 1-(5-amino-2-phenoxyphenyl)-3-methyl-2,5,6,7-tetrahydro-4H-isoindol-4-one

Example 39a. 1-(2-fluoro-5-nitrophenyl)-3-methyl-6,7-dihydro-2H-isoindol-4(5H)-one A 250 mL three-necked round-bottomed flask containing Example 1a (2.97 g, 13 mmol), 2-fluoro-5-nitrophenylboronic acid (3.61 g, 19.50 mmol), Pd$_2$(dba)$_3$ (0.298 g, 0.325 mmol), 1,3,5,7-tetramethyl-6-phenyl-2,4,8-trioxa-6-phosphaadamante (0.190 g, 0.650 mmol) and potassium phosphate (8.28 g, 39.0 mmol) was purged with nitrogen for 30 minutes. Nitrogen-purged 1,4-dioxane (50 mL) was then transferred to the three-necked round-bottomed flask and the mixture was heated at 60° C. for 6 hours. The reaction mixture was then cooled to room temperature and partitioned between ethyl acetate and water. The organic layer was washed with brine, dried over anhydrous sodium sulfate and filtered. The filtrate was treated with 3-mercaptopropyl-functionalized silica gel, filtered and concentrated. The residue was purified by flash chromatography (silica gel, 0-20% ethyl acetate in dichloromethane) to afford 2.66 g (71%) of the title compound.

Example 39b. 3-methyl-1-(5-nitro-2-phenoxyphenyl)-6,7-dihydro-2H-isoindol-4(5H)-one Example 39a (2.65 g, 9.19 mmol), phenol (0.952 g, 10.11 mmol), and Cs$_2$CO$_3$ (5.99 g, 18.39 mmol) were combined with dimethylformamide (30 mL) and stirred at 50° C. for 1 hour. The reaction mixture was cooled to room temperature and partitioned between ethyl acetate and water. The organic layer was washed with brine twice, dried over anhydrous sodium sulfate, filtered and concentrated. The residue was purified by flash chromatography (silica gel, 0-20% ethyl acetate in dichloromethane) to afford 3.33 g (100%) of the title compound.

Example 39c. 1-(5-amino-2-phenoxyphenyl)-3-methyl-2,5,6,7-tetrahydro-4H-isoindol-4-one To a mixture of Example 39b (3.33 g, 9.19 mmol), iron powder (2.57 g, 45.9 mmol) and ammonium chloride (1.475 g, 27.6 mmol) was added a solution of tetrahydrofuran (24 mL)/ethanol (24 mL)/water (8 mL). The resulting mixture was heated under reflux for 9 hours, then cooled to room temperature and partitioned between ethyl acetate and water. The organic layer was washed with brine, dried over anhydrous sodium sulfate, filtered and concentrated. The residue was purified by flash chromatography (silica gel, 20-40% ethyl acetate in dichloromethane) to afford 2.78 g (91%) of the title compound. $^1$H NMR (300 MHz, DMSO-$d_6$) δ 11.22 (s, 1H), 7.19 (m, 2H), 6.88 (m, 1H), 6.79 (d, J=8.48 Hz, 1H), 6.72 (m, 2H), 6.62 (d, J=2.71 Hz, 1H), 6.54 (dd, J=8.82, 2.71 Hz, 1H), 5.06 (s, 2H), 2.56 (t, J=5.93 Hz, 2H), 2.35 (s, 3H), 2.22 (m, 2H), 1.81 (m, 2H). MS (ESI+) m/z 333 [M+H]$^+$.

Example 40. N-[3-(3-methyl-4-oxo-4,5,6,7-tetrahydro-2H-isoindol-1-yl)-4-phenoxyphenyl]methanesulfonamide Example 39c (2.78 g, 8.36 mmol), methanesulfonyl chloride (1.564 mL, 20.07 mmol) and triethylamine (3.48 mL, 25.09 mmol) were combined in dichloromethane (40 mL). The reaction mixture was stirred at room temperature for 1 hour and concentrated. The residue was diluted with dioxane (40 mL) and sodium hydroxide (84 mL of 1.0 M aqueous solution, 84 mmol) and heated at 50° C. for 1 hour. The reaction mixture was partitioned with ethyl acetate and saturated aqueous ammonium chloride solution. The organic layer was washed with brine, dried with anhydrous sodium sulfate, filtered and concentrated. The residue was purified by flash chromatography (silica gel, 1-2% methanol in dichloromethane) followed by trituration (dichloromethane) to afford the title compound (3.05 g, 89%). $^1$H NMR (300 MHz, DMSO-$d_6$) δ 11.35 (s, 1H) 9.71 (s, 1H) 7.25-7.34 (m, 3H) 7.10-7.16 (m, 1H) 7.00-7.07 (m, 1H) 6.97 (d, J=8.82 Hz, 1H) 6.86-6.92 (m, 2H) 3.02 (s, 3H) 2.60 (t, J=5.93 Hz, 2H) 2.41 (s, 3H) 2.27 (t, J=6.10 Hz, 2H) 1.80-1.93 (m, 2H). MS (ESI+) m/z 411 (M+H)$^+$.

Example 41. N-[3-(2,3-dimethyl-4-oxo-4,5,6,7-tetrahydro-2H-isoindol-1-yl)-4-phenoxyphenyl]methanesulfonamide

Example 41a. 2,3-dimethyl-1-(5-nitro-2-phenoxyphenyl)-6,7-dihydro-2H-isoindol-4(5H)-one Example 39b (127 mg, 0.350 mmol) in tetrahydrofuran (2 mL) was treated with 60% sodium hydride (15.42 mg, 0.386 mmol), stirred at room temperature for 1 hour, treated with iodomethane (0.024 mL, 0.386 mmol) and stirred at room temperature for 2 hours. The reaction mixture was partitioned with ethyl acetate and water. The organic layer was washed with brine, dried with anhydrous sodium sulfate, filtered and concentrated. The residue was purified by flash chromatography (silica gel, 0-2% methanol in dichloromethane) to afford the title compound (105 mg, 80%).

Example 41b. 1-(5-amino-2-phenoxyphenyl)-2,3-dimethyl-6,7-dihydro-2H-isoindol-4(5H)-one Example 41b was prepared according to the procedure similar to that used for the preparation of Example 39c, substituting Example 41a for Example 39b, to provide the title compound (90 mg, 95%).

Example 41c. N-[3-(2,3-dimethyl-4-oxo-4,5,6,7-tetrahydro-2H-isoindol-1-yl)-4-phenoxyphenyl]methanesulfonamide Example 41c was prepared according to the procedure similar to that used for the preparation of Example 40, substituting Example 41b for Example 39c. Purification by flash chromatography (silica gel, 2% methanol in dichloromethane) afforded the title compound (43 mg, 84%). $^1$H NMR (300 MHz, DMSO-$d_6$) δ9.75 (s, 1H) 7.19-7.29 (m, 3H) 7.16 (d, J=2.78 Hz, 1H) 7.07 (d, J=8.73 Hz, 1H) 7.00 (t, J=7.34 Hz, 1H) 6.81 (d, J=7.54 Hz, 2H) 3.33 (s, 3H) 3.02 (s, 3H) 2.44 (s, 3H) 2.18-2.37 (m, 4H) 1.66-1.90 (m, 2H). MS (ESI+) m/z 425 (M+H)$^+$.

Example 42. N-[3-(2,3-dimethyl-4-oxo-4,5,6,7-tetrahydro-2H-isoindol-1-yl)-4-phenoxyphenyl]acetamide Example 41b (41.6 mg, 0.12 mmol) in acetic anhydride (0.5 mL, 5.30 mmol) was heated in microwave at 100° C. for 30 minutes. The reaction mixture was concentrated and the residue was purified by flash chromatography (silica gel, 1-2% methanol in dichloromethane) to afford the title compound (38 mg, 82%). $^1$H NMR (300 MHz, DMSO-$d_6$) δ 10.04 (s, 1H) 7.51-7.67 (m, 2H) 7.16-7.30 (m, 2H) 6.93-7.08 (m, 2H) 6.74-6.80 (m, 2H) 3.30 (s, 3H) 2.43 (s, 3H) 2.12-2.35 (m, 4H) 2.05 (s, 3H) 1.77-1.88 (m, 1H) 1.66-1.76 (m, 1H). MS (ESI+) m/z 389 (M+H)$^+$.

Example 43. 1-[5-amino-2-(phenylsulfanyl)phenyl]-3-methyl-2,5,6,7-tetrahydro-4H-isoindol-4-one Example 43a. 3-methyl-1-(5-nitro-2-(phenylthio)phenyl)-6,7-dihydro-2H-isoindol-4(5H)-one Example 39a (58 mg, 0.201 mmol) and sodium thiophenoxide (29.2 mg, 0.221 mmol) were combined in dimethylformamide (2 mL) and heated at 50° C. for 2 hours. The reaction mixture was partitioned with ethyl acetate and water. The organic layer was washed with brine twice, dried with anhydrous sodium sulfate, filtered and concentrated. The residue was purified by flash chromatography (silica gel, 0-1% methanol in dichloromethane) to afford the title compound (46 mg, 60%).

Example 43b. 1-[5-amino-2-(phenylsulfanyl)phenyl]-3-methyl-2,5,6,7-tetrahydro-4H-isoindol-4-one Example 43b was prepared according to the procedure similar to that used for the preparation of Example 39c, substituting Example 43a for Example 39b. Purification by flash chromatography (silica gel, 2% methanol in dichloromethane) afforded the title compound (35 mg. 84%). $^1$H NMR (300 MHz, DMSO-$d_6$) δ 11.25 (s, 1H) 7.10-7.24 (m, 3H) 6.98-7.06 (m, 1H) 6.81-6.88 (m, 2H) 6.54-6.61 (m, 2H) 5.53 (s, 2H) 2.41 (t, J=5.93 Hz, 2H) 2.37 (s, 3H) 2.19-2.26 (m, 2H) 1.73-1.83 (m, 2H). MS (ESI+) m/z 349 (M+H)$^+$.

Example 44. N-[3-(3-methyl-4-oxo-4,5,6,7-tetrahydro-2H-isoindol-1-yl)-4-(phenylsulfanyl)phenyl]methanesulfonamide Example 44 was prepared according to the procedure similar to that used for the preparation of Example 40, substituting Example 43b for Example 39c. Purification by flash chromatography (silica gel, 2% methanol in dichloromethane) afforded the title compound (33 mg, 84%). $^1$H NMR (300 MHz, DMSO-$d_6$) δ11.40 (s, 1H) 9.96 (s, 1H) 7.18-7.31 (m, 4H) 7.08-7.16 (m, 4H) 3.06 (s, 3H) 2.41-2.48 (m, 5H) 2.23-2.31 (m, 2H) 1.80-1.87 (m, 2H). MS (ESI+) m/z 427 (M+H)$^+$.

Example 45. 1-[5-amino-2-(2,4-difluorophenoxy)phenyl]-3-methyl-2,5,6,7-tetrahydro-4H-isoindol-4-one Example 45a. 1-(2-(2,4-difluorophenoxy)-5-nitrophenyl)-3-methyl-6,7-dihydro-2H-isoindol-4(5H)-one Example 45a prepared according to the procedure similar to that used for the preparation of Example 39b, substituting 2,4-difluorophenol for phenol, to provide the title compound (1.01 g, 73%).

Example 45b. 1-[5-amino-2-(2,4-difluorophenoxy)phenyl]-3-methyl-2,5,6,7-tetrahydro-4H-isoindol-4-one Example 45b was prepared according to the procedure similar to that used for the preparation of Example 39c, substituting Example 45a for Example 39b, to provide the title compound (805 mg, 87%). $^1$H NMR (300 MHz, DMSO-$d_6$) δ 11.24 (s, 1H) 7.22-7.33 (m, 1H) 6.83-6.94 (m, 1H) 6.64-6.77 (m, 2H) 6.60 (d, J=2.71 Hz, 1H) 6.49-6.56 (m, 1H) 5.07 (s, 2H) 2.54 (t, J=5.76 Hz, 2H) 2.37 (s, 3H) 2.24 (t, J=5.76 Hz, 2H) 1.76-1.87 (m, 2H). MS (ESI+) m/z 369 (M+H)$^+$.

Example 46. N-[4-(2,4-difluorophenoxy)-3-(3-methyl-4-oxo-4,5,6,7-tetrahydro-2H-isoindol-1-yl)phenyl]methanesulfonamide Example 46 was prepared according to the procedure similar to that used for the preparation of Example 40, substituting Example 45b for Example 39c. Purification by flash chromatography (silica gel, 1-2% methanol in dichloromethane) afforded the title compound (49 mg, 81%). $^1$H NMR (300 MHz, DMSO-$d_6$) δ 11.36 (s, 1H) 9.68 (s, 1H) 7.34-7.47 (m, 1H) 7.25 (d, J=2.71 Hz, 1H) 6.99-7.16 (m, 3H) 6.83 (d, J=8.48 Hz, 1H) 3.01 (s, 3H) 2.60 (t, J=5.93 Hz, 2H) 2.44 (s, 3H) 2.25-2.33 (m, 2H) 1.79-1.93 (m, 2H). MS (ESI+) m/z 447 (M+H)$^+$.

Example 47. N-[4-(2,4-difluorophenoxy)-3-(3-methyl-4-oxo-4,5,6,7-tetrahydro-2H-isoindol-1-yl)phenyl]ethanesulfonamide Example 47 was prepared according to the procedure similar to that used for the preparation of Example 40, substituting Example 45b for Example 39c, and ethanesulfonyl chloride for methanesulfonyl chloride, respectively. Purification by flash chromatography (silica gel, 1-2% methanol in dichloromethane) afforded the title compound (53 mg, 85%). $^1$H NMR (300 MHz, DMSO-$d_6$) δ 11.35 (s, 1H) 9.75 (s, 1H) 7.34-7.48 (m, 1H) 7.25 (d, J=2.37 Hz, 1H) 6.96-7.16 (m, 3H) 6.82 (d, J=8.82 Hz, 1H) 3.10 (q, J=7.23 Hz, 2H) 2.59 (t, J=5.93 Hz, 2H) 2.44 (s, 3H) 2.24-2.33 (m, 2H) 1.80-1.92 (m, 2H) 1.22 (t, J=7.29 Hz, 3H). MS (ESI+) m/z 461 (M+H)$^+$.

Example 48. N-[4-(2,4-difluorophenoxy)-3-(3-methyl-4-oxo-4,5,6,7-tetrahydro-2H-isoindol-1-yl)phenyl]-2,2,2-trifluoromethanesulfonamide Example 45b (50 mg, 0.136 mmol), 2,2,2-trifluoroethanesulfonyl chloride (29.7 mg, 0.163 mmol), and triethylamine (0.057 mL, 0.407 mmol) were combined in dichloromethane (2 mL). The reaction mixture was stirred at room temperature for 2 hours, concentrated, and the residue was partitioned with ethyl acetate and water. The organic layer was washed with brine, dried with anhydrous sodium sulfate, filtered and concentrated. The residue was purified by flash chromatography (silica gel, 1-2% methanol in dichloromethane) to afford the title compound (18 mg, 26%). $^1$H NMR (300 MHz, DMSO-$d_6$) δ 11.35 (s, 1H) 10.40 (s, 1H) 7.35-7.49 (m, 1H) 7.26 (d, J=2.71 Hz, 1H) 7.00-7.18 (m, 3H) 6.83 (d, J=8.82 Hz, 1H) 4.53 (q, J=9.83 Hz, 2H) 2.60 (t, J=5.93 Hz, 2H) 2.45 (s, 3H) 2.25-2.34 (m, 2H) 1.81-1.94 (m, 2H). MS (ESI+) m/z 515 (M+H)$^+$.

Example 49. N'-[4-(2,4-difluorophenoxy)-3-(3-methyl-4-oxo-4,5,6,7-tetrahydro-2H-isoindol-1-yl)phenyl]-N,N-dimethylsulfuric Diamide Example 45b (50 mg, 0.136 mmol), dimethylsulfamoyl chloride (0.017 mL, 0.163 mmol), and cesium carbonate (66.3 mg, 0.204 mmol) were combined in dimethylformamide (1 mL) and the reaction mixture was heated by microwave at 80° C. for 1 hour. Dimethylsulfamoyl chloride (0.017 mL, 0.163 mmol) was added again and the reaction mixture was heated by microwave at 80° C. for another 1 hour. The reaction mixture was partitioned with ethyl acetate and water. The organic layer was washed with brine twice, dried with anhydrous sodium sulfate, filtered and concentrated. The residue was purified by flash chromatography (silica gel, 1-2% methanol in dichloromethane) to afford the title compound (14 mg, 22%). $^1$H NMR (300 MHz, DMSO-$d_6$) δ 11.33 (s, 1H) 9.87 (s, 1H) 7.32-7.50 (m, 1H) 7.23 (d, J=2.78 Hz, 1H) 6.94-7.18 (m, 3H) 6.81 (d, J=8.73 Hz, 1H) 2.71 (s, 6H) 2.59 (t, J=5.95 Hz, 2H) 2.43 (s, 3H) 2.25-2.32 (m, 2H) 1.82-1.92 (m, 2H). MS (ESI+) m/z 476 (M+H)$^+$.

Example 50. N-[4-(2,4-difluorophenoxy)-3-(3-methyl-4-oxo-4,5,6,7-tetrahydro-2H-isoindol-1-yl)phenyl]acetamide Example 50 was prepared according to the procedure similar to that used for the preparation of Example 42, substituting Example 45b for Example 41b, to afford the title compound (35 mg, 63%). $^1$H NMR (300 MHz, DMSO-$d_6$) δ 11.33 (s, 1H) 9.98 (s, 1H) 7.68 (d, J=2.71 Hz, 1H) 7.28-7.49 (m, 2H) 6.92-7.12 (m, 2H) 6.82 (d, J=8.82 Hz, 1H) 2.59 (t, J=5.76 Hz, 2H) 2.42 (s, 3H) 2.24-2.32 (m, 2H) 2.04 (s, 3H) 1.81-1.92 (m, 2H). MS (ESI+) m/z 411 (M+H)$^+$.

Example 51. N-[4-(2,4-difluorophenoxy)-3-(3-methyl-4-oxo-4,5,6,7-tetrahydro-2H-isoindol-1-yl)phenyl]-1H-pyrrole-2-carboxamide 1H-pyrrole-2-carboxylic acid (18.10 mg, 0.163 mmol) in tetrahydrofuran (2 mL) was treated with oxalyl dichloride (0.024 mL, 0.271 mmol) and one drop of dimethylformamide. The reaction mixture was stirred at room temperature for 30 minutes and concentrated. The residue was azeotroped with toluene and dissolved in tetrahydrofuran (2 mL). Example 45b (50 mg, 0.136 mmol) and triethylamine (0.076 mL, 0.543 mmol) were added and the reaction mixture was stirred at room temperature for 30 minutes. The reaction mixture was partitioned with ethyl acetate and water. The organic layer was washed with brine, dried with anhydrous sodium sulfate, filtered and concentrated. The residue was purified by flash chromatography (silica gel, 1-2% methanol in dichloromethane) to afford the title compound (40 mg, 64%). $^1$H NMR (300 MHz, DMSO-$d_6$) δ 11.66 (s, 1H) 11.36 (s, 1H) 9.80 (s, 1H) 7.88 (d, J=2.38 Hz, 1H) 7.60 (dd, J=8.93, 2.58 Hz, 1H) 7.32-7.46 (m, 1H) 7.02-7.08 (m, 3H) 6.93-6.98 (m, 1H) 6.86 (d, J=8.73 Hz, 1H) 6.13-6.20 (m, 1H) 2.64 (t, J=5.95 Hz, 2H) 2.43 (s, 3H) 2.24-2.34 (m, 2H) 1.82-1.94 (m, 2H). MS (ESI+) m/z 462 (M+H)$^+$.

Example 52. N-{4-[(4,4-difluorocyclohexyl)oxy]-3-(3-methyl-4-oxo-4,5,6,7-tetrahydro-2H-isoindol-1-yl)phenyl}ethanesulfonamide

Example 52a. 1-(2-(4,4-difluorocyclohexyloxy)-5-nitrophenyl)-3-methyl-6,7-dihydro-2H-isoindol-4(5H)-one To 4,4-difluorocyclohexanol (102 mg, 0.75 mmol) in tetrahydrofuran (2 mL) was added 60% sodium hydride (36 mg, 0.90 mmol) under nitrogen and the reaction mixture was stirred at room temperature for 1 hour. Example 39a (43.2 mg, 0.15 mmol) was added and the reaction mixture was heated at 50° C. under nitrogen for 2 hours. The reaction mixture was partitioned with ethyl acetate and 1M HCl. The organic layer was washed with brine, dried with anhydrous sodium sulfate, filtered and concentrated. The residue was purified by flash chromatography (silica gel, 5-20% ethyl acetate in dichloromethane), followed by trituration (10% dichloromethane in hexane) to afford the title compound (32 mg, 53%).

Example 52b. 1-(5-amino-2-(4,4-difluorocyclohexyloxy)phenyl)-3-methyl-6,7-dihydro-2H-isoindol-4(5H)-one Example 52a (58 mg, 0.143 mmol) and 10% palladium on carbon (30.5 mg, 0.029 mmol) were combined in ethyl acetate (20 mL). The reaction mixture was hydrogenated under a hydrogen balloon atmosphere for 3 hours, filtered and the filtrate was concentrated to afford the title compound (49 mg, 91%).

Example 52c. N-{4-[(4,4-difluorocyclohexyl)oxy]-3-(3-methyl-4-oxo-4,5,6,7-tetrahydro-2H-isoindol-1-yl)phenyl}ethanesulfonamide Example 52c was prepared according to the procedure similar to that used for the preparation of Example 40, substituting Example 52b for Example 39c, and ethanesulfonyl chloride for methanesulfonyl chloride, respectively. Purification by flash chromatography (silica gel, 1-2% methanol in dichloromethane) and trituration (20% dichloromethane in hexane) afforded the title compound (44 mg, 77%). $^1$H NMR (300 MHz, DMSO-$d_6$) δ 11.16 (s, 1H) 9.57 (s, 1H) 7.05-7.22 (m, 3H) 4.38-4.51 (m, 1H) 3.04 (q, J=7.54 Hz, 2H) 2.57 (t, J=5.75 Hz, 2H) 2.44 (s, 3H) 2.29-2.36 (m, 2H) 1.71-1.92 (m, 10H) 1.21 (t, J=7.34 Hz, 3H). MS (ESI+) m/z 467 (M+H)$^+$.

Example 53. methyl 3-(3-methyl-4-oxo-4,5,6,7-tetrahydro-2H-isoindol-1-yl)-4-phenoxybenzoate

Example 53a. methyl 4-fluoro-3-(3-methyl-4-oxo-4,5,6,7-tetrahydro-2H-isoindol-1-yl)benzoate Example 53a prepared according to the procedure similar to that used for the preparation of Example 39a, substituting (2-fluoro-5-methoxycarbonylphenyl)boronic acid for 2-fluoro-5-nitrophenylboronic acid. Purification by flash chromatography (silica gel, 0-60% ethyl acetate in hexane) afforded the title compound (3.8 g, 72%).

Example 53b. methyl 3-(3-methyl-4-oxo-4,5,6,7-tetrahydro-2H-isoindol-1-yl)-4-phenoxybenzoate Example 53b was prepared according to the procedure similar to that used for the preparation of Example 39b, substituting Example 53a for Example 39a and the reaction was performed at 120° C. instead of 50° C., to provide the title compound (451 mg, 60%). $^1$H NMR (300 MHz, DMSO-$d_6$) δ 11.50 (s, 1H) 7.99 (d, J=2.03 Hz, 1H) 7.84 (dd, J=8.65, 2.20 Hz, 1H) 7.38-7.48 (m, 2H) 7.17-7.25 (m, 1H) 7.08-7.15 (m, 2H) 6.89 (d, J=8.48 Hz, 1H) 3.85 (s, 3H) 2.62 (t, J=5.93 Hz, 2H) 2.46 (s, 3H) 2.25-2.33 (m, 2H) 1.83-1.93 (m, 2H). MS (ESI+) m/z 376 (M+H)$^+$.

Example 54. 3-(3-methyl-4-oxo-4,5,6,7-tetrahydro-2H-isoindol-1-yl)-4-phenoxybenzoic Acid A mixture of Example 53b (410 mg, 1.092 mmol) and sodium hydroxide (3.28 mL of 1.0 M aqueous solution, 3.28 mmol) in tetrahydrofuran (10 mL) and water (5 mL) was heated at reflux for 2 hours. The reaction mixture was partitioned with ethyl acetate and water. The aqueous layer was acidified to pH 1 with 1M HCl, extracted with ethyl acetate, dried with anhydrous sodium sulfate, filtered and concentrated to provide the title compound (385 mg, 98%). $^1$H NMR (300 MHz, DMSO-$d_6$) δ 12.83 (s, 1H) 11.47 (s, 1H) 7.98 (d, J=2.03 Hz, 1H) 7.82 (dd, J=8.48, 2.37 Hz, 1H) 7.38-7.48 (m, 2H) 7.16-7.23 (m, 1H) 7.06-7.12 (m, 2H) 6.88 (d, J=8.82 Hz, 1H) 2.62 (t, J=5.93 Hz, 2H) 2.45 (s, 3H) 2.26-2.31 (m, 2H) 1.84-1.92 (m, 2H). MS (ESI+) m/z 362 (M+H)$^+$.

Example 55. N-ethyl-3-(3-methyl-4-oxo-4,5,6,7-tetrahydro-2H-isoindol-1-yl)-4-phenoxybenzamide Example 54 (36.1 mg, 0.10 mmol), HATU (76 mg, 0.200 mmol), and N,N-diisopropylethylamine (0.035 mL, 0.200 mmol) were combined in tetrahydrofuran (2 mL), stirred at room temperature for 5 minutes, treated with ethanamine (0.1 mL of 2.0 M solution in tetrahydrofuran, 0.20 mmol) and stirred at room temperature for 1 hour. The reaction mixture was partitioned with ethyl acetate and 1M HCl. The organic layer was washed with brine, dried with anhydrous sodium sulfate, filtered and concentrated. The residue was purified by flash chromatography (silica gel, 1-2% methanol in dichloromethane), followed by trituration (methanol) to afford the title compound (19 mg, 49%). $^1$H NMR (300 MHz, DMSO-$d_6$) δ 11.44 (s, 1H) 8.42 (t, J=5.43 Hz, 1H) 7.92 (d, J=2.03 Hz, 1H) 7.75 (dd, J=8.65, 2.20 Hz, 1H) 7.33-7.43 (m, 2H) 7.10-7.18 (m, 1H) 6.98-7.06 (m, 2H) 6.90 (d, J=8.48 Hz, 1H) 3.24-3.32 (m, 2H) 2.60 (t, J=6.10 Hz, 2H) 2.44 (s, 3H) 2.25-2.32 (m, 2H) 1.80-1.92 (m, 2H) 1.12 (t, J=7.12 Hz, 3H). MS (ESI+) m/z 389 (M+H)$^+$.

Example 56. 3-(3-methyl-4-oxo-4,5,6,7-tetrahydro-2H-isoindol-1-yl)-4-phenoxy-N-(tetrahydrofuran-2-ylmethyl)benzamide Example 56 prepared according to the procedure similar to that used for the preparation of Example 55, substituting (tetrahydrofuran-2-yl)methanamine for ethanamine and reaction mixture was stirred for 24 hours instead of 1 hour. Purification by flash chromatography (silica gel, 1-2% methanol in dichloromethane) followed by trituration (50% dichloromethane in hexane) afforded the title compound (29 mg, 65%). $^1$H NMR (300 MHz, DMSO-$d_6$) δ 11.44 (s, 1H) 8.48 (t, J=5.76 Hz, 1H) 7.94 (d, J=2.03 Hz, 1H) 7.76 (dd, J=8.48, 2.37 Hz, 1H) 7.30-7.48 (m, 2H) 7.11-7.20 (m, 1H) 6.99-7.08 (m, 2H) 6.90 (d, J=8.82 Hz, 1H) 3.90-4.04 (m, 1H) 3.72-3.82 (m, 1H) 3.57-3.67 (m, 1H) 3.30-3.36 (m, 2H) 2.60 (t, J=5.93 Hz, 2H) 2.44 (s, 3H) 2.28 (t, J=6.10 Hz, 2H) 1.74-1.97 (m, 5H) 1.53-1.63 (m, 1H). MS (ESI+) m/z 445 (M+H)$^+$.

Example 57. 3-(3-methyl-4-oxo-4,5,6,7-tetrahydro-2H-isoindol-1-yl)-4-phenoxy-N-(1,3-thiazol-2-yl)benzamide Example 57 was prepared according to the procedure similar to that used for the preparation of Example 55, substituting thiazol-2-amine for ethanamine and the reaction mixture was stirred for 24 hours instead of 1 hour, to provide the title compound (11 mg, 25%). $^1$H NMR (300 MHz, DMSO-$d_6$) δ 12.55 (s, 1H) 11.44 (s, 1H) 8.20 (d, J=2.38 Hz, 1H) 8.02 (dd, J=8.53, 2.18 Hz, 1H) 7.56 (d, J=3.57 Hz, 1H) 7.39-7.50 (m, 2H) 7.27 (d, J=3.57 Hz, 1H) 7.16-7.25 (m, 1H) 7.07-7.15 (m, 2H) 6.91 (d, J=8.73 Hz, 1H) 2.66 (t, J=5.95 Hz, 2H) 2.47 (s, 3H) 2.23-2.36 (m, 2H) 1.84-1.94 (m, 2H). MS (ESI+) m/z 444 (M+H)$^+$.

Example 58. 1-(1,3-benzodioxol-5-yl)-3,6,6-trimethyl-2,5,6,7-tetrahydro-4H-isoindol-4-one Example 58a. ethyl 3,6,6-trimethyl-4-oxo-4,5,6,7-tetrahydro-2H-isoindole-1-carboxylate A 25 mL roundbottom flask with stirbar was charged with 2-acetyl-5,5-dimethylcyclohexane-1,3-dione (5 g, 27.4 mmol) and sodium acetate (2.57 g, 31.3 mmol) in acetic acid (30 mL). The well-stirred mixture was placed in a 100° C. oil bath and became homogeneous. A solution of diethyl 2-aminomalonate (4.184 g, 23.88 mmol) in 10 mL acetic acid was added dropwise, and the mixture was stirred at 100° C. After 3 hours an additional portion of sodium acetate (2.75 g, 33.5 mmol) was added. After 20 hours, the mixture was poured over ice, then shaken in a separatory funnel with water and ether (250 mL). The organics were washed twice with aqueous sodium bicarbonate then dried over anhydrous sodium sulfate. Filtration and solvent removal gave a brown solid. The crude material was adsorbed on silica gel and chromatographed on a 220 g silica gel cartridge eluting with 10-100% ethyl acetate/hexanes to provide the title compound.

Example 58b. 3,6,6-trimethyl-4-oxo-4,5,6,7-tetrahydro-2H-isoindole-1-carboxylic Acid A 200 mL recovery flask with stirbar was charged with Example 58a (1.184 g, 4.75 mmol) and lithium hydroxide monohydrate (0.57 g, 13.58 mmol) in tetrahydrofuran (40.0 mL) and water (20 mL). The mixture was stirred in a 60° C. oil bath for 56 hours. The mixture was allowed to cool, then diluted with 80 mL water and extracted twice with ether. The aqueous phase was acidified with conc. HCl and extracted with dichloromethane and ethyl acetate sequentially. These organic extracts were combined and dried over anhydrous sodium sulfate. Filtration and solvent removal provided the title compound.

Example 58c.
3,6,6-trimethyl-6,7-dihydro-2H-isoindol-4(5H)-one

A 250 mL recovery flask with stirbar was charged with Example 58b (0.61 g, 2.76 mmol) in ethanol (25.00 mL)/ water (1 mL). The flask was placed in a 100° C. oil bath and treated with concentrated HCl (2.8 mL, 28.0 mmol). The mixture was heated for 30 minutes, then allowed to cool. The solution was reduced to about ⅓ volume by rotovap then shaken in a separatory funnel with 100 mL each water and dichloromethane. The organics were washed with aqueous sodium bicarbonate and water, and dried over anhydrous sodium sulfate. Filtration and solvent removal provided the title compound.

Example 58d. 1-bromo-3,6,6-trimethyl-6,7-dihydro-2H-isoindol-4(5H)-one

A 50 mL roundbottom flask with stirbar was charged with Example 58c (0.395 g, 2.229 mmol) in tetrahydrofuran (6 mL) and cooled to −78° C. under nitrogen. Recrystallized N-bromo succinimide (0.402 g, 2.259 mmol) was added and the mixture stirred for 30 minutes. The reaction mixture was poured into a separatory funnel containing aqueous sodium sulfite and extracted into 60 mL ether. The organics were washed with aqueous sodium bicarbonate and dried over magnesium sulfate. After filtration and solvent removal, the crude material was adsorbed on silica gel and chromatographed on a 40 g silica cartridge eluting with 10-100% ethyl acetate/hexanes to provide the title compound.

Example 58e. 1-(1,3-benzodioxol-5-yl)-3,6,6-trimethyl-2,5,6,7-tetrahydro-4H-isoindol-4-one A 4 mL vial was charged with a stir bar, a solution of example 58d (14.09 mg, 0.055 mmol) in ethanol (500 µL), a solution of benzo[d][1,3]dioxol-5-ylboronic acid (10.95 mg, 1.2 eq, 0.066 mmol) in ethanol (220.04 µL), an aqueous solution of 1M $Cs_2CO_3$ (110.02 µL, 2.0 equivalents, 0.11 mmol), and SiliaCat DPP-Pd resin (Silicycle, Inc.) (20.37 mg, 0.10 equivalent, 0.27 mmol/g loading), capped and placed in Anton Paar Synthos 3000 parallel microwave optimizer at 120° C. for 30 minutes. Upon completion the crude material was filtered, dried, and the residue was purified by reverse phase HPLC (C18, 0-100% $CH_3CN$/water (0.1% TFA)) to afford the title compound. $^1$H NMR (300 MHz, DMSO-$d_6$) δ 7.01 (d, J=1.5 Hz, 1H), 6.98 (d, J=8.3 Hz, 1H), 6.93 (dd, J=1.5, 8.3 Hz, 1H), 6.02 (s, 2H), 2.62 (s, 2H), 2.46 (s, 3H), 2.21 (s, 2H), 0.98 (s, 6H). MS (ESI+) m/z 298.1 (M+H)$^+$.

Example 59. 3,6,6-trimethyl-1-phenyl-2,5,6,7-tetrahydro-4H-isoindol-4-one

Example 59 was prepared according to the procedure similar to that used for the preparation of Example 58e, substituting phenylboronic acid for benzo[d][1,3]dioxol-5-ylboronic acid, to provide the title compound. $^1$H NMR (300 MHz, DMSO-$d_6$) δ 7.48-7.41 (m, 4H), 7.07 (t, J=7.17 Hz, 1H), 2.69 (s, 2H), 2.48 (s, 3H), 2.23 (s, 2H), 0.99 (s, 6H). MS (ESI+) m/z 254.1 (M+H)$^+$.

Example 60. 1-(2,5-dimethylphenyl)-3,6,6-trimethyl-2,5,6,7-tetrahydro-4H-isoindol-4-one Example 60 was prepared according to the procedure similar to that used for the preparation of Example 58e, substituting 2,5-dimethylphenylboronic acid for benzo[d][1,3]dioxol-5-ylboronic acid, to provide the title compound. $^1$H NMR (300 MHz, DMSO-$d_6$) δ 7.18 (d, J=7.63 Hz, 1H), 7.07 (d, J=7.63 Hz, 1H), 7.01 (s, 1H), 2.44 (s, 3H), 2.31 (s, 2H), 2.28 (s, 3H), 2.20 (s, 2H), 2.17 (s, 3H), 0.95 (s, 6H). MS (ESI+) m/z 282.1 (M+H)$^+$.

Example 61. 3,6,6-trimethyl-1-[2-(morpholin-4-yl)phenyl]-2,5,6,7-tetrahydro-4H-isoindol-4-one Example 61 was prepared according to the procedure similar to that used for the preparation of Example 58e, substituting 2-morpholinophenylboronic acid for benzo[d][1,3]dioxol-5-ylboronic acid, to provide the title compound. $^1$H NMR (300 MHz, DMSO-$d_6$) δ 7.27 (m, 1H), 7.19 (dd, J=1.68, 7.78 Hz, 1H), 7.06 (m, 2H), 3.61 (m, 4H), 2.71 (m, 4H), 2.53 (s, 2H), 2.48 (s, 3H), 2.21 (s, 2H), 0.96 (s, 6H). MS (ESI+) m/z 339.1 (M+H)$^+$.

Example 62. 1-[2-(benzyloxy)phenyl]-3,6,6-trimethyl-2,5,6,7-tetrahydro-4H-isoindol-4-one Example 62 was prepared according to the procedure similar to that used for the preparation of Example 58e, substituting 2-benzyloxyphenylboronic acid for benzo[d][1,3]dioxol-5-ylboronic acid, to provide the title compound. $^1$H NMR (300 MHz, DMSO-$d_6$) δ 7.42 (m, 2H), 7.39-7.27 (m, 5H), 7.17 (d, J=7.7 Hz, 1H), 7.03 (t, J=7.5 Hz, 1H), 5.12 (s, 2H), 2.44 (s, 3H), 2.42 (s, 2H), 2.13 (s, 2H), 0.89 (s, 6H). MS (ESI+) m/z 360.1 (M+H)$^+$.

Example 63. 3,6,6-trimethyl-1-(2-phenoxyphenyl)-2,5,6,7-tetrahydro-4H-isoindol-4-one Example 63 was prepared according to the procedure similar to that used for the preparation of Example 58e, substituting 2-phenoxyphenylboronic acid for benzo[d][1,3]dioxol-5-ylboronic acid, to provide the title compound. $^1$H NMR (300 MHz, DMSO-$d_6$) δ 7.41 (dd, J=1.8, 7.6 Hz, 1H), 7.34-7.24 (m, 4H), 7.01 (m, 2H), 6.85 (d, J=7.9 Hz, 2H), 2.47 (s, 2H), 2.40 (s, 3H), 2.14 (s, 2H), 0.88 (s, 6H). MS (ESI+) m/z 346.1 (M+H)$^+$.

Example 64. N-[3-(3,6,6-trimethyl-4-oxo-4,5,6,7-tetrahydro-2H-isoindol-1-yl)phenyl]methanesulfonamide Example 64 was prepared according to the procedure similar to that used for the preparation of Example 58e, substituting 3-(methylsulfonamido)phenylboronic acid for benzo[d][1,3]dioxol-5-ylboronic acid, to provide the title compound. $^1$H NMR (300 MHz, DMSO-$d_6$) δ 7.38 (t, J=7.78 Hz, 1H), 7.30 (m, 1H), 7.23 (m, 1H), 7.07 (m, 1H), 3.01 (s, 3H), 2.66 (s, 2H), 2.48 (s, 3H), 2.24 (s, 2H), 0.99 (s, 6H). MS (ESI+) m/z 347.1 (M+H)$^+$.

Example 65. 3,6-dimethyl-1-(2-phenoxyphenyl)-2,5,6,7-tetrahydro-4H-isoindol-4-one

Example 65a. ethyl 3,6-dimethyl-4-oxo-4,5,6,7-tetrahydro-2H-isoindole-1-carboxylate A 50 mL round bottom flask with stirbar was charged with 2-acetyl-5-methylcyclohexane-1,3-dione (2.019 g, 12.00 mmol) and sodium acetate (3.87 g, 47.2 mmol) in acetic acid (15 mL). The well-stirred mixture was placed in a 100° C. oil bath and became homogeneous. A solution of diethyl 2-aminomalonate, hydrochloric acid (2.79 g, 13.18 mmol) in acetic acid (10.00 mL) was added dropwise, and the mixture was stirred at 100° C. After 18 hours, the mixture was poured over ice, then shaken in a separatory funnel with water and ether (250 mL). The organics were washed twice with aqueous sodium hydroxide (pH of second wash was basic) then dried over anhydrous sodium sulfate. After filtration and solvent removal, the crude material was adsorbed on silica gel and chromatographed on a 150 g silica gel cartridge eluting with 10-100% ethyl acetate/hexanes to provide the title compound.

Example 65b. 3,6-dimethyl-4-oxo-4,5,6,7-tetrahydro-2H-isoindole-1-carboxylic Acid A 100 mL recovery flask with stirbar was charged with Example 65a (0.879 g, 3.74 mmol) and lithium hydroxide monohydrate (0.345 g, 8.22 mmol) in tetrahydrofuran (30.0 mL) and water (15 mL). The mixture was stirred in a 60° C. oil bath over three days. LCMS trace shows clean conversion to a peak with the expected mass. The mixture was diluted with 40 mL water, acidified with concentrated HCl, and allowed to cool with vigorous stirring. After chilling in an ice bath, the suspension was filtered. The precipitate was vacuum dried to provide the title compound.

Example 65c. 3,6-dimethyl-4-oxo-4,5,6,7-tetrahydro-2H-isoindole-1-carboxylic Acid A 100 mL round-bottom flask with stirbar and reflux condenser was charged with Example 65b (0.648 g, 3.13 mmol) in ethanol (30.0 mL)/water (1.2 mL). The flask was placed in a 100° C. oil bath and treated with concentrated HCl (2.5 mL, 30.4 mmol). The mixture was heated for 30 minutes, then allowed to cool. The solution was shaken in a separatory funnel with 100 mL each of brine and dichloromethane. The organics were washed with aqueous sodium bicarbonate, and dried over anhydrous sodium sulfate. Filtration and solvent removal gave the title compound.

Example 65d. 1-bromo-3,6-dimethyl-6,7-dihydro-2H-isoindol-4(5H)-one

A 50 mL round bottom flask with stirbar was charged with Example 65c (0.434 g, 2.66 mmol) in tetrahydrofuran (10 mL) and cooled to −78° C. under nitrogen. Recrystallized N-bromo succinimide (0.529 g, 2.97 mmol) was added and the mixture stirred for 30 minutes. The reaction mixture was poured into a separatory funnel containing aqueous sodium sulfite and extracted into 75 mL ether. The organics were washed with aqueous sodium bicarbonate and dried over magnesium sulfate. Filtration and solvent removal provided 0.632 g lavender solid which was chromatographed on a 40 g silica cartridge eluting with 10-100% ethyl acetate/hexanes to provide the title compound.

Example 65e. 3,6-dimethyl-1-(2-phenoxyphenyl)-2,5,6,7-tetrahydro-4H-isoindol-4-one A 5 mL microwave reaction vessel equipped with stirbar was charged with Example 65d (0.078 g, 0.322 mmol), 2-phenoxyphenylboronic acid (0.106 g, 0.495 mmol), 2 M aqueous sodium carbonate (1.6 mL, 3.20 mmol) and bis (triphenylphosphine)palladium(II) dichloride (0.015 g, 0.021 mmol) in ethanol (1.4 mL)/DME (1.4 mL) and sealed. The mixture was heated at 120° C. for 30 minutes in a Biotage Initiator 2 monomode microwave reactor, then cooled to ambient temperature. The mixture was shaken in a separatory funnel with 50 mL ethyl acetate and 50 mL brine. The organics were dried over anhydrous sodium sulfate. After filtration and solvent removal the residue was purified by reverse phase HPLC (C18, 0-100% $CH_3CN$/water (0.1% TFA)) to afford the title compound. $^1$H NMR (300 MHz, $CDCl_3$) δ 9.15 (bs, 1H), 7.51 (m, 1H), 7.35 (m, 2H), 7.19 (m, 3H), 7.01 (d, J=2.7 Hz, 2H), 6.93 (m, 1H), 2.98 (m, 1H), 2.54 (s, 3H), 2.53 (m, 2H), 2.26 (m, 2H), 1.13 (d, J=3.2 Hz, 3H). MS (ESI+) m/z 332.2 (M+H)$^+$.

Example 66. 1-(5-amino-2-phenoxyphenyl)-3,6-dimethyl-2,5,6,7-tetrahydro-4H-isoindol-4-one Example 66 was prepared according to the procedure similar to that used for the preparation of Example 65e, substituting 4-phenoxy-3-(4,4,5,5-tetramethyl-1,3,2-dioxaborolan-2-yl)aniline for 2-phenoxyphenylboronic acid, to provide the title compound. $^1$H NMR (300 MHz, $CDCl_3$) δ 9.07 (bs, 1H), 7.32 (m, 2H), 7.04 (t, J=7.6 Hz, 1H), 6.92-6.83 (m, 3H), 6.59 (dd, J=3.1, 9.2 Hz, 1H), 2.96 (m, 1H), 2.49 (s, 3H), 2.48 (m, 2H), 2.24 (m, 2H), 1.11 (d, J=6.1 Hz, 3H). MS (ESI+) m/z 347.2 (M+H)$^+$.

Example 67. N-[3-(3,6-dimethyl-4-oxo-4,5,6,7-tetrahydro-2H-isoindol-1-yl)-4-phenoxyphenyl]methanesulfonamide Example 66 (0.074 g, 0.213 mmol) in tetrahydrofuran (4 mL) was treated sequentially with methanesulfonyl chloride (0.041 mL, 0.533 mmol) and triethylamine (0.089 mL, 0.639 mmol) and stirred at ambient temperature. After 90 minutes of stirring, aqueous sodium hydroxide (1M) (2 mL, 2.000 mmol) was added and the mixture was heated at 45° C. for 1 hour. The reaction mixture was acidified with 1 N HCl solution (2.5 mL), diluted with ethyl acetate, washed with brine, dried over anhydrous magnesium sulfate, filtered and concentrated. The residue was purified by reverse phase HPLC (C18, 0-100% $CH_3CN$/water (0.1% TFA)) to afford the title compound. $^1$H NMR (300 MHz, $CDCl_3$) δ 9.16 (bs, 1H), 7.42 (d, J=2.6 Hz, 1H), 7.37 (m, 2H), 7.16 (m, 1H), 7.01 (m, 2H), 6.98 (d, J=2.7 Hz, 1H), 6.88 (d, J=8.5 Hz, 1H), 6.34 (s, 1H), 3.05 (s, 3H), 2.97 (m, 1H), 2.54 (s, 3H), 2.50 (m, 2H), 2.26 (m, 2H), 1.14 (d, J=6.1 Hz, 3H). MS (ESI+) m/z 425.1 (M+H)$^+$.

Example 68. 3-methyl-6-(2-methylpropyl)-1-(2-phenoxyphenyl)-2,5,6,7-tetrahydro-4H-isoindol-4-one Example 68 was prepared according to the procedure similar to that used for the preparation of Example 65, substituting 2-acetyl-5-(2-methylpropyl)cyclohexane-1,3-dione for 2-acetyl-5-methylcyclohexane-1,3-dione, to provide the title compound. $^1$H NMR (300 MHz, $CDCl_3$) δ 9.08 (bs, 1H), 7.52 (m, 1H), 7.34 (t, J=7.4 Hz, 2H), 7.19-7.10 (m, 3H), 7.01 (d, J=7.2 Hz, 2H), 6.92 (m, 1H), 2.98 (m, 1H), 2.54 (s, 3H), 2.51 (m, 2H), 2.21 (m, 2H), 1.72 (m, 1H), 1.31 (t, J=6.8 Hz, 2H), 0.88 (d, J=6.4 Hz, 6H). MS (ESI+) m/z 467.2 (M+H)$^+$.

Example 69. N-{3-[3-methyl-6-(2-methylpropyl)-4-oxo-4,5,6,7-tetrahydro-2H-isoindol-1-yl]-4-phenoxyphenyl}methanesulfonamide

Example 69a. 1-bromo-6-isobutyl-3-methyl-6,7-dihydro-2H-isoindol-4(5H)-one

Example 69a was prepared according to the procedure similar to that used for the preparation of Example 65d, substituting 2-acetyl-5-(2-methylpropyl)cyclohexane-1,3-dione for 2-acetyl-5-methylcyclohexane-1,3-dione, to provide the title compound.

Example 69b. 1-(5-amino-2-phenoxyphenyl)-6-isobutyl-3-methyl-6,7-dihydro-2H-isoindol-4(5H)-one Example 69b was prepared according to the procedure similar to that used for the preparation of Example 65e, substituting Example 69a for Example 65d, and substituting 4-phenoxy-3-(4,4,5,5-tetramethyl-1,3,2-dioxaborolan-2-yl)aniline for 2-phenoxyphenylboronic acid, to provide the title compound.

Example 69c. N-{3-[3-methyl-6-(2-methylpropyl)-4-oxo-4,5,6,7-tetrahydro-2H-isoindol-1-yl]-4-phenoxyphenyl}methanesulfonamide Example 69c was prepared according to the procedure similar to that used for the preparation of Example 67, substituting Example 69b for Example 66, to provide the title compound. $^1$H NMR (300 MHz, CDCl$_3$) δ 9.16 (bs, 1H), 7.43 (d, J=2.3 Hz, 1H), 7.37 (m, 2H), 7.16 (m, 1H), 7.02 (m, 2H), 6.97 (d, J=2.7 Hz, 1H), 6.89 (d, J=8.8 Hz, 1H), 6.31 (s, 1H), 3.05 (s, 3H), 2.98 (m, 1H), 2.54 (s, 3H), 2.51 (m, 2H), 2.22 (m, 2H), 1.74 (m, 1H), 1.32 (t, J=7.1 Hz, 2H), 0.89 (d, J=6.5 Hz, 6H). MS (ESI+) m/z 467.2 (M+H)$^+$.

Example 70. 3-methyl-1-(2-phenoxyphenyl)-6-(propan-2-yl)-2,5,6,7-tetrahydro-4H-isoindol-4-one Example 70 was prepared according to the procedure similar to that used for the preparation of Example 65, substituting 2-acetyl-5-(2-methylethyl)cyclohexane-1,3-dione for 2-acetyl-5-methylcyclohexane-1,3-dione, to provide the title compound. $^1$H NMR (300 MHz, CDCl$_3$) δ 9.07 (bs, 1H), 7.52 (m, 1H), 7.34 (m, 2H), 7.21-7.17 (m, 2H), 7.12 (m, 1H), 7.01 (m, 2H), 9.92 (m, 1H), 2.93 (m, 1H), 2.58 (dd, J=11.2, 16.2 Hz, 1H), 2.54 (s, 3H), 2.48 (m, 1H), 2.29 (dd, J=11.2, 16.2 Hz, 1H), 1.93 (m, 1H), 1.67 (m, 1H), 0.97 (d, J=6.8 Hz, 6H). MS (ESI+) m/z 360.2 (M+H)$^+$.

Example 71. N-{3-[3-methyl-4-oxo-6-(propan-2-yl)-4,5,6,7-tetrahydro-2H-isoindol-1-yl]-4-phenoxyphenyl}methanesulfonamide

Example 71a. 1-bromo-6-isopropyl-3-methyl-6,7-dihydro-2H-isoindol-4(5H)-one

Example 71a was prepared according to the procedure similar to that used for the preparation of Example 65d, substituting 2-acetyl-5-(2-methylethyl)cyclohexane-1,3-dione for 2-acetyl-5-methylcyclohexane-1,3-dione, to provide the title compound.

Example 71b. 1-(5-amino-2-phenoxyphenyl)-6-isopropyl-3-methyl-6,7-dihydro-2H-isoindol-4(5H)-one Example 71b was prepared according to the procedure similar to that used for the preparation of Example 65e, substituting Example 71a for Example 65d, and substituting 4-phenoxy-3-(4,4,5,5-tetramethyl-1,3,2-dioxaborolan-2-yl)aniline for 2-phenoxyphenylboronic acid, to provide the title compound.

Example 71c. N-{3-[3-methyl-4-oxo-6-(propan-2-yl)-4,5,6,7-tetrahydro-2H-isoindol-1-yl]-4-phenoxyphenyl}methanesulfonamide Example 71c was prepared according to the procedure similar to that used for the preparation of Example 67, substituting Example 71b for Example 66, to provide the title compound. $^1$H NMR (300 MHz, CDCl$_3$) δ 9.18 (bs, 1H), 7.49 (d, J=2.7 Hz, 1H), 7.37 (t, J=8.0 Hz, 2H), 7.27-7.21 (m, 2H), 7.16 (m, 1H), 7.05-6.92 (m, 1H), 6.86 (m, 1H), 3.05 (s, 3H), 3.02 (m, 1H), 2.59 (m, 1H), 2.54 (s, 3H), 2.51 (m, 1H), 2.29 (dd, J=11.2, 16.2 Hz, 1H), 1.92 (m, 1H), 1.68 (m, 1H), 0.96 (d, J=4.8 Hz, 6H). MS (ESI+) m/z 453.2 (M+H)$^+$.

Example 72. N-[3-(3-methyl-4-oxo-6-phenyl-4,5,6,7-tetrahydro-2H-isoindol-1-yl)-4-phenoxyphenyl]methanesulfonamide

Example 72a. 1-bromo-6-phenyl-3-methyl-6,7-dihydro-2H-isoindol-4(5H)-one

Example 72a was prepared according to the procedure similar to that used for the preparation of Example 65d, substituting 2-acetyl-5-phenylcyclohexane-1,3-dione for 2-acetyl-5-methylcyclohexane-1,3-dione, to provide the title compound.

Example 72b. 1-(5-amino-2-phenoxyphenyl)-6-phenyl-3-methyl-6,7-dihydro-2H-isoindol-4(5H)-one Example 72b was prepared according to the procedure similar to that used for the preparation of Example 65e, substituting Example 72a for Example 65d, and substituting 4-phenoxy-3-(4,4,5,5-tetramethyl-1,3,2-dioxaborolan-2-yl)aniline for 2-phenoxyphenylboronic acid, to provide the title compound.

Example 72c. N-[3-(3-methyl-4-oxo-6-phenyl-4,5,6,7-tetrahydro-2H-isoindol-1-yl)-4-phenoxyphenyl]methanesulfonamide Example 72c was prepared according to the procedure similar to that used for the preparation of Example 67, substituting Example 72b for Example 66, to provide the title compound. $^1$H NMR (300 MHz, CDCl$_3$) δ 9.12 (bs, 1H), 7.48 (dd, J=7.4, 2.3 Hz, 1H), 7.38-7.31 (m, 5H), 7.29-7.23 (m, 1H), 7.20-7.08 (m, 3H), 7.03-7.00 (m, 2H), 6.91 (m, 1H), 3.37 (m, 1H), 3.18 (m, 1H), 3.07 (s, 3H), 3.00 (m, 1H), 2.82-2.67 (m, 2H), 2.58 (s, 3H). MS (ESI+) m/z 487.1 (M+H)$^+$.

Example 73. 1-[2-(cyclopropylmethoxy)-5-(methylsulfonyl)phenyl]-3-methyl-2,5,6,7-tetrahydro-4H-isoindol-4-one

Example 73a. 1-(2-fluoro-5-(methylsulfonyl)phenyl)-3-methyl-6,7-dihydro-2H-isoindol-4(5H)-one A 5 mL microwave tube equipped with a stir bar was charged with 3-methyl-6,7-dihydro-2H-isoindol-4(5H)-one (0.217 g, 1.455 mmol), 2-bromo-1-fluoro-4-(methylsulfonyl)benzene (0.253 g, 1.000 mmol), allylpalladium(II) chloride (0.0176 g, 0.048 mmol) and potassium acetate (0.329 g, 3.35 mmol), sealed, and purged with nitrogen. Degassed N,N-dimethylacetamide (5 ml) was introduced, and the vessel was placed in an oil bath and stirred for 18 hours at 130° C. The reaction mixture was cooled and shaken in a separatory funnel with 60 mL each of EtOAc and brine. The organics were washed twice with brine and dried over sodium sulfate. After filtration the mixture was concentrated and chromatographed on a 40 g silica cartridge eluting with 0-100% EtOAc/heptane to provide the title compound.

Example 73b. 1-[2-(cyclopropylmethoxy)-5-(methylsulfonyl)phenyl]-3-methyl-2,5,6,7-tetrahydro-4H-isoindol-4-one A 5 mL microwave reaction vessel equipped with a stir bar was charged with sodium hydride (dry, 95% 16.8 mg, 0.665 mmol) suspended in THF (0.5 mL), then cyclopropylmethanol (35 μL, 0.432 mmol) and sealed. After stirring for 10 minutes, Example 73a (70 mg, 0.218 mmol) in THF (2.0 mL) was added. The mixture was heated at 60° C. in an oil bath for 20 hours. The mixture was cooled and partitioned between 60 mL each of EtOAc and brine. The organics were dried over magnesium sulfate. After filtration and solvent removal the residue was purified by reverse phase HPLC (C18, 0-100% CH$_3$CN/water (0.1% TFA)) to afford the title compound. $^1$H NMR (300 MHz, DMSO-d$_6$) δ ppm 11.34 (bds, 1H), 7.80-7.71 (m, 2H), 7.26 (d, J=8.8 Hz, 1H), 3.98 (d, J=7.1 Hz, 2H), 3.18 (s, 3H), 2.64 (t, J=5.9 Hz, 2H), 2.28 (s, 3H), 2.33 (m, 2H), 1.91 (m, 2H), 1.25 (m, 1H), 0.57 (m, 2H), 0.36 (m, 2H). MS (ESI+) m/z 374.1 (M+H)$^+$.

BIOLOGICAL EXAMPLES

Bromodomain Domain Binding Assay

A time-resolved fluorescence resonance energy transfer (TR-FRET) assay was used to determine the affinities of compounds of the Examples listed in Table 1 for each bromodomain of BRD4. His-tagged first (BD1: amino acids K57-E168) and second (BD2: amino acids E352-E168) bromodomains of BRD4 were expressed and purified. An Alexa647-labeled BET-inhibitor was used as the fluorescent probe in the assay.

Synthesis of Alexa647-Labeled Bromodomain Inhibitor Compound 2-((6S,Z)-4-(4-chlorophenyl)-2,3,9-trimethyl-6H-thieno[3,2-f][1,2,4]triazolo[4,3-a][1,4]diazepin-6-yl)acetic Acid Methyl 2-((6S,Z)-4-(4-chlorophenyl)-2,3,9-trimethyl-6H-thieno[3,2-f][1,2,4]triazolo[4,3-a][1,4]diazepin-6-yl)acetate (see e.g., WO 2006129623)(100.95 mg, 0.243 mmol was suspended in 1 mL methanol to which was added a freshly prepared solution of lithium hydroxide monohydrate (0.973 mL, 0.5 M, 0.487 mmol) and shaken at ambient temperature for 3 hours. The methanol was evaporated and the pH adjusted with aqueous hydrochloric acid (1 M, 0.5 mL, 0.5 mmol) and extracted four times with ethyl acetate. The combined ethyl acetate layers were dried over magnesium sulfate and evaporated to afford 2-((6S,Z)-4-(4-chlorophenyl)-2,3,9-trimethyl-6H-thieno[3,2-f][1,2,4]triazolo[4,3-a][1,4]diazepin-6-yl)acetic acid (85.3 mg, 87.0%); ESI-MS m/z=401.1 [(M+H)$^+$] which was used directly in the next reaction.

N-(2-(2-(2-aminoethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide bis(2,2,2-trifluoroacetate)

2-((6S,Z)-4-(4-chlorophenyl)-2,3,9-trimethyl-6H-thieno[3,2-f][1,2,4]triazolo[4,3-a][1,4]diazepin-6-yl)acetic acid) (85.3 mg, 0.213 mmol) was combined with 2,2'-(ethane-1,2-diylbis(oxy))diethanamine (Sigma-Aldrich, 0.315 mg, 2.13 mmol) were combined in 5 mL anhydrous dimethylformamide. (1H-benzo[d][1,2,3]triazol-1-yloxy)tripyrrolidin-1-ylphosphonium hexafluorophosphate(V) (PyBOB, CSBio, Menlo Park Calif.; 332 mg, 0.638 mmol) was added and the reaction shaken at ambient temperature for 16 hours. The reaction was diluted to 6 mL with dimethylsulfoxide:water (9:1, v:v) and purified in two injections with time collection Waters Deltapak C18 200×25 mm column eluted with a gradient of 0.1% trifluoroacetic acid (v/v) in water and acetonitrile. The fractions containing the two purified products were lyophilized to afford N-(2-(2-(2-aminoethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide bis(2,2,2-trifluoroacetate) (134.4 mg, 82.3%); ESI-MS m/z=531.1 [(M+H)$^+$]; 529.1 [(M−H)$^-$] and (S,Z)—N,N'-(2,2'-(ethane-1,2-diylbis(oxy))bis(ethane-2,1-diyl))bis (2-((6S,Z)-4-(4-chlorophenyl)-2,3,9-trimethyl-6H-thieno[3,2-f][1,2,4]triazolo[4,3-a][1,4]diazepin-6-yl)acetamide) bis (2,2,2-trifluoroacetate) (3.0 mg, 1.5%); ESI-MS m/z=913.2 [(M+H)$^+$]; 911.0 [(M−H)$^-$].

N-(2-(2-(2-amido-(Alexa647)-ethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl) acetamide(2,2,2-trifluoroacetate)

N-(2-(2-(2-aminoethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide bis(2,2,2-trifluoroacetate) (5.4 mg, 0.0071 mmol) was combined with Alexa Fluor® 647 carboxylic Acid, succinimidyl ester (Life Technologies, Grand Island, N.Y.; 3 mg, 0.0024 mmol) were combined in 1 mL anhydrous dimethylsulfoxide containing diisopropylethylamine (1% v/v) and shaken at ambient temperature for 16 hours. The reaction was diluted to 3 mL with dimethylsulfoxide:water (9:1, v:v) and purified in one injection with time collection Waters Deltapak C18 200×25 mm column eluted with a gradient of 0.1% trifluoroacetic acid (v/v) in water and acetonitrile. The fractions containing the purified product were lyophilized to afford N-(2-(2-(2-amido-(Alexa647)-ethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide(2,2,2-trifluoroacetate) (1.8 mg); MALDI-MS m/z=1371.1, 1373.1 [(M+H)$^+$] as a dark blue powder.

Assay

Compound dilution series were prepared in DMSO via a 3-fold serial dilution from 2.5 mM to 42 nM. Compounds were then diluted 6:100 in assay buffer (20 mM Sodium Phosphate, pH 6.0, 50 mM NaCl, 1 mM EDTA, 0.01% Triton X-100, 1 mM DTT) to yield 3× working solutions. Six microliters (μL) of the working solution was then transferred to white, low-volume assay plates (Costar #3673). A 1.5× assay mixture containing His-tagged bromodomain, Europium-conjugated anti-His antibody (Invitrogen PV5596) and the Alexa-647-conjugated probe molecule was also prepared. Twelve μL of this solution were added to the assay plate to reach a final volume of 18 μL. The final concentration of 1× assay buffer contains 2% DMSO, 50 μM–0.85 nM compound, 8 nM bromodomain, 1 nM antibody and 100 or 30 nM probe (for BDI or BDII, respectively). After a one-hour incubation at room temperature, TR-FRET ratios were determined using an Envision multilabel plate reader (Ex 340, Em 495/520).

TR-FRET data were normalized to the means of 24 no-compound controls ("high") and 8 controls containing 1 µM un-labeled probe ("low"). Percent inhibition was plotted as a function of compound concentration and the data were fit with the 4 parameter logistic equation to obtain $IC_{50}$s. Inhibition constants ($K_i$) were calculated from the $IC_{50}$s, probe $K_d$ and probe concentration. Typical Z' values were between 0.65 and 0.75. The minimum significant ratio was determined to evaluate assay reproducibility (Eastwood et al., (2006) J Biomol Screen, 11: 253-261). The MSR was determined to be 2.03 for BDI and 1.93 for BDII, and a moving MSR (last six run MSR overtime) for both BDI and BDII was typically <3. The $K_i$ values are reported in Table 1.

MX-1 Cell Line Proliferation Assay

The impact of compounds of the Examples on cancer cell proliferation was determined using the breast cancer cell line MX-1 (ATCC) in a 3-day proliferation assay. MX-1 cells were maintained in RPMI supplemented with 10% FBS at 37 C.° and an atmosphere of 5% $CO_2$. For compound testing, MX-1 cells were plated in 96-well black bottom plates at a density of 5000 cells/well in 90 µl of culture media and incubated at 37° overnight to allow cell adhesion and spreading. Compound dilution series were prepared in DMSO via a 3-fold serial dilution from 3 mM to 0.1 µM. The DMSO dilution series were then diluted 1:100 in phosphate buffered saline, and 10 µL of the resulted solution were added to the appropriate wells of the MX-1 cell plate. The final compound concentrations in the wells were 3, 1, 0.3, 0.1, 0.03, 0.01, 0.003, 0.001, 0.0003 and 0.0001 µM. After the addition of compounds, the cells were incubated for 72 more hours and the amounts of viable cells were determined using the Cell Titer Glo assay kit (Promega) according to manufacturer suggested protocol.

Luminescence readings from the Cell Titer Glo assay were normalized to the DMSO treated cells and analyzed using the GraphPad Prism software with sigmoidal curve fitting to obtain $EC_{50}$s. The minimum significant ratio (MSR) was determined to evaluate assay reproducibility (Eastwood et al., (2006) J Biomol Screen, 11: 253-261). The overall MSR was determined to be 2.1 and a moving MSR (last six run MSR overtime) has been <2. The $EC_{50}$ values are reported in Table 1.

TABLE 1

| Example # | TR-FRET Binding Ki: BRD4 (BDI_K57-E168) (µM) | TR-FRET Binding Ki: BRD4 (BDII_E352-M457) (µM) | Cellular proliferation: $EC_{50}$ (µM) |
| --- | --- | --- | --- |
| 1 | 3.68 | 3.07 | 3.4 |
| 2 | 0.255 | 0.504 | 1.43 |
| 3 | 3.73 | 15.0 | N/A |
| 4 | 2.49 | 15.9 | N/A |
| 5 | 1.4 | 2.03 | 3.7 |
| 6 | 2.7 | 9.97 | N/A |
| 7 | 0.261 | 0.805 | 0.676 |
| 8 | 1.43 | 3.82 | 2.5 |
| 9 | 0.961 | 3.1 | 2.75 |
| 10 | 1.79 | 4.06 | 1.23 |
| 11 | 1.88 | 5.46 | N/A |
| 12 | 2.86 | 10.4 | N/A |
| 13 | 7.29 | 22.2 | N/A |
| 14 | 9.06 | 22.2 | N/A |
| 15 | 1.14 | 22.2 | N/A |
| 16 | 3.77 | 8.42 | N/A |
| 17 | 5.51 | 17.5 | N/A |
| 18 | 0.943 | 2.03 | 1.23 |
| 19 | 0.943 | 19.7 | 3.18 |
| 20 | 1.77 | 4.49 | N/A |
| 21 | 1.86 | 5.92 | N/A |
| 22 | 2.47 | 8.21 | N/A |
| 23 | 9.09 | 8.92 | N/A |
| 24 | 1.2 | 2.3 | N/A |
| 25 | 4.24 | 15.1 | N/A |
| 26 | 6.22 | 10.4 | N/A |
| 27 | 2.76 | 6.58 | N/A |
| 28 | 5.31 | 15.05 | N/A |
| 29 | 0.315 | 2.92 | >3.0 |
| 30 | 1.25 | 4.78 | N/A |
| 31 | 0.765 | 4.68 | >3.0 |
| 32 | 0.202 | 1.94 | 1.88 |
| 33 | 1.04 | 8.16 | >3.0 |
| 34 | 1.35 | 2.62 | >3.0 |
| 35 | 9.14 | 11.0 | N/A |
| 36 | 8.83 | 9.73 | N/A |
| 37 | 0.526 | 4.14 | >3.0 |
| 38 | 4.88 | 4.86 | N/A |
| 39 | 0.148 | 0.365 | 0.232 |
| 40 | 0.015 | 0.043 | 0.16 |
| 41 | 0.161 | 0.216 | 0.37 |
| 42 | 0.569 | 1.09 | >3.0 |
| 43 | 1.82 | 0.568 | >3.0 |
| 44 | 0.067 | 0.037 | 0.645 |
| 45 | 0.04 | 0.198 | 0.329 |
| 46 | 0.014 | 0.052 | 0.238 |
| 47 | 0.011 | 0.019 | 0.193 |
| 48 | 0.068 | 0.043 | 0.564 |
| 49 | 0.043 | 0.192 | 0.364 |
| 50 | 0.071 | 0.551 | 0.609 |
| 51 | 0.164 | 0.943 | N/A |
| 52 | 0.009 | 0.088 | 0.184 |
| 53 | 0.927 | 3.67 | N/A |
| 54 | 0.045 | 0.289 | N/A |
| 55 | 0.077 | 0.511 | 1.39 |
| 56 | 0.068 | 0.653 | 0.734 |
| 57 | 1.07 | 22.2 | N/A |
| 58 | 0.932 | 0.513 | N/A |
| 59 | 3.23 | 2.52 | N/A |
| 60 | 3.37 | 2.7 | N/A |
| 61 | 2.2 | 1.68 | N/A |
| 62 | 1.5 | 1.75 | N/A |
| 63 | 0.786 | 1.03 | N/A |
| 64 | 0.576 | 0.409 | >3.0 |
| 65 | 0.184 | 0.382 | 1.78 |
| 66 | 0.058 | 0.069 | N/A |
| 67 | 0.012 | 0.068 | 0.11 |
| 68 | 3.62 | 22.2 | N/A |
| 69 | 0.151 | 2.07 | 0.60 |
| 70 | 1.2 | 2.22 | N/A |
| 71 | 0.375 | 0.926 | 0.95 |
| 72 | 7.28 | 22.2 | N/A |
| 73 | 0.034 | 0.461 | N/A |

Proliferation Panel Assay.

The compound of Example 40 was tested for its impact on proliferation of a panel of cancer cell line types (with specific cell lines tested) as set out in (Table 2). Cells were plated in 96-well plates at 1500 cells/well in the appropriate culture media. Series dilutions of compound were prepared and added to the wells as in the MX-1 proliferation assay. After the addition of the compound, cells were incubated for another 5 days and the amounts of viable cells were determined using the Cell Titer Glo assay kit (Promega) according to manufacturer suggested protocol. Cell proliferation data were analyzed as described above in the MX-1 proliferation assay to obtain the $EC_{50}$ for the compounds reported in Table 2.

TABLE 2

| Cell line Type | Cell Line | Compound of Example 40 Cellular Proliferation EC$_{50}$ (µM) |
|---|---|---|
| AML | Raji | 0.036 |
| AML | SKM1 | 0.039 |
| Bladder | EJ-1 | 0.594 |
| Breast | MDAMB231 | 0.31 |
| Breast | MDAMB453 | 0.22 |
| Colon | DLD-1 | 0.45 |
| Colon | GEO | 0.38 |
| Glioblastoma | D54MG | 0.210 |
| Head & Neck | FaDu | 0.18 |
| Hepatocellular | HepG2 | 0.32 |
| Melanoma | A-375 | 0.168 |
| Multiple Myeloma | NCI-H929 | 0.041 |
| Multiple Myeloma | OPM2 | 0.018 |
| Multiple Myeloma | RPMI-8226 | 0.094 |
| NHL | Ly18 | 0.37 |
| NHL | Ramos | 0.34 |
| NSCLC | H1299 | 0.36 |
| NSCLC | H1975 | 0.18 |
| NSCLC | H460 | >10 |
| Pancreas | BxPC3FP5 | 0.07 |
| Pancreas | HPAC | 0.29 |
| Prostate | PC3M | 0.41 |
| RCC | 786-0 | 0.139 |
| Sarcoma | SK-LMS-1 | 0.176 |

Xenograft Tumor Growth Inhibition Assay

The effect of the compound of Example 40 to inhibit the growth of Ramos, OPM-2, MX-1, MV4-11, and HT1080 xenograft tumors was evaluated. Briefly, 0.5×10$^6$ human cancer cells (HT1080), 1×10$^6$ human cancer cells (Ramos), 5×10$^6$ human cancer cells (OPM-2, MV4-11) or 1:10 tumor brie (MX-1) (in S-MEM (MEM, Suspension, no Calcium, no Glutamine)) (Life Technologies Corporation) were inoculated subcutaneously into the right hind flank of female SCID or SCID-beige (MV4-11, HT1080) mice (Charles Rivers Labs) on study day 0. Compound was formulated in 2% EtOH, 5% Tween-80, 20% PEG-400, 73% HPMC (Ramos, OPM-2 and MX-1) or 5% DMSO, 5% EtOH, 30% PEG400, 60% Phosal 53 (MV4-11, HT1080). Administration of compound was initiated at the time of size match on day 8 (HT1080), day 17 (MX-1), or day 18 (Ramos, MV4-11, OPM-2). The tumors were measured by a pair of calipers twice a week starting at the time of size match and tumor volumes were calculated according to the formula V=L×W$^2$/2 (V: volume, mm$^3$; L: length, mm. W: width, m) Tumor volume was measured for the duration of the experiment until the mean tumor volume in each group reached an endpoint of >1000 mm$^3$. Results are shown in Tables 3-7.

TABLE 3

Ramos human B cell lymphoma cancer xenograft model

| Group | Treatment | Dose route, regimen | % TGI[a] | % TGD[b] |
|---|---|---|---|---|
| 1 | Vehicle | 0 mg/kg/day PO, QDx14 | — | — |
| 2 | Compound of Example 40 | 100 mg/kg/day PO, QDx14 | 30* | 40* |
| 3 | Compound of Example 40 | 100 mg/kg/day PO, BID (5on 3off) x 2 | 35*** | 40** |

[a]Tumor growth inhibition, % TGI = 100 − mean tumor volume of treatment group/mean tumor volume of control group x 100. The p values (as indicated by asterisks) are derived from Student's T test comparison of treatment group vs. control group. Based on day 31. *p < 0.05, p < 0.01, *p < 0.001.
[b]Tumor growth delay, % TGD = (T − C)/C x 100, where T = median time to endpoint of treatment group and C = median time to endpoint of control group. The p values (as indicated by asterisks) derived from Kaplan Meier log-rank comparison of treatment group vs. treatment control group. Based on an endpoint of 1000 mm$^3$. * p < 0.05, p < 0.01, *p < 0.001.

TABLE 4

OPM-2 human multiple myeloma cancer xenograft model

| Group | Treatment | Dose route, regimen | % TGI[a] | % TGD[b] |
|---|---|---|---|---|
| 1 | Vehicle | 0 mg/kg/day PO, QDx14 | — | — |
| 2 | Compound of Example 40 | 100 mg/kg/day PO, QDx14 | 41** | 88*** |
| 3 | Compound of Example 40 | 30 mg/kg/day PO, QDx14 | 27* | 63 |
| 4 | Compound of Example 40 | 10 mg/kg/day PO, QDx14 | 16 | 25 |
| 5 | Compound of Example 40 | 100 mg/kg/day PO, BIDx14 | 43** | 175*** |
| 6 | Compound of Example 40 | 30 mg/kg/day PO, BIDx14 | 31* | 88* |
| 7 | Compound of Example 40 | 10 mg/kg/day PO, BIDx14 | 11 | 25 |

[a]Tumor growth inhibition, % TGI = 100 − mean tumor volume of treatment group/mean tumor volume of control group x 100. The p values (as indicated by asterisks) are derived from Student's T test comparison of treatment group vs. control group. Based on day 31. *p < 0.05, p < 0.01, *p < 0.001.
[b]Tumor growth delay, % TGD = (T − C)/C x 100, where T = median time to endpoint of treatment group and C = median time to endpoint of control group. The p values (as indicated by asterisks) derived from Kaplan Meier log-rank comparison of treatment group vs. treatment control group. Based on an endpoint of 1000 mm$^3$. *p < 0.05, p < 0.01, *p < 0.001.

TABLE 5

Efficacy of BET inhibitor in the MX-1 human breast cancer xenograft model

| Group | Treatment | Dose route, regimen | % TGI[a] | % TGD[b] |
|---|---|---|---|---|
| 1 | Vehicle | 0 mg/kg/day PO, QDx14 | — | — |
| 2 | Compound of Example 40 | 100 mg/kg/day PO, QDx14 | 78*** | 29*** |
| 3 | Compound of Example 40 | 30 mg/kg/day PO, QDx14 | 48*** | 22*** |
| 4 | Compound of Example 40 | 10 mg/kg/day PO, QDx14 | 18 | 17 |
| 5 | Compound of Example 40 | 100 mg/kg/day PO, QDx14 | 80*** | 28*** |
| 6 | Compound of Example 40 | 20 mg/kg/day PO, QDx14 | 30* | 19* |

[a]Tumor growth inhibition, % TGI = 100 − mean tumor volume of treatment group/mean tumor volume of control group x 100. The p values (as indicated by asterisks) are derived from Student's T test comparison of treatment group vs. control group. Based on day 38. *p < 0.05, p < 0.01, *p < 0.001.
[b]Tumor growth delay, % TGD = (T − C)/C x 100, where T = median time to endpoint of treatment group and C = median time to endpoint of control group. The p values (as indicated by asterisks) derived from Kaplan Meier log-rank comparison of treatment group vs. treatment control group. Based on an endpoint of 1000 mm$^3$. *p < 0.05, p < 0.01, *p < 0.001.

TABLE 6

Efficacy of BET inhibitor in the HT1080 human fibrosarcoma xenograft model.

| Group | Treatment | Dose route, regimen | % TGI[a] |
|---|---|---|---|
| 1 | Vehicle | 0 mg/kg/day PO, QDx14 | — |
| 2 | Compound of Example 40 | 10 mg/kg/day PO, BID x 14 | −1 |
| 3 | Compound of Example 40 | 30 mg/kg/day PO, BID x 14 | 14 |
| 4 | Compound of Example 40 | 100 mg/kg/day PO, BID x 14 | 52** |

[a]Tumor growth inhibition, % TGI = 100 − mean tumor volume of treatment group/mean tumor volume of control group × 100. The p values (as indicated by asterisks) are derived from Student's T test comparison of treatment group vs. control group. Based on day 18.
**p < 0.01.

TABLE 7

Efficacy of BET inhibitor in the MV4-11 human AML xenograft model

| Group | Treatment | Dose route, regimen | % TGI[a] |
|---|---|---|---|
| 1 | Vehicle | 0 mg/kg/day PO, QDx14 | — |
| 2 | Compound of Example 40 | 25 mg/kg/day PO, BID x 14 | 14[b] |
| 3 | Compound of Example 40 | 50 mg/kg/day PO, BID x 14 | 42[c]** |
| 4 | Compound of Example 40 | 100 mg/kg/day PO, BID 5 on, 3 off x 2 | 67[d]** |

[a]Tumor growth inhibition, % TGI = 100 − mean tumor volume of treatment group/mean tumor volume of control group × 100. The p values (as indicated by asterisks) are derived from Student's T test comparison of treatment group vs. control group. Based on day 31.
**p < 0.01.
[b]10% mortality.
[c]30% mortality
[d]40% mortality LPS (Lipopolysaccharide) Induced IL-6 Production Mouse Assay Compounds of the Examples listed in Table 8 were assayed for their ability to inhibit LPS (lipopolysaccharide) induced IL-6 production in mice. Severe combined immunodeficient female mice (8 per group) received an intraperitoneal challenge of lipopolysaccharide (2.5 mg/kg, L2630 E. coli 0111:B4) one hour after oral administration (PO) or intraperitoneal administration (IP) of compounds in a solution of 2% ethanol, 5% Tween-80, 20% PEG-400 and 73% (0.2% hydroxypropylmethylcellulose in water). Mice were euthanized 2 hours after lipopolysaccharide injection, blood was removed by cardiac puncture, and then the serum harvested from the blood samples was frozen at −80° C. On the day of the assay the serum samples were brought to room temperature and then diluted 1:20 in phosphate-buffered saline containing 2% bovine serum albumin. Interleukin-6 measurements were performed using a cytokine assay from Meso Scale Discovery (Gaithersburg, Md.) for mouse serum analysis according to the manufacturer's protocol and read on a SECTOR Imager 6000 (Meso Scale Discovery, Gaithersburg, Md.) instrument. Statistical analysis was performed using Prism software (version 5.0) incorporating Dunnett's one way ANOVA. The IL-6 mean and standard deviation of the group of vehicle treated animals were compared with the IL-6 mean and standard deviation of the group treated with drug. A p value <0.05 means that there is less than a 5% probability that the mean values in the two groups are equal. The % inhibition values in Table 8 all exhibited a p value less than 0.05.

TABLE 8

Inhibition of LPS induced IL-6 production

| Compound of Example No. | % inhibition |
|---|---|
| 40 | 84.7 at 50 mg/kg (IP) |
| 40 | 72.7 at 30 mg/kg (PO) |
| 40 | 52.4 at 10 mg/kg (PO) |
| 40 | 28.7 at 3 mg/kg (PO) |
| 47 | 33.0 at 3 mg/kg (PO) |

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof. All publications, patents, and patent applications cited herein are hereby incorporated by reference in their entirety for all purposes.

The invention claimed is:

1. A compound of formula (I), or a pharmaceutically acceptable salt thereof

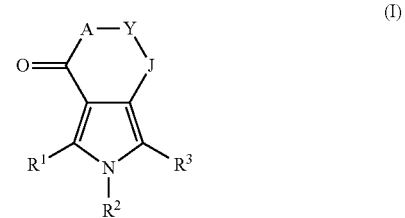

(I)

wherein
  A is C(R$^8$R$^9$);
  Y is C(R$^6$R$^7$);
  J is C(R$^4$R$^5$);
  R$^1$ is C$_1$-C$_3$ alkyl;
  R$^2$ is hydrogen or C$_1$-C$_3$ alkyl;
  R$^3$ is X, wherein X is

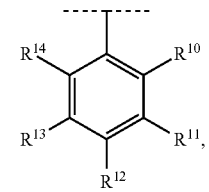

wherein X is substituted as set out in (i):
  (i) R$^{11}$, R$^{12}$, and R$^{14}$ are hydrogen, and R$^{10}$, and R$^{13}$ are selected from the following groups:
    R$^{10}$ is O-aryl, —S-aryl, or —O—C$_3$-C$_{14}$ cycloalkyl;
    R$^{13}$ is NR$^{16}$R$^{18}$, —NR$^{16}$—SO$_2$—NR$^{18}$—C$_1$-C$_3$ alkyl, —NR$^{16}$—SO$_2$—NR$^{18}$—C$_1$-C$_3$ haloalkyl, —NR$^{16}$—SO$_2$—C$_1$-C$_3$ alkyl, —NR$^{16}$—SO$_2$—C$_1$-C$_3$ haloalkyl, NH—C(O)—C$_1$-C$_3$ alkyl, or NH—C(O)-heteroaryl;

wherein any of said aryl groups of —O-aryl, —S-aryl; said heteroaryl groups of NH—C(O)-heteroaryl, and said cycloalkyl groups of —O—$C_3$-$C_{14}$ cycloalkyl is optionally substituted with 1 to 3 substituents selected from the group consisting of:
halo, $C_1$-$C_3$ alkyl, $C_1$-$C_3$ haloalkyl, CN, and $NR^{16}R^{18}$;
$R^4$ and $R^5$ are each independently selected from hydrogen, aryl, and $C_1$-$C_4$ alkyl;
$R^6$ and $R^7$ are each independently selected from hydrogen and $C_1$-$C_4$ alkyl;
$R^8$ and $R^9$ are each independently selected from hydrogen and $C_1$-$C_4$ alkyl; and
$R^{16}$ and $R^{18}$ are each independently selected from hydrogen and $C_1$-$C_3$ alkyl.

2. The compound of claim 1, or a pharmaceutically acceptable salt thereof, wherein $R^4$ and $R^5$ are hydrogen; and $R^8$ and $R^9$ are each hydrogen.

3. The compound of claim 2, or a pharmaceutically acceptable salt thereof, wherein $R^2$ is hydrogen.

4. The compound of claim 1, or a pharmaceutically acceptable salt thereof, wherein $R^1$ is methyl.

5. The compound of claim 4, or a pharmaceutically acceptable salt thereof, wherein $R^{13}$ is $NR^{16}R^{18}$, —$NR^{16}$—$SO_2$—$C_1$-$C_3$ alkyl, or —NH—$SO_2$—$C_1$-$C_3$ haloalkyl.

6. The compound of claim 5, or a pharmaceutically acceptable salt thereof, wherein $R^{10}$ is O-aryl.

7. The compound of claim 6, or a pharmaceutically acceptable salt thereof, wherein $R^{10}$ is O-phenyl or is O-phenyl which is substituted with 1 to 3 independently groups independently selected from the group consisting of halo.

8. The compound of claim 7, or a pharmaceutically acceptable salt thereof, wherein $R^{10}$ is —O-2,4-difluorophenyl.

9. The compound of claim 1, or a pharmaceutically acceptable salt thereof, wherein said compound is selected from the group consisting of:
1-(5-amino-2-phenoxyphenyl)-3-methyl-2,5,6,7-tetrahydro-4H-isoindol-4-one;
N-[3-(3-methyl-4-oxo-4,5,6,7-tetrahydro-2H-isoindol-1-yl)-4-phenoxyphenyl]methanesulfonamide;
N-[3-(2,3-dimethyl-4-oxo-4,5,6,7-tetrahydro-2H-isoindol-1-yl)-4-phenoxyphenyl]methanesulfonamide;
N-[3-(2,3-dimethyl-4-oxo-4,5,6,7-tetrahydro-2H-isoindol-1-yl)-4-phenoxyphenyl]acetamide;
1-[5-amino-2-(phenylsulfanyl)phenyl]-3-methyl-2,5,6,7-tetrahydro-4H-isoindol-4-one;
N-[3-(3-methyl-4-oxo-4,5,6,7-tetrahydro-2H-isoindol-1-yl)-4-(phenylsulfanyl)phenyl]methanesulfonamide;
1-[5-amino-2-(2,4-difluorophenoxy)phenyl]-3-methyl-2,5,6,7-tetrahydro-4H-isoindol-4-one;
N-[4-(2,4-difluorophenoxy)-3-(3-methyl-4-oxo-4,5,6,7-tetrahydro-2H-isoindol-1-yl)phenyl]methanesulfonamide;
N-[4-(2,4-difluorophenoxy)-3-(3-methyl-4-oxo-4,5,6,7-tetrahydro-2H-isoindol-1-yl)phenyl]ethanesulfonamide;
N-[4-(2,4-difluorophenoxy)-3-(3-methyl-4-oxo-4,5,6,7-tetrahydro-2H-isoindol-1-yl)phenyl]-2,2,2-trifluoroethanesulfonamide;
N'-[4-(2,4-difluorophenoxy)-3-(3-methyl-4-oxo-4,5,6,7-tetrahydro-2H-isoindol-1-yl)phenyl]-N,N-dimethylsulfuric diamide;
N-[4-(2,4-difluorophenoxy)-3-(3-methyl-4-oxo-4,5,6,7-tetrahydro-2H-isoindol-1-yl)phenyl]acetamide;
N-[4-(2,4-difluorophenoxy)-3-(3-methyl-4-oxo-4,5,6,7-tetrahydro-2H-isoindol-1-yl)phenyl]-1H-pyrrole-2-carboxamide;
N-{4-[(4,4-difluorocyclohexyl)oxy]-3-(3-methyl-4-oxo-4,5,6,7-tetrahydro-2H-isoindol-1-yl)phenyl}ethanesulfonamide;
1-(5-amino-2-phenoxyphenyl)-3,6-dimethyl-2,5,6,7-tetrahydro-4H-isoindol-4-one;
N-[3-(3,6-dimethyl-4-oxo-4,5,6,7-tetrahydro-2H-isoindol-1-yl)-4-phenoxyphenyl]methanesulfonamide;
N-{3-[3-methyl-6-(2-methylpropyl)-4-oxo-4,5,6,7-tetrahydro-2H-isoindol-1-yl]-4-phenoxyphenyl}methanesulfonamide;
N-{3-[3-methyl-4-oxo-6-(propan-2-yl)-4,5,6,7-tetrahydro-2H-isoindol-1-yl]-4-phenoxyphenyl}methanesulfonamide; and
N-[3-(3-methyl-4-oxo-6-phenyl-4,5,6,7-tetrahydro-2H-isoindol-1-yl)-4-phenoxyphenyl]methanesulfonamide.

10. A pharmaceutical composition comprising a therapeutically effective amount of a compound of formula (I) according to claim 1, or a pharmaceutically acceptable salt thereof, in combination with a pharmaceutically acceptable carrier.

* * * * *